US011119039B2

(12) United States Patent
Mohseni et al.

(10) Patent No.: US 11,119,039 B2
(45) Date of Patent: *Sep. 14, 2021

(54) INTERFEROMETRIC PARALLEL DETECTION USING ANALOG DATA COMPRESSION

(71) Applicant: HI LLC, Los Angeles, CA (US)

(72) Inventors: Hooman Mohseni, Santa Monica, CA (US); Haowen Ruan, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,488

(22) Filed: Apr. 7, 2020

(65) Prior Publication Data

US 2020/0333245 A1    Oct. 22, 2020

Related U.S. Application Data

(60) Provisional application No. 62/834,504, filed on Apr. 16, 2019, provisional application No. 62/855,380, filed on May 31, 2019.

(51) Int. Cl.
| | | |
|---|---|---|
| *G01N 21/359* | (2014.01) | |
| *A61B 5/00* | (2006.01) | |
| *G01B 9/02* | (2006.01) | |

(52) U.S. Cl.
CPC ........ *G01N 21/359* (2013.01); *A61B 5/0066* (2013.01); *G01B 9/02091* (2013.01)

(58) Field of Classification Search
CPC . G01N 21/359; A61B 5/0066; G01B 9/02091
See application file for complete search history.

(56) References Cited

U.S. PATENT DOCUMENTS

| | | |
|---|---|---|
| 7,519,246 B2 | 4/2009 | Welch et al. |
| 8,654,320 B2 | 2/2014 | Hasegawa et al. |
| (Continued) | | |

FOREIGN PATENT DOCUMENTS

| | | |
|---|---|---|
| JP | 2007114160 | 5/2007 |
| WO | WO2015109005 | 7/2015 |

OTHER PUBLICATIONS

Dominik Wyser, et al., "Wearable and modular functional near-infrared spectroscopy instrument with multidistance measurements at four wavelengths", Neurophotonics, vol. 4, No. 04, Aug. 18, 2017, p. 1, XP055618655.

(Continued)

*Primary Examiner* — Dominic J Bologna
(74) *Attorney, Agent, or Firm* — Michael J. Bolan; Vista IP Law Group, LLP

(57) ABSTRACT

Source light having a range of optical wavelengths is generated. The source light is split into sample light and reference light. The sample light is delivered into a sample, such that it is scattered by the sample, resulting in signal light that exits the sample. The signal light and reference light are combined into an interference light pattern having optical modes. Different subsets of the optical modes of the interference light pattern are respectively detected, and high-bandwidth analog signals respectively corresponding to the different subsets of optical modes of the interference light pattern are output. At least one characteristic is extracted from each of the plurality of high-bandwidth analog signals, and low-bandwidth digital signals respectively comprising the extracted characteristics are output. The sample is analyzed based on the low-bandwidth digital signals.

28 Claims, 23 Drawing Sheets

(56) References Cited

U.S. PATENT DOCUMENTS

| | | | |
|---|---|---|---|
| 9,946,344 B2 | 4/2018 | Ayaz et al. | |
| 10,371,614 B2 | 8/2019 | Hosoda et al. | |
| 2002/0122236 A1* | 9/2002 | Fisher | A61M 25/0041 359/278 |
| 2004/0039298 A1* | 2/2004 | Abreu | A61B 3/0025 600/558 |
| 2004/0150829 A1* | 8/2004 | Koch | G01B 9/02041 356/477 |
| 2005/0057756 A1* | 3/2005 | Fang-Yen | G01B 9/0209 356/497 |
| 2006/0244973 A1* | 11/2006 | Yun | G01B 9/02091 356/511 |
| 2008/0094613 A1* | 4/2008 | de Boer | G01B 9/02044 356/73 |
| 2008/0094637 A1* | 4/2008 | de Boer | G01B 9/02091 356/479 |
| 2016/0345880 A1 | 12/2016 | Nakaji et al. | |
| 2017/0227445 A1 | 8/2017 | Nakaji | |
| 2018/0249911 A1 | 9/2018 | Hosoda et al. | |
| 2020/0333129 A1* | 10/2020 | Mohseni | G01B 9/02083 |
| 2020/0333130 A1* | 10/2020 | Ruan | G01N 21/4738 |

OTHER PUBLICATIONS

Hubin Zhao, et al., "Review of recent progress toward a fiberless, whole-scalp diffuse optical tomography system", Neurophotonics, vol. 5, No. 01, Sep. 26, 2017, p. 1, XP055619174.

Yanlu Li et al: "On-chip laser Doppler vibrometer for arterial pulse wave velocity measurement", Biomedical Optics Express, vol. 4, No. 7, Jun. 27, 2013 (Jun. 27, 2013), p. 1229, XP055619911.

Soren Aasmul et al: "Towards a compact multi-laser-beam device for cardiovascular screening", Retrieved from the Internet; Apr. 1, 2017 (Apr. 1, 2017 ), XP055619237; XP055619908.

Lefteris Gounaridis et al: "Design of grating couplers and MMI couplers on the TriPleX platform enabling ultra-compact photonic-based biosensors", Sensors and Actuators B: Chemical, vol. 209, Mar. 1, 2015 (Mar. 1, 2015), pp. 1057-1063, XP055619192.

Zhao Wang et al: "Silicon photonic integrated circuit swept-source optical coherence tomography receiver with dual polarization, dual balanced, in-phase and quadrature detection", Biomedical Optics Express, vol. 6, No. 7, Jun. 17, 2015 (Jun. 17, 2015), p. 2562, XP055620031.

C. Weimann et al: "Silicon photonic integrated circuit for fast and precise dual-comb distance metrology", Optics Express, vol. 25, No. 24, Nov. 16, 2017 (Nov. 16, 2017), p. 30091, XP055619005.

Artundo Inigo: "Photonic Integration : New Applications Are Visible", Mar. 1, 2017 (Mar. 1, 2017), XP055619204.

Wim Bogaerts: "Introduction to Silicon Photonics Circuit Design", Mar. 11, 2018 (Mar. 11, 2018 ), XP055617994.

Joost Brouckaert et al: "Integration of Photodetectors on Silicon Photonic Integrated Circuits (PICs) for Spectroscopic Applications", Oct. 25, 2010 (Oct. 25, 2010), XP055617942.

Marc Korczykowski, "Perfusion functional MRI reveals cerebral blood flow pattern under psychological stress", Departments of Radiology, Neurology, Psychiatry, and Psychology and Center for Functional Neuroimaging , University of Pennsylvania, Philadelphia, PA 19104; pp. 17804-17809, PNAS, Dec. 6, 2005, vol. 102, No. 49.

D. Borycki et al., "Interferometric Near-Infrared Spectroscopy (iNIRS) for determination of optical and dynamical properties of turbid media," Opt Express 24 (2016).

M. A. Choma et al., "Sensitivity advantage of swept source and Fourier domain optical coherence tomography," Opt. Express 11 (2003).

Z. Cheng et al., "On-chip photonic synapse," Sci. Advances 3, e1700160 (2017).

Z. Wang et al., "Silicon photonic integrated circuit swept-source optical coherence tomography receiver with dual polarization, dual balanced, in-phase and quadrature detection," Biomed. Opt. Express 6 (2015).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon on-insulator platform," Opt. Express 18(17), 18278-18283 (2010).

C. Li et al, "Compact polarization beam splitter for silicon photonic integrated circuits with a 340-nm-thick silicon core layer", Opt. Letters (2017).

L. Chen, C. R. Doerr, L. Buhl, Y. Baeyens, and R. A. Aroca, "Monolithically integrated 40-wavelength demultiplexer and photodetector array on silicon," IEEE Photon. Technol. Lett. 23(13), 869-871 (2011).

C. T. Santis et al., "High coherence semiconductor lasers based on integral high-Q resonators in hybrid Si/III-V platforms," PNAS 111 (2014).

Gratton G., Fabiani M., "Fast-optical Imaging of Human Brain Function," Frontiers in Human Neuroscience, vol. 4, Article 52, pp. 1-9, Jun. 2010.

Eggegracht A. T., et al., "Mapping Distributed Brain Function and Networks with Diffuse Optical Tomography," Nature Photonics 8 (2014)).

Hill D.K. and Keynes, R.D., "Opacity Changes in Stimulated Nerve," J. Physiol., vol. 108, pp. 278-281 (1949).

Foust A.J. and Rector D.M., "Optically Teasing Apart Neural Swelling and Depolarization," Neuroscience, vol. 145, pp. 887-899 (2007)).

Scott A. Diddams, et al, "Molecular fingerprinting with the resolved modes of a femtosecond laser frequency comb", Nature Letters, vol. 445 Feb. 8, 2007.

Shijun Xiao and Andrew M. Weiner, "2-D wavelength demultiplexer with potential for ≥ 1000 channels in the C-band", Optics Express, Jun. 28, 2004, vol. 12, No. 13.

M. Shirasaki, "Large angular dispersion by a virtually imaged phased array and its application to a wavelength demultiplexer", Optics Letters, vol. 21, No. 5, Mar. 1, 1996.

Kevin K. Tsia, "Simultaneous mechanical-scan-free confocal microscopy and laser microsurgery", Optics Letters, Jul. 15, 2009, vol. 34, No. 14.

S.R. Chinn and E.A. Swanson, "Optical coherence tomography using a frequency-tunable optical source", Optics Letters, Mar. 1, 1997, vol. 22, No. 5.

T. Bonin, G. Franke, M. Hagen-Eggert, P. Koch, and G. Hüttmann, "In vivo Fourier-domain full-field OCT of the human retina with 15 million A-lines/s," Optics Letters, Oct. 15, 2010, vol. 35, No. 20.

J. Fujimoto and E. Swanson, "The Development, Commercialization, and Impact of Optical Coherence Tomography.," Invest. Ophthalmol. Vis. Sci. 57, Oct. 1-13, 2016.

The Scientist and Engineer's Guide to Digital Signal Processing, "Chapter 9, Applications of the DFT", 16 pp.

Shoji Kishi, "Impact of swept cource optical coherence tomography on opthalmology", Department of Opthalmology, Gunma University Graduate School of Medicine, Maebashi, Japan, Sep. 29, 2015.

Wen Bao, et al., "Orthogonal dispersive spectral-domain optical coherence tomography", Optics Express, Apr. 21, 2014, vol. 22, No. 8.

PCT International Search Report and Written Opinion for International Appln. No. PCT/US2019/028881, Applicant HI LLC, forms PCT/ISA/210, 220 and 237 dated Sep. 18, 2019 (23 pages).

Wenjun Zhou, et al., "Highly parallel, interferometric diffusing wave spectroscopy for monitoring cerebral blood flow dynamics", Optica, May 2018, vol. 5, No. 5 (10 pages).

* cited by examiner

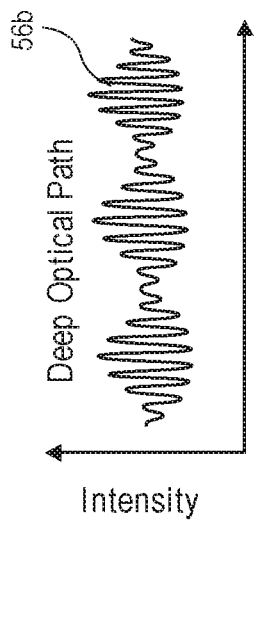
FIG. 5B
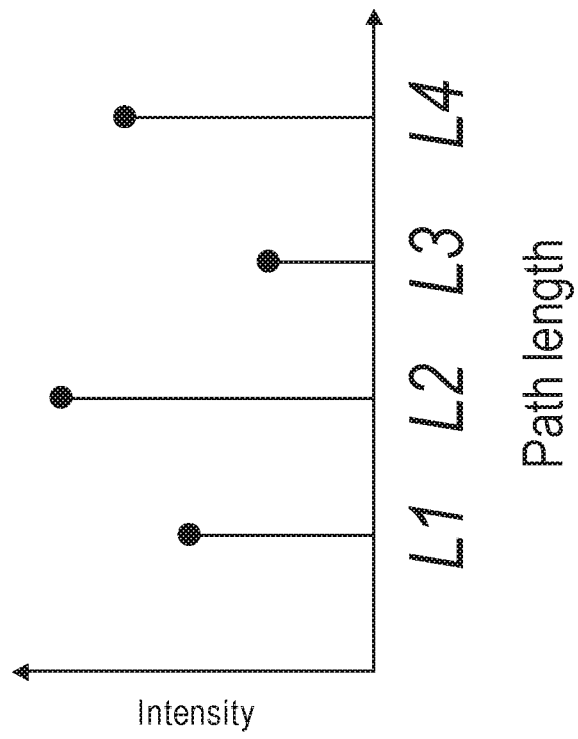
FIG. 6B
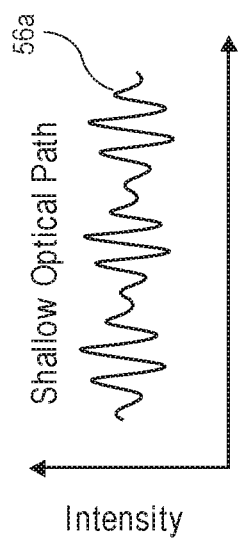
FIG. 5A
FIG. 6A

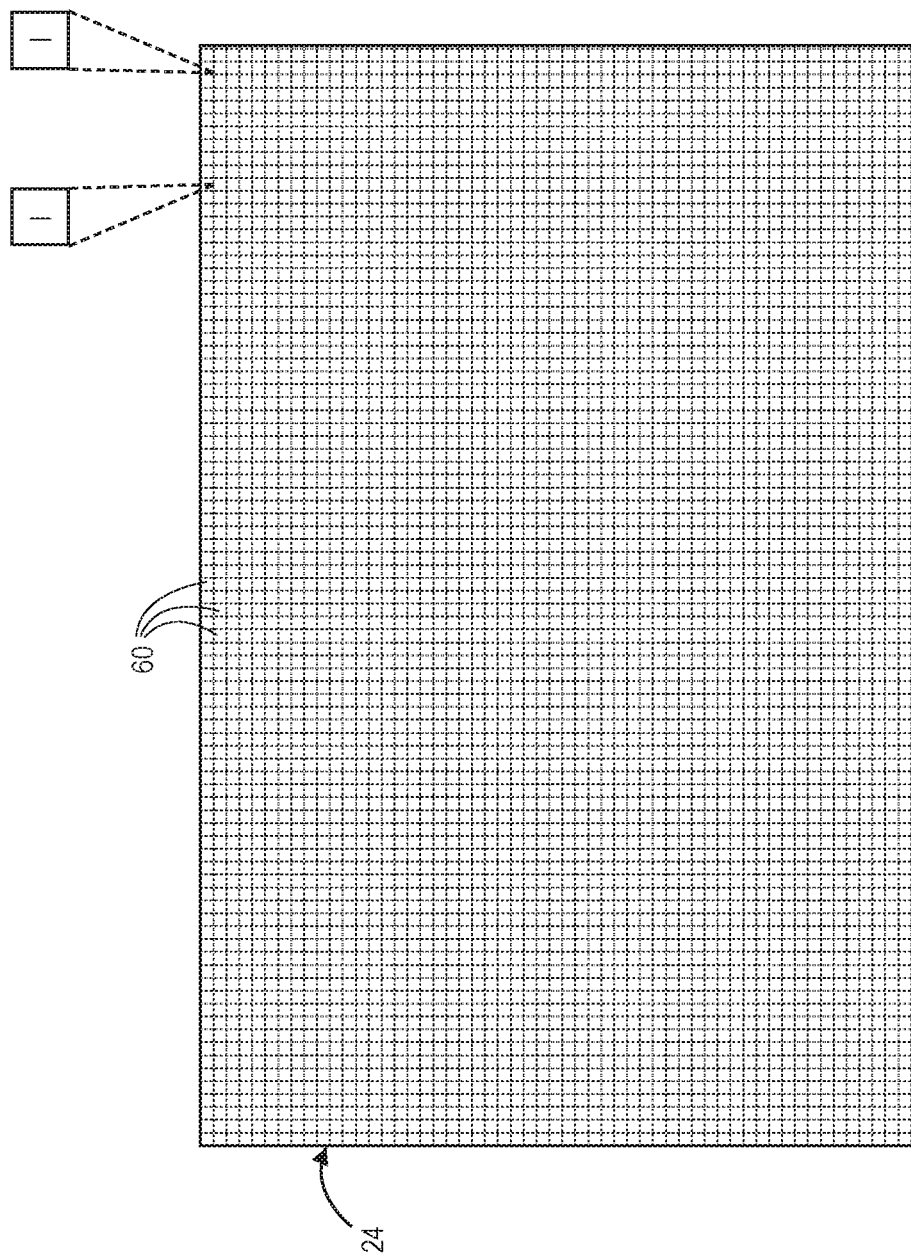

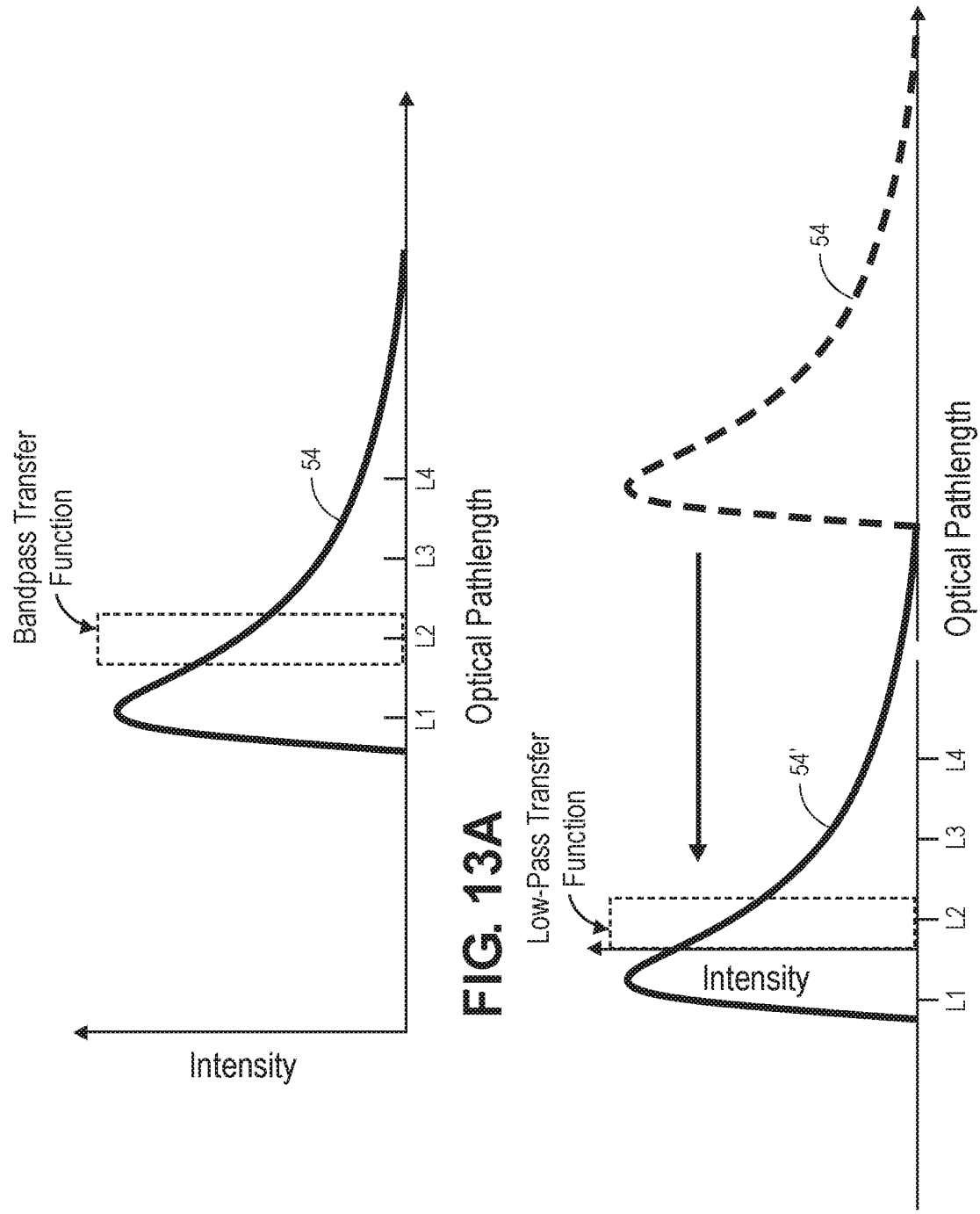

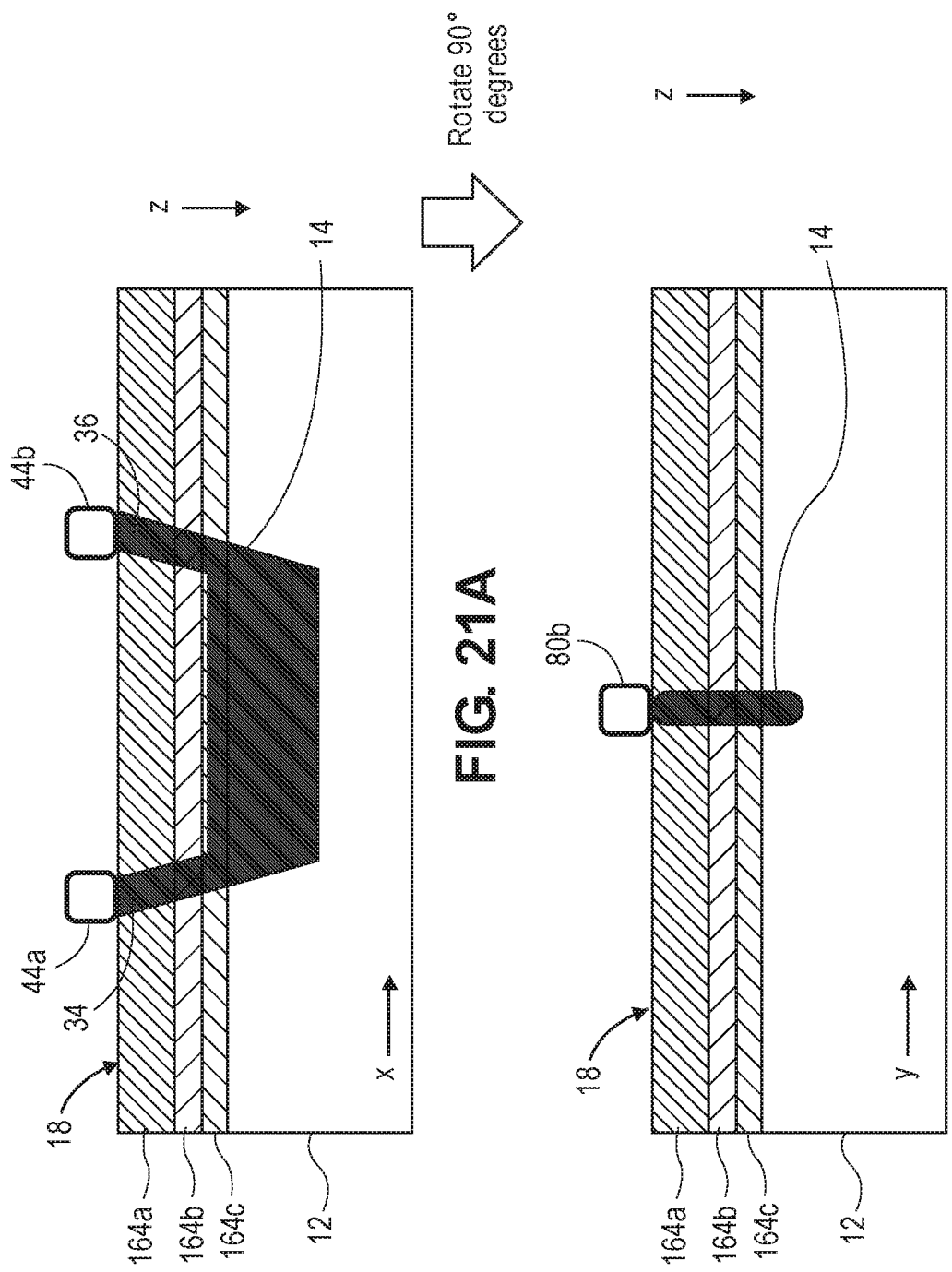

INTERFEROMETRIC PARALLEL DETECTION USING ANALOG DATA COMPRESSION

RELATED APPLICATION DATA

Pursuant to 35 U.S.C. § 119(e), this application claims the benefit of U.S. Provisional Application Ser. No. 62/834,504, filed Apr. 16, 2019, and U.S. Provisional Application Ser. No. 62/855,380, filed May 31, 2019, which are expressly incorporated herein by reference.

FIELD OF THE INVENTION

The present inventions relate to methods and systems for non-invasive measurements in the human body, and in particular, methods and systems related to detecting a physiologically-dependent optical signal in the human body, e.g., the brain.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for detecting neural activity in the brain for brain-computer interfacing). In summary, light scattering has presented challenges for optical detection techniques in achieving high spatial resolution at deeper depths inside tissue. Moreover, the diffusive nature of light propagation also creates challenges for measurements of fast changes in optical scattering inside tissue, since essentially all paths between source and detector are highly scattered to begin with.

One commercially available non-invasive imaging method, referred to as optical coherence tomography (OCT), is capable of acquiring images with high z-resolution (depth) (see James Fujimoto, et al., "*The Development, Commercialization, and Impact of Optical Coherence Tomography*," Investigative Ophthalmology & Visual Science, Vol. 57, OCT1-OCT13 (2016). Traditional OCT systems use coherent light (typically light in the near-infrared spectrum) to capture sub-surface images within optical scattering media (such as biological tissue) at a micrometer-resolution. The OCT system enables optical imaging of samples in depth within a ballistic photon regime. In particular, the OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. An interference light pattern is formed by any sample light that has an optical pathlength that matches, within the coherence length of the optical source, the optical pathlength traveled by the reference light. The intensity of the backscattering sample light having that optical pathlength can then be detected within the interference light pattern.

Previous commercial OCT systems acquire data in the time domain (TD-OCT), and coherence gate the backscattered light from various depths in the biological tissue by adjusting the position of the mirror to tune the optical pathlength of the reference, such that only sample light having the matching optical pathlength is selected for detection at any given time. An alternative approach to coherence gating, referred to as Fourier domain optical coherence tomography (FD-OCT) is an imaging modality that does not involve adjusting the delay of the reference arm, but rather involves acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. It has been shown that FD-OCT has a significantly greater signal-to-noise (SNR) than FD-OCT (see Michael A. Choma, et al., "*Sensitivity Advantage of Swept Source and Fourier Domain Optical Coherence Tomography*," Optics Express, Vol. 11, No. 18, 8 Sep. 2003).

Two distinct methods have been developed that employ the FD approach: (1) swept-source (SS-OCT), which time-encodes optical wavelengths by rapidly tuning a narrowband optical source through a broad optical bandwidth; and 2) spectral domain (SD-OCT), which uses a broadband light source to achieve spectral discrimination. Out of the OCT techniques, SS-OCT is the most closely related to the present inventions (see S. R. Chinn, et al., "*Optical Coherence Tomography Using a Frequency-Tunable Optical Source*," Optics Letter. Vo. 22, No. 5, pp. 340-342 (1997). SS-OCT has been reported to use a camera to measure the full-field OCT image (see Tim Bonin, et al., "*In Vivo Fourier-Domain Full-Field OCT of the Human Retina with 15 Million A-Lines/S*," Optics Letter, Vol. 35, No. 20, Oct. 15, 2010). However, the camera-based SS-OCT system described in Bonin lacks the necessary sensitivity and image quality.

Regardless of the type, the depth at which an OCT system images biological tissue is limited, because the quantity of ballistic photons decreases exponentially over depth. At greater depths the proportion of light that escapes without scattering (i.e., the ballistic light) is too small to be detected. Thus, the clinical applications of OCT have, thus far, been limited to imaging sub-surface features, such as obtaining high-resolution ophthalmic images of the retina. As such, OCT is presently insufficient for measuring neural activity in the deeper regions of the brain (i.e., deeper than 2 mm).

Another type of diffusive optical measurement technique, referred to as interferometric Near-Infrared Spectroscopy (iNIRS) (see Borycki, Dawid, et al., "*Interferometric Near-Infrared Spectroscopy (iNIRS) for Determination of Optical and Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of thick scattering media at a depth on the order of a few centimeters at the cost of reduced resolution.

The current state of the art of iNIRS utilizes a single optical channel that measures the multiple-scattered photons from scattering samples, and therefore, has a limited data throughput, which leads to a lower SNR and detection speed. In response to the shortfalls of single-channel iNIRS systems, parallel iNIRS systems, which utilize multiple parallel channels to achieve parallel detection of the multi-scattered photons from scattering samples, have been developed thereby enabling higher data throughput, SNR, and detection speed. Such parallel iNIRS systems currently rely on commercially available high-speed cameras to detect the multi-scattered photons from the scattering samples.

However, such cameras are relatively expensive, bulky, and power hungry, and produce a massive amount of data (most of which is void of information of interest), thereby demanding high data storage and preventing real-time operation of such iNIRS systems without utilizing very powerful computing units. As such, currently known parallel iNIRS systems cannot be practically scaled down to wearable or portable form factors. These issues are particularly problematic for brain-computer interfacing applications for the detection of neural brain activity, which not only require scalability of the resulting system to be portable and wearable, but also require many optical detection units (each of which would include a camera) to be arrayed in a wearable unit over the head of a user, thereby exacerbating the expense, bulkiness, and heat dissipation of the resulting wearable unit. Furthermore, one emerging neural activity measurement technique, known as diffuse correlation spectroscopy (DCS), uses a computationally costly autocorrelation technique to detect physiologically-dependent optical signals, and thus, its application is particularly problematic for use in parallel iNIRS systems.

There, thus, remains a need to increase the data throughput of an optical detection system designed to be portable, while minimizing the data processing requirements and obviating the need for high-speed, expensive, and bulky cameras.

SUMMARY OF THE INVENTION

In accordance with one aspect of the present inventions, a non-invasive optical detection system comprises an optical source configured for generating source light having a range of optical wavelengths during each of at least one measurement period. In one embodiment, the optical source is configured for sweeping the source light over the range of optical wavelengths during each of the measurement period(s).

The non-invasive optical detection system further comprises an interferometer configured for splitting the source light into sample light, which propagates along a sample arm of the interferometer, and reference light, which propagates along a reference arm of the interferometer, delivering the sample light into a sample, such that the sample light is scattered by the sample, resulting in signal light that exits the sample, and combining, during each of the measurement period(s), the signal light and the reference light into an interference light pattern having a plurality of optical modes. In a preferred embodiment, each of the measurement period(s) is equal to or less than a speckle decorrelation time of the sample.

The non-invasive optical detection system further comprises a plurality of optical detectors configured for respectively detecting different subsets of the plurality of optical modes of the interference light pattern, and respectively outputting a plurality of high-bandwidth analog signals corresponding to the plurality of different subsets of optical modes of the interference light pattern. Each subset of optical modes of the interference light pattern may comprises a single optical mode or may comprise multiple spatially adjacent optical modes.

The non-invasive optical detection system further comprises analog compression circuitry configured for respectively extracting at least one characteristic of each of the plurality of high-bandwidth analog signals, and respectively outputting a plurality of low-bandwidth digital signals respectively comprising the extracted characteristics. The non-invasive optical detection system may further comprise an optical detector chip in which the plurality of optical detectors and the analog compression circuitry are integrated.

The non-invasive optical detection system further comprises at least one processor configured for analyzing the sample based on the extracted characteristics in the plurality of low-bandwidth digital signals. In one embodiment, the processor(s) is further configured for reducing the plurality of low-bandwidth digital signals to a single low-bandwidth digital signal, in which case, the processor(s) is configured for analyzing the sample based on the extracted characteristic(s) in the single low-bandwidth digital signal. In one embodiment, the sample is an anatomical structure, such that the signal light is physiologically is encoded with a physiologically-dependent optical signal in the anatomical structure, in which case, the processor(s) may be configured for identifying a change in the physiologically-dependent optical signal in the anatomical structure based on the plurality of low-bandwidth digital signals. The anatomical structure may be a brain, such that the physiologically-dependent optical signal (e.g., a fast-optical signal or a hemodynamic signal) is indicative of neural activity, in which case, the processor(s) may be configured for identifying neural activity in the brain based on the identified change in the physiologically-dependent optical signal.

In one embodiment, the analog compression circuitry comprises a plurality of filter assemblies configured for respectively frequency filtering the plurality of high-bandwidth analog signals, and respectively outputting a plurality of pathlength-encoded analog signals encoded with one of a plurality of optical pathlengths of the signal light. In this case, the processor(s) is configured for analyzing the sample at a depth corresponding to the one optical pathlength. As one example, the plurality of filter assemblies respectively comprises a plurality of band-pass filters configured for respectively band-pass filtering the plurality of high-bandwidth analog signals, and respectively outputting the plurality of pathlength-encoded analog signals. As another example, the plurality of frequency filter assemblies respectively comprises a plurality of mixers configured for respectively frequency mixing the plurality of high-bandwidth analog signals with a base frequency, and respectively outputting a plurality of frequency down-shifted analog signals; and a plurality of low-pass filters configured for respectively low-pass filtering the plurality of frequency down-shifted analog signals, and respectively outputting the plurality of pathlength-encoded analog signals.

The analog compression circuitry may further comprise a plurality of rectifiers configured for respectively rectifying the plurality of pathlength-encoded analog signals, and respectively outputting a plurality of rectified analog signals; a plurality of smoothing circuits configured for respectively smoothing the plurality of rectified analog signals, and respectively outputting a plurality of low-bandwidth analog signals comprising the extracted characteristics; and at least one analog-to-digital converter (ADC) configured for digitizing the plurality of low-bandwidth analog signals, and outputting the plurality of low-bandwidth digital signals. In one embodiment, a single ADC is used, in which case, the non-invasive optical detection system may further comprise a plurality of switches coupled between the plurality of smoothing circuits and the single ADC, wherein the plurality of switches is configured for being sequentially closed, such that the ADC serially digitizes the plurality of low-bandwidth analog signals, and serially outputs the plurality of low-bandwidth digital signals.

In an optional embodiment, the non-invasive optical detection system further comprises an optical pathlength selection device configured for selecting the one optical pathlength by shifting a transfer function of the plurality of filter assemblies and a frequency band of the plurality of high-bandwidth analog signals relative to each other.

In one embodiment, the optical pathlength selection device may be configured for optically shifting the transfer function of the respective filter assembly and the frequency band of the plurality of high-bandwidth analog signals relative to each other. As one example, the optical pathlength selection device may comprise a controller configured for mechanically adjusting a mirror arrangement that adjusts the length of the reference arm of the interferometer relative to the length of the sample arm of the interferometer, thereby optically shifting the frequency band the plurality of high-bandwidth analog signals. As another example, the pathlength selection device may comprise a controller configured for adjusting an optical sweep rate at which the optical source is swept over a range of optical wavelengths during each measurement period(s), thereby optically shifting the frequency band the plurality of high-bandwidth analog signals.

In another embodiment, the optical pathlength selection device may be configured for electrically shifting the transfer function of the respective filter assembly and the plurality of high-bandwidth analog signals relative to each other. In one example, the optical pathlength selection device comprises a k-clock module configured for generating a k-clock signal having a frequency, and a phased lock loop (PLL) circuit configured for generating a control signal having a frequency that is an adjustable ratio of the frequency of the k-clock signal. The plurality of filter assemblies may be configured for electrically shifting the transfer function and the frequency band of the plurality of high-bandwidth analog signals relative to each other in response to the adjusted frequency of the control signal.

In one embodiment, the extracted characteristic(s) comprises an envelope of at least one frequency of each high-bandwidth analog signal. In another embodiment, the analog compression circuitry is configured for computing the squared amplitude of the Fourier transform of each of the plurality of high-bandwidth analog signals, and extracting the characteristic(s) from the squared amplitude of the Fourier transform of each of the plurality of high-bandwidth analog signals. For example, the analog compression circuitry may comprise a first plurality of rectifiers configured for respectively rectifying the plurality of high-bandwidth analog signals, and respectively outputting a first plurality of rectified analog signals, a plurality of low-pass filters configured for respectively low-pass filtering the first plurality of rectified analog signals, and respectively outputting a plurality of low-bandwidth analog signals, and a second plurality of rectifiers configured for respectively rectifying the plurality of low-bandwidth analog signals, and respectively outputting a second plurality of rectified analog signals respectively representing the absolute squares of the Fourier transforms of the plurality of high-bandwidth analog signals. In this case, the analog compression circuitry may be configured for respectively extracting the characteristic(s) from each of the second plurality of rectified analog signals.

In one embodiment, the characteristic(s) extracted from the squared amplitude of the Fourier transform of each of the plurality of high-bandwidth analog signals may comprise a plurality of points on an envelope of the squared amplitude of the Fourier transform of each of the plurality of high-bandwidth analog signals. In this case, the analog compression circuitry may comprise a plurality of sets of band-pass filters, each set of band-pass filters respectively having a plurality of different center frequencies. The plurality of sets of band-pass filters may be configured for respectively band-pass filtering the squared amplitude of the Fourier transforms of the plurality of high-bandwidth analog signals, and respectively outputting a plurality of sets of band-pass filtered analog signals, each set of band-pass filtered analog signals respectively comprising the plurality of points. The analog compression circuitry may further comprise a plurality of sets of smoothing circuits configured for respectively smoothing the plurality of sets of band-pass filtered analog signals, and respectively outputting a plurality of sets of low-bandwidth analog signals, each set of low-bandwidth analog signals respectively comprising the plurality of points. The analog compression circuitry may further comprise at least one analog-to-digital converter (ADC) configured for digitizing the plurality of sets of low-bandwidth analog signals, and outputting the plurality of low-bandwidth digital signals.

In another embodiment, the characteristic(s) extracted from the squared amplitude of the Fourier transform of each of the plurality of high-bandwidth analog signals may comprise an area underneath an envelope of the squared amplitude of the Fourier transform of each of the plurality of high-bandwidth analog signals. In this case, the analog compression circuitry may comprise a plurality of integrators configured for respectively integrating the squared amplitude of the Fourier transforms of the plurality of high-bandwidth analog signals, and respectively outputting a plurality of low-bandwidth analog signals respectively comprising the areas; and at least one analog-to-digital converter (ADC) configured for digitizing the plurality of low-bandwidth analog signals, and outputting the plurality of low-bandwidth digital signals.

In accordance with another aspect of the present inventions, a non-invasive optical detection method comprises generating source light having a range of optical wavelengths during each of at least one measurement period, splitting the source light into sample light and reference light, delivering the sample light into a sample, such that the sample light is scattered by the sample, resulting in signal light that exits the sample, and combining, during each of the measurement period(s), the signal light and the reference light into an interference light pattern having a plurality of optical modes. One method further comprising sweeping the source light over the range of optical wavelengths during each measurement period(s). In a preferred method, each of the measurement period(s) is equal to or less than a speckle decorrelation time of the sample.

The method further comprises respectively detecting different subsets of the plurality of optical modes of the interference light pattern, and respectively outputting a plurality of high-bandwidth analog signals corresponding to the different subsets of optical modes of the interference light pattern. Each subset of optical modes of the interference light pattern may comprises a single optical mode or may comprise multiple spatially adjacent optical modes.

The method further comprises extracting at least one characteristic of each of the plurality of high-bandwidth analog signals, outputting a plurality of low-bandwidth digital signals respectively comprising the extracted characteristics, and analyzing the sample based on the extracted characteristics in the plurality of low-bandwidth digital signals. One method further comprises reducing the plurality of low-bandwidth digital signals to a single low-bandwidth digital signal, in which case, the sample is analyzed based on the extracted characteristic(s) in the single low-bandwidth digital signal. In one method, the sample is an anatomical structure, such that the signal light is physiologically encoded with a physiologically-dependent optical signal in the anatomical structure, and the change in the physiologically-dependent optical signal in the anatomical structure is identified based on the plurality of low-bandwidth digital signals. The anatomical structure may be a brain, such that the physiologically-dependent optical signal (e.g., a fast-optical signal or a hemodynamic signal) is indicative of neural activity, in which case, neural activity in the brain may be identified based on the identified change in the physiologically-dependent optical signal.

In one method, extracting the characteristic(s) from each of the plurality of high-bandwidth analog signals comprises respectively frequency filtering the plurality of high-bandwidth analog signals and outputting a plurality of pathlength-encoded analog signals encoded with one of a plurality of optical pathlengths of the signal light. In this case, the sample may be analyzed at a depth corresponding to the one optical pathlength. As one example, frequency filtering the plurality of high-bandwidth analog signals may comprise respectively band-pass filtering the plurality of high-bandwidth analog signals. As another example, frequency filtering the plurality of high-bandwidth analog signals may comprise respectively frequency mixing the plurality of high-bandwidth analog signals with a base frequency and outputting a plurality of frequency down-shifted analog signals, and respectively low-pass filtering the plurality of frequency down-shifted analog signals and outputting the plurality of pathlength-encoded analog signals.

This method may further comprise respectively rectifying the plurality of pathlength-encoded analog signals and outputting a plurality of rectified analog signals, respectively smoothing the plurality of rectified analog signals and outputting a plurality of low-bandwidth analog signals respectively comprising the extracted characteristics, and respectively digitizing the plurality of low-bandwidth analog signals and outputting the plurality of low-bandwidth digital signals. The plurality of low-bandwidth analog signals may be serially digitized, and the plurality of low-bandwidth digital signals may be serially outputted.

In an optional method, the plurality of high-bandwidth analog signals is filtered in accordance with a transfer function, and the one optical pathlength is selected by shifting the transfer function and a frequency band of the plurality of high-bandwidth analog signals relative to each other.

In one method, the transfer function and the frequency band of the plurality of high-bandwidth analog signals are optically shifted relative to each other. In one example, optically shifting the transfer function and the frequency band relative to each other may comprise adjusting the length of a reference arm along which the reference light propagates. In another example, optically shifting the transfer function and the frequency band of the plurality of high-bandwidth analog signals relative to each other comprises adjusting an optical sweep rate at which the optical source is swept over a range of optical wavelengths during each of the measurement period(s).

In another method, the transfer function and the frequency band of the plurality of high-bandwidth analog signals are electrically shifted relative to each other. In one example, electrically shifting the transfer function and the frequency band of the plurality of high-bandwidth analog signals relative to each other comprises generating a k-clock signal having a frequency, generating a control signal having a frequency that is an adjustable ratio of the frequency of the k-clock signal, and electrically shifting the transfer function and the frequency band of the plurality of high-bandwidth analog signals relative to each other in response to the adjusted frequency of the control signal.

In one method the extracted characteristic(s) comprises an envelope of at least one of frequency of the each high-bandwidth analog signal. Another method further comprises computing the squared amplitude of the Fourier transform of each of the plurality of high-bandwidth analog signals, and the characteristic(s) is extracted from the squared amplitude of the Fourier transform of each of the plurality of high-bandwidth analog signals. Computing the squared amplitude of the Fourier transform of each of the plurality of high-bandwidth analog signals may comprise respectively rectifying the plurality of high-bandwidth analog signals and outputting a first plurality of rectified analog signals, respectively low-pass filtering the first plurality of rectified analog signals and outputting a plurality of low-bandwidth analog signals, respectively rectifying the plurality of low-bandwidth analog signals and outputting a second plurality of rectified analog signals respectively representing the absolute squares of the Fourier transforms of the plurality of high-bandwidth analog signals, and respectively extracting the characteristic(s) from each of the absolute squares of the Fourier transforms of the second plurality of rectified analog signals.

In one method, the characteristic(s) extracted from the squared amplitude of the Fourier transform of each of the plurality of high-bandwidth analog signals may comprise a plurality of points on an envelope of the squared amplitude of the Fourier transform of each of the plurality of high-bandwidth analog signals. In this case, the method further comprises respectively band-pass filtering the absolute squares of the Fourier transforms of the plurality of high-bandwidth analog signals and outputting a plurality of sets of band-pass filtered analog signals, each set of band-pass filtered analog signals respectively comprising the plurality of points; respectively smoothing the plurality of sets of band-pass filtered analog signals and outputting a plurality of sets of low-bandwidth analog signals, each set of low-bandwidth analog signals respectively comprising the plurality of points; and digitizing the plurality of sets of low-bandwidth analog signals, thereby generating the plurality of low-bandwidth digital signals.

In another method, the characteristic(s) extracted from the squared amplitude of the Fourier transform of each of the plurality of high-bandwidth analog signals may comprise an area underneath an envelope of the squared amplitude of the Fourier transform of each of the plurality of high-bandwidth analog signals. In this case, the method may further comprise respectively integrating the squared amplitude of the Fourier transforms of the plurality of high-bandwidth analog signals and outputting a plurality of low-bandwidth analog signals respectively comprising the areas, and digitizing the plurality of low-bandwidth analog signals, thereby generating the plurality of low-bandwidth digital signals.

In accordance with still another aspect of the present inventions, a multi-channel optical detector chip comprises a plurality of optical detectors configured for respectively detecting different subsets of a plurality of optical modes of interference light pattern, and respectively outputting a plurality of high-bandwidth analog signals corresponding to the plurality of different subsets of optical modes of the light pattern. Each subset of optical modes of the light pattern may comprises a single optical mode or may comprise multiple spatially adjacent optical modes.

The multi-channel optical detector chip further comprises analog compression circuitry configured for respectively extracting at least one characteristic of each of the plurality of high-bandwidth analog signals, and respectively outputting a plurality of low-bandwidth digital signals respectively comprising the extracted characteristics.

In one embodiment, the analog compression circuitry comprises a plurality of filter assemblies configured for respectively frequency filtering the plurality of high-bandwidth analog signals, and respectively outputting a plurality of pathlength-encoded analog signals encoded with one of a plurality of optical pathlengths of the signal light. In this case, the processor(s) is configured for analyzing the sample at a depth corresponding to the one optical pathlength. As one example, the plurality of filter assemblies respectively comprises a plurality of band-pass filters configured for respectively band-pass filtering the plurality of high-bandwidth analog signals, and respectively outputting the plurality of pathlength-encoded analog signals. As another example, the plurality of frequency filter assemblies respectively comprises a plurality of mixers configured for respectively frequency mixing the plurality of high-bandwidth analog signals with a base frequency, and respectively outputting a plurality of frequency down-shifted analog signals; and a plurality of low-pass filters configured for respectively low-pass filtering the plurality of frequency down-shifted analog signals, and respectively outputting the plurality of pathlength-encoded analog signals.

The analog compression circuitry may further comprise a plurality of rectifiers configured for respectively rectifying the plurality of pathlength-encoded analog signals, and respectively outputting a plurality of rectified analog signals; a plurality of smoothing circuits configured for respectively smoothing the plurality of rectified analog signals, and respectively outputting a plurality of low-bandwidth analog signals comprising the extracted characteristics; and at least one analog-to-digital converter (ADC) configured for digitizing the plurality of low-bandwidth analog signals, and outputting the plurality of low-bandwidth digital signals. In one embodiment, a single ADC is used, in which case, the non-invasive optical detection system may further comprise a plurality of switches coupled between the plurality of smoothing circuits and the single ADC, wherein the plurality of switches is configured for being sequentially closed, such that the ADC serially digitizes the plurality of low-bandwidth analog signals, and serially outputs the plurality of low-bandwidth digital signals.

In one embodiment, the extracted characteristic(s) comprises an envelope of at least one frequency of each high-bandwidth analog signal. In another embodiment, the analog compression circuitry is configured for computing the squared amplitude of the Fourier transform of each of the plurality of high-bandwidth analog signals, and extracting the characteristic(s) from the squared amplitude of the Fourier transform of each of the plurality of high-bandwidth analog signals. For example, the analog compression circuitry may comprise a first plurality of rectifiers configured for respectively rectifying the plurality of high-bandwidth analog signals, and respectively outputting a first plurality of rectified analog signals, a plurality of low-pass filters configured for respectively low-pass filtering the first plurality of rectified analog signals, and respectively outputting a plurality of low-bandwidth analog signals, and a second plurality of rectifiers configured for respectively rectifying the plurality of low-bandwidth analog signals, and respectively outputting a second plurality of rectified analog signals respectively representing the absolute squares of the Fourier transforms of the plurality of high-bandwidth analog signals. In this case, the analog compression circuitry may be configured for respectively extracting the characteristic(s) from each of the second plurality of rectified analog signals.

In one embodiment, the characteristic(s) extracted from the squared amplitude of the Fourier transform of each of the plurality of high-bandwidth analog signals may comprise a plurality of points on an envelope of the squared amplitude of the Fourier transform of each of the plurality of high-bandwidth analog signals. In this case, the analog compression circuitry may comprise a plurality of sets of band-pass filters, each set of band-pass filters respectively having a plurality of different center frequencies. The plurality of sets of band-pass filters may be configured for respectively band-pass filtering the squared amplitude of the Fourier transforms of the plurality of high-bandwidth analog signals, and respectively outputting a plurality of sets of band-pass filtered analog signals, each set of band-pass filtered analog signals respectively comprising the plurality of points. The analog compression circuitry may further comprise a plurality of sets of smoothing circuits configured for respectively smoothing the plurality of sets of band-pass filtered analog signals, and respectively outputting a plurality of sets of low-bandwidth analog signals, each set of low-bandwidth analog signals respectively comprising the plurality of points. The analog compression circuitry may further comprise at least one analog-to-digital converter (ADC) configured for digitizing the plurality of sets of low-bandwidth analog signals, and outputting the plurality of low-bandwidth digital signals.

In another embodiment, the characteristic(s) extracted from the squared amplitude of the Fourier transform of each of the plurality of high-bandwidth analog signals may comprise an area underneath an envelope of the squared amplitude of the Fourier transform of each of the plurality of high-bandwidth analog signals. In this case, the analog compression circuitry may comprise a plurality of integrators configured for respectively integrating the squared amplitude of the Fourier transforms of the plurality of high-bandwidth analog signals, and respectively outputting a plurality of low-bandwidth analog signals respectively comprising the areas; and at least one analog-to-digital converter (ADC) configured for digitizing the plurality of low-bandwidth analog signals, and outputting the plurality of low-bandwidth digital signals.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5A is a timing diagram illustrating a series of fringe patterns of an interference light pattern corresponding to a shallow optical path;

FIG. 5B is a timing diagram illustrating a series of fringe patterns of an interference light pattern corresponding to a deep optical path;

FIG. 6A is a timing diagram illustrating exemplary oscillation frequency components of an interference light pattern generated by the non-invasive optical detection system of FIG. 1;

FIG. 6B is a timing diagram illustrating exemplary optical pathlength intensities corresponding to the exemplary oscillation frequency components of FIG. 6A;

FIG. 7 is a plan view of an optical detector array used in the non-invasive optical detection system of FIG. 1;

FIG. 13A is a timing diagram illustrating an exemplary TOF-intensity profile, wherein an optical pathlength is selected by a band-pass transfer function;

FIG. 13B is a timing diagram illustrating an exemplary TOF-intensity profile, wherein TOF-intensity profile is down-shifted and an optical pathlength is selected by a low-pass transfer function;

FIG. 21A is one profile view of one arrangement of the output port and input port of the wearable unit of FIG. 20, particularly illustrating the creation of a sample path in the head between the ports;

FIG. 21B is another profile view of the arrangement of the output port and input port of the wearable unit of FIG. 20;

DETAILED DESCRIPTION OF THE EMBODIMENTS

The embodiments of the non-invasive optical detection systems described herein are interferometric in that these optical detection systems mix detected signal light against reference light in order to increase the signal-to-noise ratio (SNR) of the signal light. These optical detection systems are described herein as being, e.g., Near-Infrared Spectroscopy (iNIRS) systems. This should be contrasted with conventional Optical Coherence Tomography (OCT) systems, which may utilize optical detector arrays in the form of camera pixels, but do so for a completely different purpose. That is, the non-invasive optical detection systems described herein focus on the measurement of multiple-scattered signal light of different depth-correlated optical pathlengths, as opposed to ballistic or single-scattered signal light measured by a conventional OCT system or a swept-source OCT (SS-OCT) system. Therefore, the non-invasive optical detection systems described herein are capable of detecting physiologically-dependent optical signals in tissue at a penetration depth of multiple centimeters.

Thus, the many camera pixels in the non-invasive optical detection systems described herein serve the purpose of increasing the SNR for such functional measurements within tissue at deeper depths, whereas known camera-based OCT approach, such as "full field OCT," utilizes an optical detector array to acquire actual images of the anatomical structure, and its use of many camera pixels, does not increase the SNR, but rather allows parallel imaging of many anatomical locations. Furthermore, unlike the non-invasive optical detection systems described herein, which provides for detection of multiple scattered light, the known camera-based OCT approach is not able to probe at deeper tissue depths because of its reliance on ballistic or single scattered light.

Notwithstanding the foregoing, it should be appreciated that the present inventions, in their broadest aspects, should not be limited to iNIRS systems, and may be embodied in any optical detection system that utilizes optical interferometry.

Significantly, unlike a conventional iNIRS system, which has a limited data throughput due to its single detector measurement of multi-scattered signal light, and thus has a lower signal-to-noise (SNR) and detection speed, the non-invasive optical detection systems described herein use an optical detector array to achieve parallel detection of the optical modes in the multiple-scattered signal light, thereby enabling higher data throughput, and thus a higher SNR and detection speed. The non-invasive optical detection systems described herein employ analog compression circuitry configured for significantly reducing the bandwidth of each of the optical modes of detected physiologically-encoded signal light, thereby allowing processing of many optical modes with minimal power consumption and minimal data storage.

Figure 1:
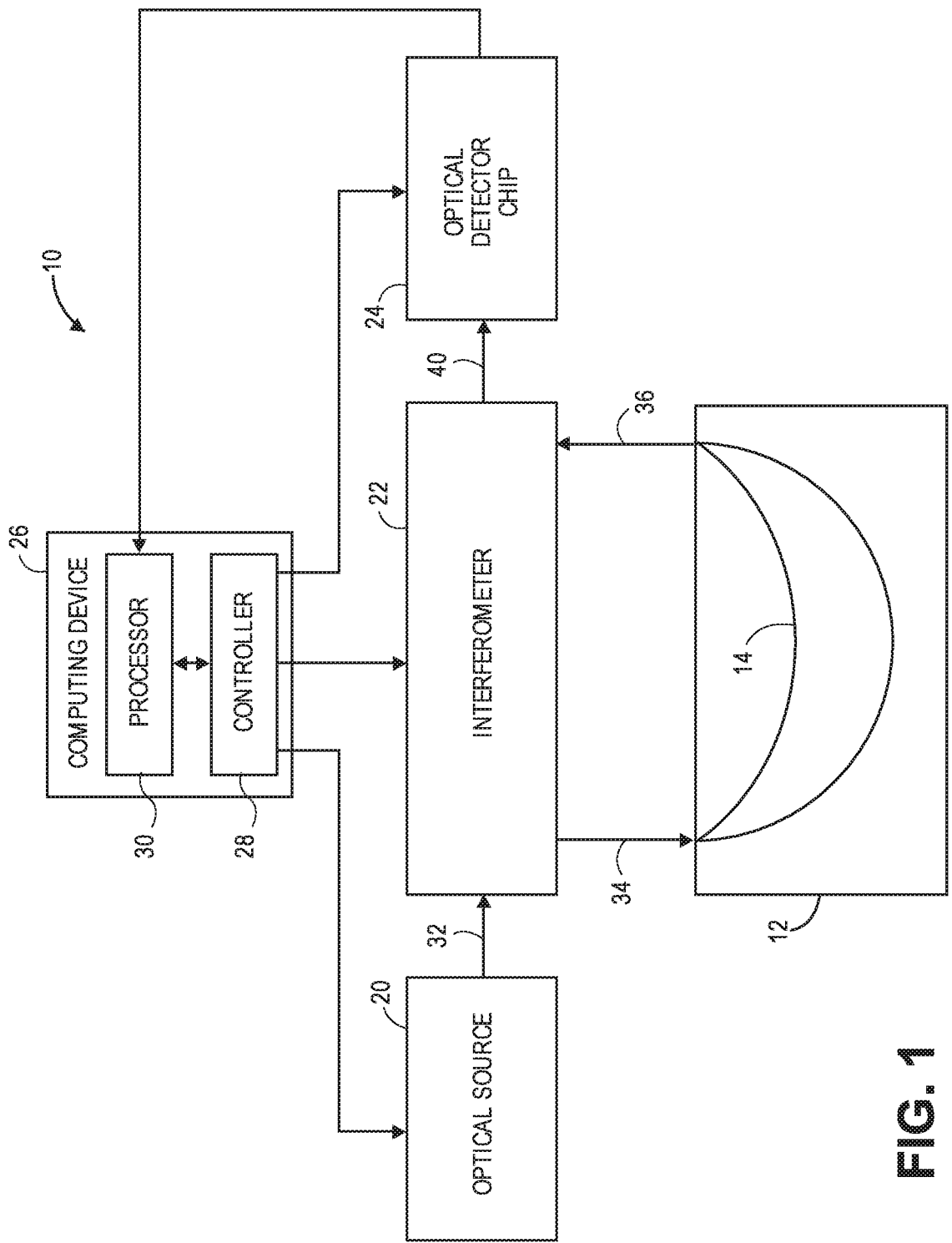
FIG. 1 is a block diagram of a non-invasive optical detection system constructed in accordance with one embodiment of the present inventions.

Referring now to FIG. 1, a generalized embodiment of an optical detection system 10 constructed in accordance with the present inventions will now be described. The non-invasive optical detection system 10 is configured for acquiring signal light in a sample 12, processing the signal light, and determining a characteristic of the sample 12 based on the processed signal light. In the illustrated embodiment, the sample 12 is an anatomical structure, and as such, the non-invasive optical detection system 10 is configured for non-invasively acquiring physiologically-encoded signal light (i.e., signal light representative of a physiologically-dependent optical signal) in the anatomical structure 12, processing the physiologically-encoded signal light, and determining the presence and depth of the physiologically-dependent optical signal in the anatomical structure 12 based on the processed physiologically-encoded signal light.

In the illustrated embodiment, the anatomical structure 12 is a brain, in which case, the non-invasive optical detection system 10 may be further configured for identifying the presence and location of neural activity within the brain 12 based on the physiologically-dependent optical signal. Although for exemplary purposes, the non-invasive optical detection system 10 is described as acquiring physiologically-encoded information from brain tissue, variations of such optical detection system 10 may be used to acquire physiologically-encoded information from other anatomical structures of a human body, animal body and/or biological tissue.

In the illustrated embodiments, the physiologically-dependent optical signal may be a fast-optical signal (i.e., perturbations in the optical properties of neural tissue caused by mechanisms related to the depolarization of neural tissue, including, but not limited to, cell swelling, cell volume change, changes in membrane potential, changes in membrane geometry, ion redistribution, birefringence changes, etc.), or the physiologically-dependent optical signal may be a slower hemodynamic change, e.g., Doppler shift due to moving blood flow, changes in blood volume, metabolism variations such a blood oxygen changes. However, as will be described in further detail below, the non-invasive optical detection system 10, when properly tuned to a specific type of physiologically-dependent optical signal, is capable of decoding light propagating through the brain to detect any signal that causes a change in an optical property of the brain 12.

The neural activity information (or the acquired physiologically-encoded information from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, vehicle's audio systems, vehicle's autonomous driving systems, etc., and/or may be used internally to adjust the detection parameters of the non-invasive optical measurement system 10, such as increasing or decreasing the strength of the optical source and/or data compression and/or analysis, such a Fast Fourier Transform (FFT) and/or statistical analysis.

Although the non-invasive optical detection system 10, for purposes of brevity, is described herein as acquiring physiologically-encoded information from the brain 12 by using a single fixed source/detector-array pair arrangement to create one bundle of detected optical paths 14 through the brain 12 in a single measurement period, in a practical implementation capable of detecting and localizing the physiologically-dependent optical signal in an x-y plane along the surface of the brain 12, variations of the non-invasive optical detection system 10 may utilize more complex source-detector arrangements (e.g., single-source multi-detector, multi-source single-detector, or multi-source multi-detector) to simultaneously create multiple optical path bundles 14 spatially separated from each other within the brain 12 in a single measurement period, or may utilize a movable source-detector arrangement to sequentially create multiple optical path bundles 14 over several measurement periods, as described in U.S. Provisional Patent Application Ser. No. 62/692,074, entitled "Frequency Domain Optical Spectroscopy For Neural Decoding," and U.S. Provisional Patent Application Ser. No. 62/692,124, entitled "Interferometric Frequency-Swept Source and Detector in a Photonic Integrated Circuit," which are expressly incorporated herein by reference. Thus, in a practical implementation, the non-invasive optical detection system 10 may detect and localize physiologically-dependent optical signals associated with neural activity in the brain, including fast-optical signals, in three-dimensions, with two of the dimensions represented as an x-y plane spanning the surface of the brain 12 encoded within the spatially separated multiple sample paths and the third dimension (z-dimension or depth into the brain 12) being encoded within frequency components of photons propagating along the sample paths.

Referring still to FIG. 1, the non-invasive optical detection system 10 generally comprises an optical source 20, an interferometer 22, at least one multi-channel optical detector chip 24 (only one is shown in FIG. 1, although several may be used in a typical embodiment, e.g., in a complex source-detector arrangement), and a computing device or other similar device 26, which all operate together to non-invasively detect the presence and depth of a physiologically-dependent optical signal in the brain 12.

The computing device 26 comprises a controller 28, a processor 30, a memory (not shown), a display (not shown), and an input device (not shown). The computing device 26 can, e.g., be a computer, tablet, mobile device, or any other suitable device for processing information. The computing device 26 can be local to the user or can include components that are non-local to the user. For example, in at least some embodiments, the user may operate a terminal that is connected to a non-local computing device. In other embodiments, the memory can be non-local to the user. The computing device 26 can utilize any suitable processor 30, including one or more hardware processors that may be local to the user or non-local to the user or other components of the computing device 26. The processor 30 is configured to execute instructions provided to the processor 30, as described below.

Any suitable memory can be used for the computing device 26. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 26, such as a tablet, smart phone, or smart watch. The input device can be, for example, a keyboard, mouse, touch screen, track ball, joystick, voice recognition system, or any combination thereof, or the like.

Although the controller 28 and processor 30 are described herein as being separate components, it should be appreciated that portions or all functionality of the controller 28 and processor 30 may be performed by a single component. Furthermore, although all of the functionality of the controller 28 is described herein as being performed by a single component, and likewise all of the functionality of the processor 30 is described herein as being performed by a single component, such functionality each of the controller 28 and the processor 30 may be distributed amongst several components. It should also be appreciated that all or a portion of the controller 28 may be located outside of a physical computing device, e.g., as a Field Programmable Gate Array (FPGA). Moreover, it should be appreciated that those skilled in the art are familiar with the terms "controller" and "processor," and that they may be implemented in software, firmware, hardware, or any suitable combination thereof.

The optical source 20 may take the form of a distributed feedback (DFB) laser, although other light sources, e.g., highly coherent vertical cavity surface emitting laser (VCSEL), distributed Bragg reflector (DBR) laser, a Fourier domain mode locked (FDML) laser, a super luminescent diode (SLD), a light emitting diode (LED), a diode-pumped solid-state (DPSS) laser, a laser diode (LD), a titanium sapphire laser, a micro light emitting diode (mLED), or similar laser to achieve long enough coherence length and high amplitude stability, among other optical sources, may be used.

The optical source 20 may have either a predefined coherence length or a variable coherence length. Since the goal of the non-invasive optical detection system 10 is to measure optical and dynamic properties at deeper depths within brain tissue, as opposed to acquiring images of the brain tissue at a shallow depths by using conventional OCT systems, the optical source 20 preferably has an instantaneous spectral linewidth and tuning range narrower by several orders of magnitude than in typical OCT systems, enabling the measurement of distinctly longer optical pathlengths (of up to tens of centimeters) at the cost of reduced resolution (of the order of millimeters). Preferably, the optical source 30 has a coherence length of at least 5 cm, an instantaneous spectral linewidth of less than 2 nm, and preferably less than 0.5 nm, and a tuning range of the wavelength greater than 3 pm, and preferably greater than 30 pm.

The optical source 20 is configured for generating source light 32, which may, e.g., be ultraviolet (UV) light, visible light, and/or near-infrared and infrared light, and may have any suitable wavelength, e.g., in the range of 350 nm-1800 nm. The source light 32 may be close to monochromatic in nature, comprising approximately a single-wavelength light, or the source light 32 may have multiple wavelengths (e.g., white light). It is preferred that the optical wavelength of the source light 32 be selected to maximize sensitivity to the specific physiologically-dependent optical signal of interest. For example, in the case where the physiologically-dependent optical signal of interest is a fast-optical signal, an optical wavelength greater than hemoglobin absorption wavelengths (e.g., greater than 850 nm) may be used for the source light 32 to detect scattering changes by materials other than blood, and/or to detect scattering by blood outside of wavelengths that are strongly absorbed by blood. Optionally, an optical wavelength equal to or greater than 1000 nm may be used for the source light 32 to maximize penetration. In the case where the physiologically-dependent optical signal of interest is a hemodynamic optical signal (e.g., blood oxygen concentration), an optical wavelength in the range of 550 nm to 850 nm may be used for the source light 32. Multiple optical wavelengths can be used for the source light 32 to allow different physiologically-dependent optical signals to be distinguished from each other. For example, source light 32 having two optical wavelengths of 900 nm and 700 nm can be respectively used to resolve fast-optical signals and blood oxygenation. Alternatively, the wavelength of the source light 32 can be selected to maximize the sensitivity of the multi-channel optical detector chip 24.

The source light 32 generated by the optical source 20 has a range of optical wavelengths. In the illustrated embodiment, the source light 32 has a narrow optical spectrum, and the optical source 20, under control of the controller 28 (shown in FIG. 1), rapidly sweeps (or "chirps") the source light 32 over the range of optical wavelengths as a function of time to functionally mimic or create an effective broad optical spectrum. In this manner, depth information is encoded into the resulting signal light, as will be described in further detail below. Alternatively, instead of sweeping the source light 32, the optical source 20 may output source light 32 having a broad optical bandwidth of, e.g., 10 pm to 1 nm.

The optical source 20 may receive input current from a drive circuit (not shown), e.g., a laser diode current driver, that can be varied to sweep the source light 32 output by the optical source 20. As briefly discussed above, a DFB laser may be used for the optical source 20. The DFB laser comprises an optical cavity having a diffraction grating that serves as a wavelength selective element and provides optical feedback that reflects light back into the cavity to form the resonator. The grating is constructed so as to reflect only a narrowband of wavelengths, and thus produce a single longitudinal lasing mode. Altering the temperature of the DFB laser causes the pitch of the grating to change due to the dependence of refractive index on temperature, thereby altering the wavelength of the output, thereby making the DFB laser tunable on the order of 6 nm for a 50° K change in temperature. Altering the current powering the DFB laser causes a temperature change inside of the DFB laser, thereby allowing it to be tuned in a controlled manner. In one exemplary embodiment, the central wavelength of the DFB laser may be in the range of 600 nm-900 nm with a tunable frequency of 10 GHz and the frequency of the DFB laser may be swept at a repetition as small as 10 μs (i.e., a 100 KHz chirp repetition rate).

The sweep rate of the optical source 20 defines a measurement period of the non-invasive optical detection system 10 in accordance with the equation:

$$t = 1/R, \quad [1]$$

where t is the measurement period, and R is the uni-directional rate (forward sweep or reverse sweep).

Figure 2:
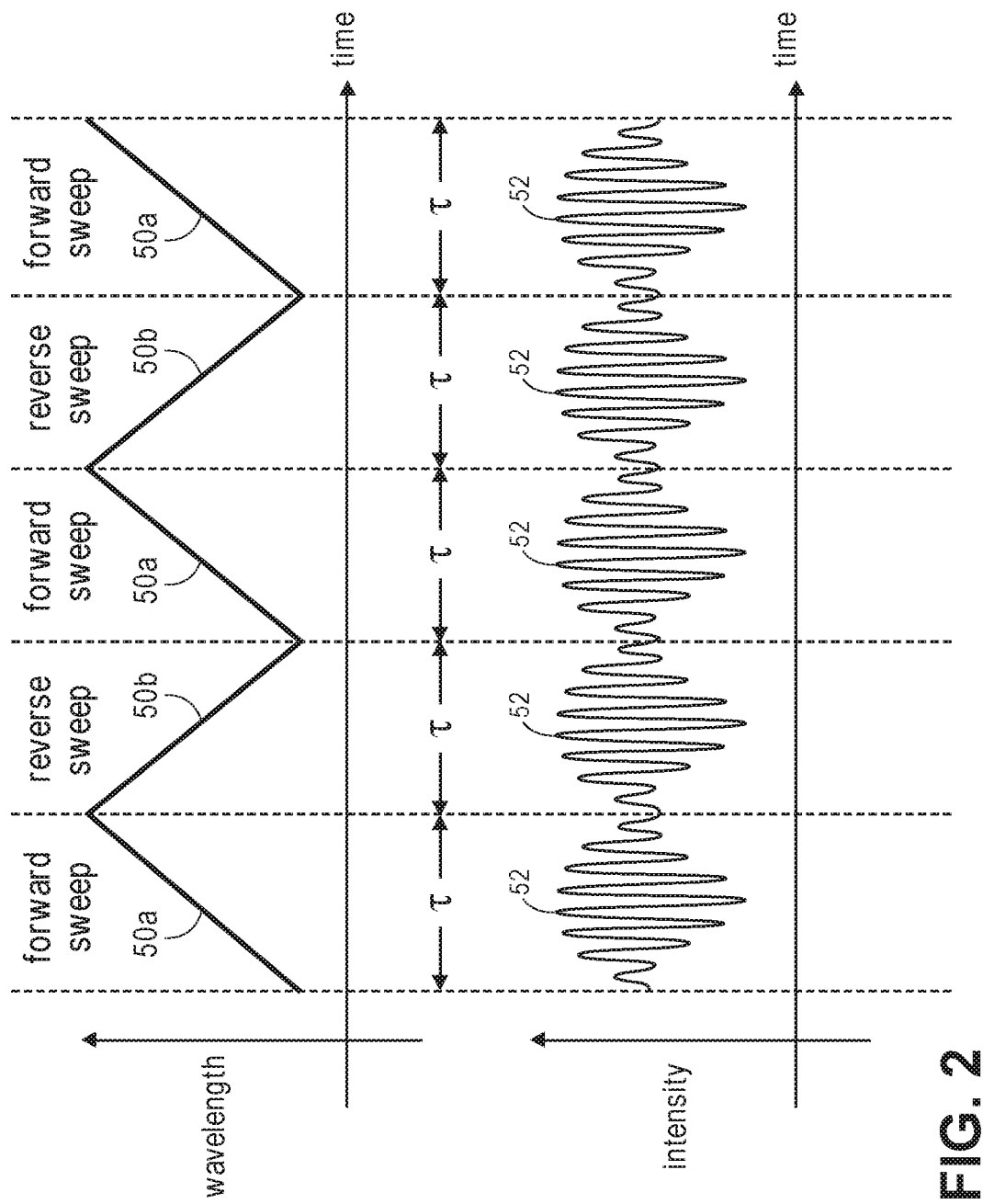
FIG. 2 is a timing diagram illustrating the optical sweeps performed by the non-invasive optical detection system of FIG. 1, and fringe patterns in interference light patterns resulting from the optical sweeps.

As illustrated in FIG. 2, the optical source 20 sweeps across a range of optical wavelengths during the measurement period t. In the illustrated embodiment, the measurement periods t are respectively defined by both forward sweeps 50a (low to high wavenumbers) and rearward sweeps 50b (high to low wave numbers) of the optical source 20, thereby maximizing the usage of the full sweep range of the optical source 20. However, in alternative embodiments, all of the measurement periods t are defined by either forward sweeps 50a or reverse sweeps 50b (but not both), such that there are idle time intervals between sequential measurement periods t equal to the time period of a unilateral sweep R. However, because the data throughput is generally limited by the detection and processing scheme, the existence of the idle time intervals between the measurement periods t will generally not limit the data throughput of the non-invasive optical detection system 10.

Notwithstanding this, the uni-directional sweep rate R of the optical source 20 may be any suitable rate, but preferably, defines a measurement period t that is no longer than the duration of the signal of interest, and furthermore, is no longer than the speckle decorrelation time (which is due to the scatterers' motion inside tissue, and rapidly decreases with the depth of the tissue, and in particular, scales super-linearly with the depth into tissue, falling to microseconds or below as the tissue depth extends to the multi-centimeter range) of brain tissue. For example, the measurement period t may be equal to or less than 100 μs (equivalent to a uni-directional sweep rate of 10 KHz), and preferably equal to or less than 10 μs (equivalent to a uni-directional sweep rate of 100 KHz).

The interferometer 22 is a Mach-Zehnder-type interferometer that is configured for splitting the source light 32 from the optical source 20 into sample light 34, which is delivered to the brain 12 along a sample arm and exits the brain 12 as physiologically-encoded signal light 36, and reference light 38 (shown in FIG. 3), which propagates along a reference arm outside of the brain 12. The interferometer 22 is further configured for combining the physiologically-encoded signal light 36 with the reference light 38 to create an interference light pattern 40 corresponding to the optical modes of the physiologically-encoded signal light 36, and oscillation frequency components corresponding to different optical pathlengths of the sample light 34 propagating through the brain 12, which in turn correspond to different depths in the brain 12. In the illustrated embodiment, the interference light pattern 40 takes the form of an interference light speckle pattern having a plurality of optical modes (or speckle grains).

Figure 3:
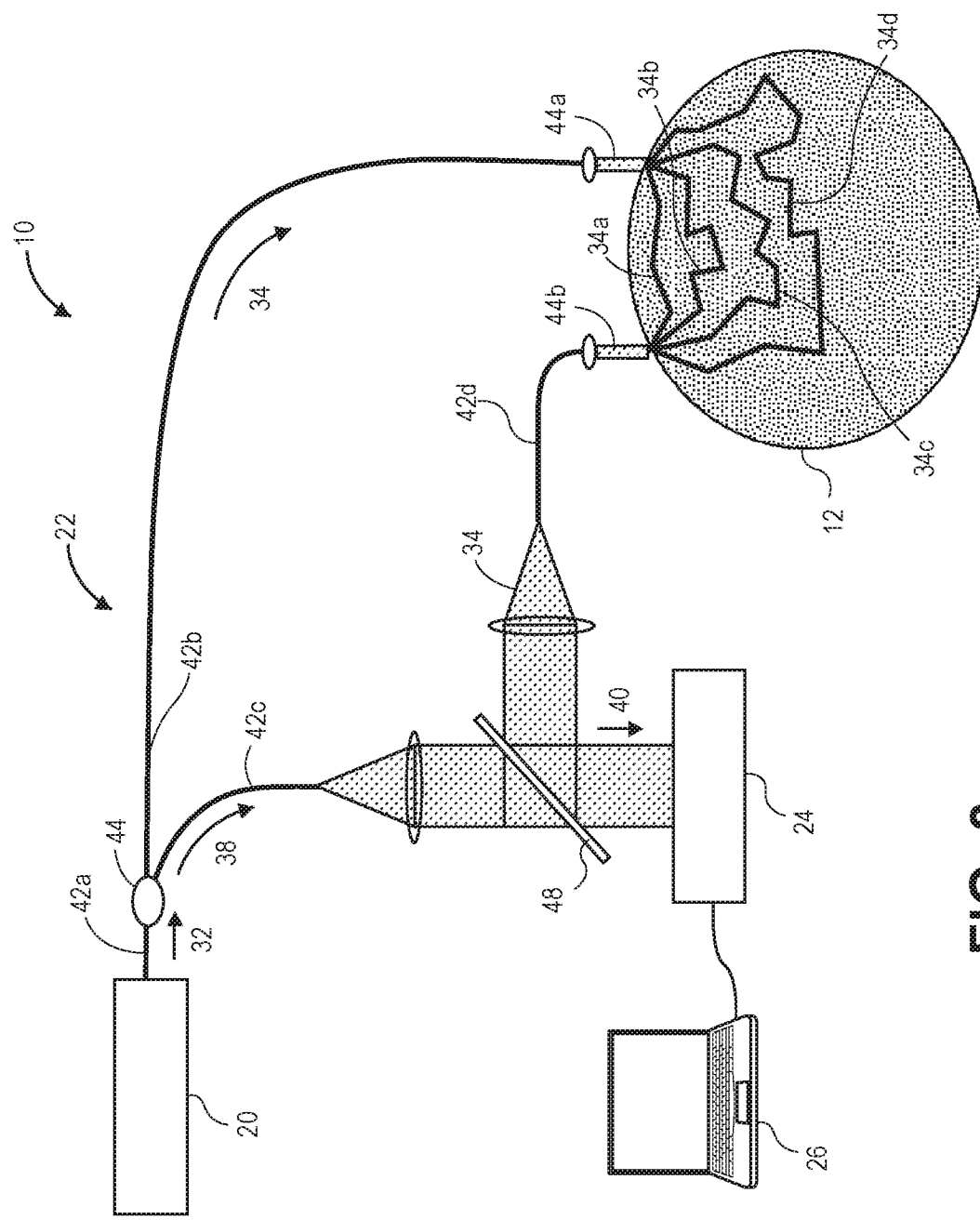
FIG. 3 is a plan view of one embodiment of an interferometer used in the non-invasive optical detection system of FIG. 1.

Referring to FIG. 3, a more detailed implementation of the interferometer 22 in the context of the non-invasive optical detection system 10 will now be described. In this implementation, the interferometer 22 is optical fiber-based (i.e., uses optical fibers to direct light between the components), although in alternative embodiments, the interferometer 22 may direct light via free-space propagation between the components using optics, such as mirrors, as further illustrated in U.S. patent application Ser. No. 16/266,818, entitled "Ultrasound Modulating Optical Tomography Using Reduced Laser Pulsed Duration," U.S. patent Ser. No. 16/299,067, entitled "Non-Invasive Optical Detection Systems and Methods in Highly Scattering Medium," and U.S. patent application Ser. No. 16/382,461, entitled "Non-Invasive Optical Detection System and Method," which are expressly incorporated herein by reference.

The interferometer 22 comprises an input optical fiber 42a that optically couples the interferometer 22 to the optical source 20 for receiving the source light 32 from the optical source 20. The interferometer 22 further comprises an optical fiber-based optical beam splitter 44 for splitting the source light 32 into the sample light 34 and the reference light 38. The optical beam splitter 44 may not necessarily split the source light 32 equally into the sample light 34 and the reference light 38, and it may actually be more beneficial for the optical beam splitter 44 to split the source light 32 unevenly, such that the intensity of the sample light 34 is less than the intensity of the reference light 38 (e.g., 99/1 power ratio), since much of the sample light 34 will be lost after passing through the head. That is, the intensity of the sample light 34 should be boosted relative to the reference light 38 to compensate for the losses incurred by the sample light 34 as it passes through the head and the fact that only a small portion of signal light (described below) exiting the head will be detected.

The interferometer 22 further comprises a sample arm optical fiber 42b and a reference arm optical fiber 42c for respectively propagating the sample light 34 and the reference light 38 along the sample arm and the reference arm of the interferometer 22. The sample arm optical fiber 42b delivers the sample light 34 via an output port 46a into the brain 12, such that the sample light 34 scatters diffusively through the brain 12, and back out again, exiting as the physiologically-encoded signal light 36. As the sample light 34 scatters diffusively through the brain 12, various portions 34a-34d of the sample light 34 will take different paths through the brain 12, which combine into the exiting physiologically-encoded signal light 36. For purposes of brevity, only four sample light portions 34a-34d are illustrated as traveling along optical paths of different lengths (from shallow to deep), which combined into the exiting neural-encoded signal light 36, although it should be appreciated that the diffused sample light 34 will travel along many more optical paths through the brain 12. As the sample light 34 interacts with the brain 12, multiple optical modes develop and appear in the physiologically-encoded signal light 36 as speckle grains.

The interferometer 22 further comprises an output optical fiber 42d configured for receiving the physiologically-encoded signal light 36 from the brain 12 via an input port 46b. To maintain the multiple optical modes of the physiologically-encoded signal light 36 received from the brain 12 via the input port 44b, the output optical fiber 42d is a multi-mode output optical fiber. The sample arm optical fiber 42b may also comprise a multi-mode optical fibers and/or single-mode optical fiber bundle, whereas the input optical fiber 42a and the reference arm optical fiber 42c are preferably single-mode optical fibers.

The interferometer 22 further comprises a single optical beam combiner 48 configured for receiving the physiologically-encoded signal light 36 from the output optical fiber 42d, receiving the reference light 38 from the reference arm optical fiber 42c, and combining the physiologically-encoded signal light 36 and the reference light 38 via superposition to generate the interference light pattern 40. In the illustrated embodiment, the optical beam combiner 48 is a free-space optical beam combiner that respectively receives the physiologically-encoded signal light 36 and the reference light 38 on different faces of the optical beam combiner 48 and outputs the interference light pattern 40 on another different face of the optical beam combiner 48. In this case, collimators (not shown) can be located between the optical beam combiner 48 and the output optical fiber 42d and reference arm optical fiber 42c to collimate the physiologically-encoded signal light 36 and the reference light 38 at the respective faces of the optical beam combiner 48.

As discussed above, the optical source 20, in the illustrated embodiment, sweeps the source light 32 over a range of optical wavelengths, such that depth information is encoded within the physiologically-encoded signal light 36. In effect, the resulting physiologically-encoded signal light 36 exiting the brain 12 will have a time-of-flight (TOF) profile encoded with different optical pathlengths L (or depths in the brain 12) in accordance with the equation:

$$\frac{L}{c}n_r,$$

where c is the speed of light and $n_r$ is the refractive index of tissue).

Figure 4A:
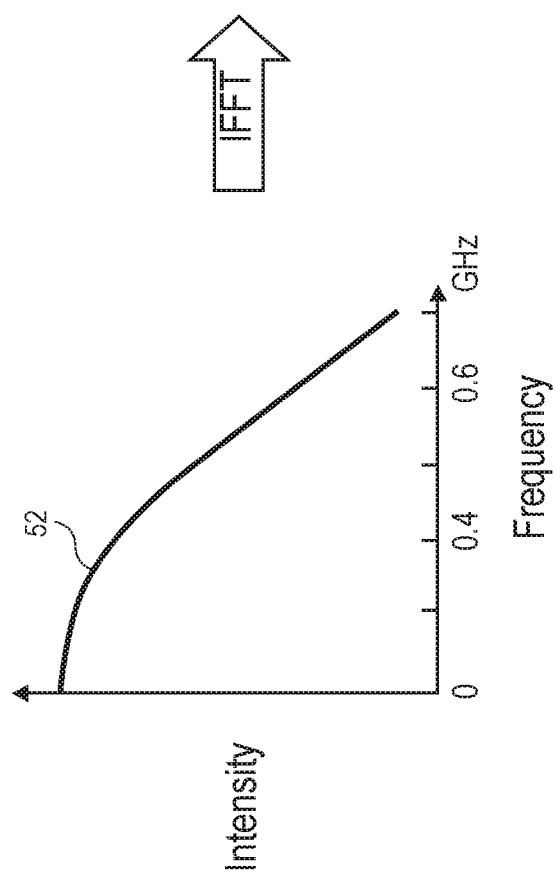
FIG. 4A is a diagram illustrating an exemplary frequency component-intensity profile detected by the non-invasive optical detection system of FIG. 1.
Figure 4B:
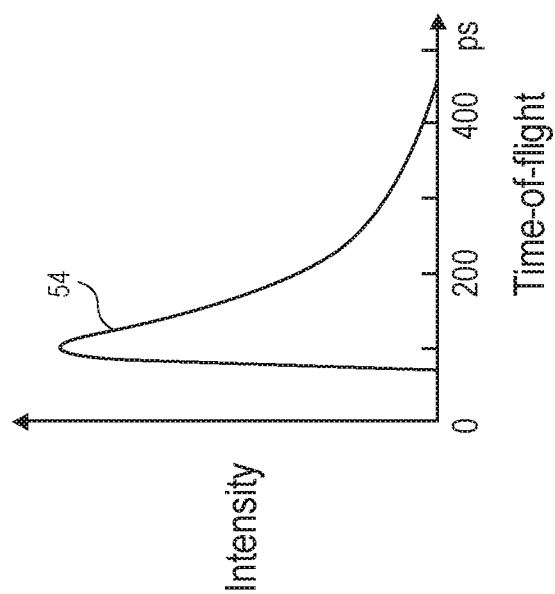
FIG. 4B is a diagram illustrating an exemplary time-of-flight (TOF)-intensity profile transformed from the frequency component-intensity profile of FIG. 4A.

In particular, as a result of sweeping the source light 32 over a range of optical wavelengths, the physiologically-encoded signal light 36 has a frequency component-intensity profile 52, as illustrated in FIG. 4A, which corresponds to a time-of-flight (TOF)-intensity profile 54, as illustrated in FIG. 4B. As shown in FIGS. 5A and 5B, this frequency component-intensity profile 52 comprising intensity values of the oscillation frequency components 56, which are encoded with optical pathlength information, and thus, different depths of the brain 12. It follows from this that a relatively shallow optical path will yield a relatively slow oscillation frequency component 56a (see FIG. 5A), whereas a relatively deep optical path will yield a relatively fast oscillation frequency component 56b (see FIG. 5B). As one example, four exemplary oscillation frequency components f1-f4 (see FIG. 6A) respectively correspond to four exemplary intensities of the light at four different optical pathlengths L1-L4 (see FIG. 6B) which directly correlate to depths of the physiologically-dependent optical signal within the brain 12).

The multi-channel optical detector chip 24 may be implemented as a camera with a frame rate that can be controlled by the controller 28 in coordination with the optical wavelength sweeps of the optical source 20 to match the measurement period t. Significantly, the multi-channel optical detector chip 24 is a compact, low-power chip that comprises a very large number (thousands to hundreds of thousands) of parallel independent channels. Each channel of the multi-channel optical detector chip 24 may monitor a different subset of optical modes of the interference light pattern 40, and thus the physiologically-encoded signal light 36 (i.e., speckle grain), thereby enabling many different subsets of optical modes of the interference light pattern 40 (i.e., many speckle grains) to be measured in parallel. In one embodiment, the multi-channel optical detector chip 24 is affixed directly to the face of the optical beam combiner 48 from which the interference light pattern 40 exits.

As shown in FIG. 7, the multi-channel optical detector chip 24 comprises an array of pixels 60 (e.g., 100×100 pixels) configured for simultaneously detecting the different subsets of the optical modes of the interference light pattern 40, and outputting an array of intensity values I respectively of the different subsets of optical modes of the interference light pattern 40 during each measurement period t. In the case where the interference light pattern 40 is a speckle light pattern, the optical modes are speckle grains (approximately the size of a wavelength of the light) of the speckle light pattern 40. The multi-channel optical detector chip 24 may be implemented using any suitable technology, e.g., CMOS technology. Each pixel 60 is preferably very small, e.g., 100 μm×100 μm, thereby minimizing the size and power consumption of the multi-channel optical detector chip 24. The multi-channel optical detector chip 24 may have less than 100% fill-factor (e.g., 50% fill-factor), e.g., the optical detection region and the electronics may be in a side-by-side configuration for each pixel, or may have 100% fill-factor, e.g., the optical detection region and the electronics may be in a stacked configuration for each pixel.

In general, if the number of optical modes detected by the multi-channel optical detector chip 24 is N, the multi-channel optical detector chip 24 will have an N/M number of channels, wherein M is number of optical modes of the interference light pattern 40 detected by a single pixel 60 of the multi-channel optical detector chip 24. In the case where the multi-channel optical detector chip 24 employs some form of balanced detection, e.g., conventional fully balanced detection, or partial balanced detection, as described in U.S. Provisional Patent Application Ser. No. 62/834,505, entitled "Partially Balanced Interferometric Parallel Detection," which is expressly incorporated herein by reference, if the number of optical modes detected by the multi-channel optical detector chip 24 is N, the number of channels of the multi-channel optical detector chip 24 will be reduced by a factor of 2, i.e., the number of channels of the multi-channel optical detector chip 24 will be N/2M.

It should be appreciated that having a multi-channel optical detector chip 24 has two significant advantages.

First, the use of a large number of independent channels detects the interference light pattern 40 derived from an area of the brain 12, as opposed to a single point of the brain 12, which increases the spatial resolution of the multi-channel optical detector chip 24, thereby allowing for better identification and classification of neural activity in the brain 12, and eventually a higher probability of detecting certain neural activity in the brain 12 with higher confidence.

Second, the overall sensitivity of the optical signal detection increases with the number of independent channels of the multi-channel optical detector chip 24 in accordance with $\sqrt{N}$, where N is the number of independent channels. Thus, the use of a large number of pixels 60 in the multi-channel optical detector chip 24 ultimately increases the SNR of the detected interference light pattern 40 relative to a conventional iNIRS system that uses a single large detector.

That is, in the case where a single detector was used in the conventional iNIRS system, the use of only one channel for detection, results in the averaging of all of the optical modes of the interference light pattern 40 during each measurement period t, and hence destructive interference that limits the detected signal magnitude. In contrast, the use of multiple-channel detection allows the pixels 60 to respectively detect subsets of optical modes of the interference light pattern 40 during each measurement period t, with the accompanying advantage of boosting light collection efficiency, maximizing the number of photons collected without destructive averaging, and leading to higher SNR.

Because the physiologically-encoded signal light 36 includes many optical pathlengths that correspond to the depths at which the sample light portions 34a-34d of the sample light 34 traverse the brain 12 (see FIG. 2), the resulting interference light pattern 40 is a high-frequency bandwidth signal that would typically require a tremendous amount of processing power and power consumption to extract the relevant signal from the interference light pattern 40 over many independent channels if digitally performed. However, in order to achieve a large number of parallel channels with a relatively small processing power small power consumption (e.g., less than 100s of mW), the multi-channel optical detector chip 24 takes advantage of the fact that changes in physiologically-dependent optical signals typically occur at much slower speeds (e.g., in the KHz range) than the oscillation frequency components in the raw physiologically-encoded signal light 36 (e.g., in the MHz range).

The multi-channel optical detector chip 24 performs high-frequency bandwidth processing steps of the interference light pattern 40 for all of the channels in the analog domain to extract this slow time-varying information (i.e., at least one characteristic) from the interference light pattern 40 first, in effect compressing the high-bandwidth, information poor, interference light pattern 40 into low-bandwidth, information rich, data with minimal power consumption (representing the characteristic(s)). For example, if there are 1000 optical pathlengths (depths) of interest (although in practice, the number of optical pathlengths requires will be much less, e.g., 3 or 4), the bandwidth of the resulting low-bandwidth information will be approximately 1000 times less than the bandwidth of the raw interference light pattern 40. This low-bandwidth information for all of the channels can then be digitized for further processing by the processor 30 to determine the presence and depth of a change in a physiologically-dependent optical signal (e.g., a fast-optical signal or hemodynamic changes), and thus the neural activity, within the brain 12. To facilitate data compression, the multi-channel optical detector chip 24 also sequentially selects each oscillation frequency component (e.g., oscillation frequency components f1-f4 illustrated in FIG. 6A), such that the processor 30 may analyze one optical pathlength (depth) (e.g., optical pathlengths L1-L4 in FIG. 6B) at a time. For example, if the number of channels is equal to 1000, and the optical pathlengths to be analyzed is 50, the rate of the digital information output by the optical chip 24 may be approximately 400 Mbit/sec, assuming 1000 frames of second and an 8-bit data value.

Further details on several embodiments of the multi-channel optical detector chip 24 will be described in further detail below.

The processor 30 may determine the presence and depth of a change in a physiologically-dependent optical signal (e.g., a fast-optical signal or hemodynamic changes), and thus the neural activity, within the brain 12, based on the low-bandwidth information received from the multi-channel optical detector chip 24 using any one of a variety of techniques. In each technique, the processor 30 is configured for acquiring at least one array of extracted characteristics from the pixels 60 of the multi-channel optical detector chip 24 (i.e., over all of the channels) for the selected current optical pathlength of interest during at least one of the measurement periods t, reducing each array of extracted characteristics to a single characteristic (e.g., by computing a mean of array of characteristics), and determining the presence and depth (correlated to the selected optical pathlength L1-L4) of any change in the physiologically-dependent optical signal, at least partially, based on the reduced characteristic.

In one embodiment, the processor 30 determines the presence and depth of a change in a physiologically-dependent optical signal within the brain 12, e.g., by comparing the current TOF-intensity profile 54 of the physiologically-encoded signal light 36 (see FIG. 4B) (in this case, the reduced oscillation frequency component intensity value) with a user-specific baseline TOF-intensity profile (e.g., a previously acquired TOF-intensity profile 54) (in this case, a previously reduced oscillation frequency component intensity value).

Significantly, there is a strong correlation between the depth of penetration of photons of the sample light 34 within the brain 12 and the shape of the waveform of the detected physiologically-encoded signal light 36 in the time domain. That is, the TOF-intensity profile 54 can be correlated to spatial depth information (i.e., the tail end of the TOF-intensity profile 54 contains relatively deep information, whereas the front end of the TOF-intensity profile 54 contains relatively shallow information), and thus, the spatial depth of a change in a physiologically-dependent optical signal in the brain 12 may be determined. That is, it is known that the occurrence of the physiologically-dependent optical signal in the brain 12 will perturb the photons of the sample light 34 at the depth of the physiologically-dependent optical signal in the brain 12, thereby changing the intensity of the photons of the sample light 34 having an optical pathlength corresponding to that depth.

For example, as further illustrated in FIGS. 8A and 8B, a relatively early time-bin 54a of the TOF-intensity profile 54 is weighted for photons that travel a relatively short distance along the detected optical path bundle 14 in the brain 12; that is, photons 58a that penetrate superficially into the brain 12; a later time-bin 54b of the TOF-intensity profile 54 is weighted for photons that travel a relatively medial distance along the detected optical path bundle 14 in the brain 12; that is, photons 58b that penetrate further into the brain 12; and an even later time-bin 54c of the TOF-intensity profile 54 is weighted for photons that travel a maximum distance along the detected optical path bundle 14 in the brain 12; that is, photons 58c that penetrate even further into the brain 12.

Thus, it can be appreciated that the TOF-intensity profile 54 of the detected signal light 36 contains intensity-optical pathlength information in which the spatial depth of a physiologically-encoded optical signal is encoded, and thus, a physiologically-encoded optical signal that changes at a certain depth in the brain 12 will cause a corresponding perturbation in the TOF-intensity profile 54. For example, as shown in FIG. 8A, there exists a perturbation between the baseline TOF-intensity profile 54 before a change in the physiologically-dependent optical signal, and a TOF-intensity profile 54' when the physiologically-dependent optical signal has changed. The change in the physiologically-dependent optical signal has a measurable perturbation in the TOF-intensity profile 54 in time-bins 54b and 54c, indicating a change in scattering or absorption in the photons in the mid-level or maximum depth in the brain 12, and thus, a change in the physiologically-dependent optical signal at this depth in the brain 12.

In another embodiment, the processor 30 determines the presence and depth of a change in a physiologically-dependent optical signal (e.g., a fast-optical signal or hemodynamic changes), and thus the neural activity, within the brain 12, e.g., by performing diffuse correlation spectroscopy (DCS) using an autocorrelation technique to determine the decorrelation speed of the time-lapsed complex field of the physiologically-encoded signal light 36 (in this case, the reduced oscillation frequency component intensity value)

Figure 9A:
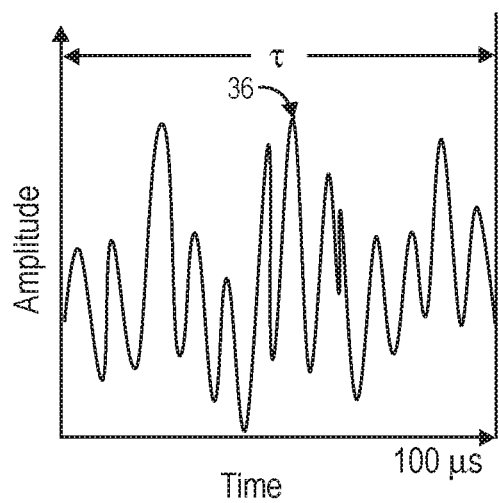
FIG. 9A is a timing diagram of an exemplary amplitude of physiologically-encoded signal light resulting in the delivery of sample light into an anatomical structure by the optical measurement system of FIG. 1.
Figure 9B:
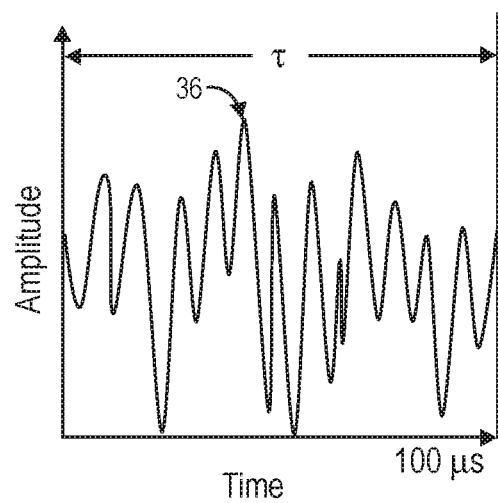
FIG. 9B is a timing diagram of an exemplary phase of physiologically-encoded signal light resulting in the delivery of sample light into an anatomical structure by the optical measurement system of FIG. 1.
Figure 9C:
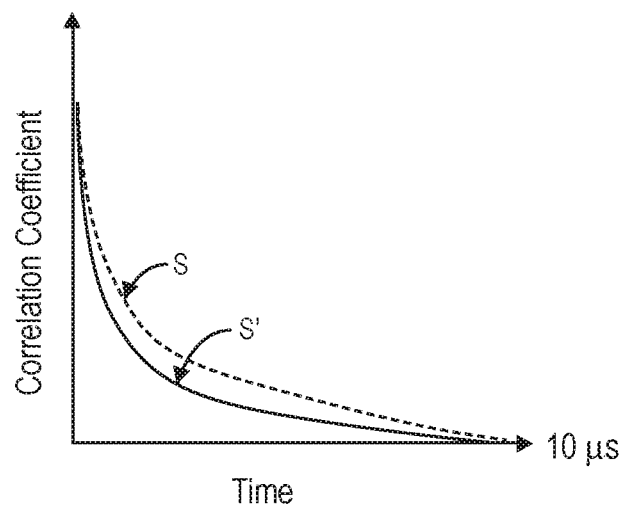
FIG. 9C is a timing diagram of exemplary decorrelation speeds of the physiologically-encoded signal light resulting in the delivery of sample light into an anatomical structure by the optical measurement system of FIG. 1.

One exemplary time-lapsed complex field of the physiologically-encoded signal light 36 in terms of intensity and phase is respectively plotted over a measurement period t of 100 μs, as illustrated in FIGS. 9A and 9B. As time lapses, the amplitude and phase of the physiologically-encoded signal light 36 fluctuates. The quicker the complex field of the physiologically-encoded signal light 36 fluctuates, the faster the physiologically-encoded signal light 36 decorrelates, and it is this decorrelation that the processor 30 measures in terms of decorrelation speed (i.e., the magnitude of decorrelation as a function of time). As illustrated in FIG. 9C, the decorrelation speed S indicates that the time-lapsed complex field of the physiologically-encoded signal light 36 decorrelates at an exponential rate, such that maximum correlation occurs at time=0, and complete decorrelation occurs at approximately time=10 μs.

Once the processor 30 obtains the decorrelation speed S of the time-lapsed complex field of the physiologically-encoded signal light 36, the processor 30 identifies a change in the physiologically-dependent optical signal in the brain 12, at least partially, by comparing the determined decorrelation speed of the complex field of the physiologically-encoded signal light 36 to a reference decorrelation speed. In one embodiment, the processor 30 identifies the physiologically-dependent optical signal, and thus the neural activity, at the depth in the brain 12, e.g., by comparing the current decorrelation speed S of the complex field of the physiologically-encoded signal light 36 with a predetermined baseline decorrelation speed or a user-specific baseline decorrelation speed S' (e.g., a previously determined decorrelation speed of the complex field of the physiologically-encoded signal light 36, as illustrated in FIG. 9C.

It can be appreciated that a fast-optical signal that occurs at the depth in the brain 12 of a user will increase the scattering of the physiologically-encoded signal light 36 at that depth, thereby increasing the decorrelation speed S of the physiologically-encoded signal light 36. Thus, a measurable change exists between the decorrelation speed S of the complex field of the physiologically-encoded signal light 36 in the presence of a change in the physiologically-dependent optical signal and the decorrelation speed S' of the complex field of the physiologically-encoded signal light 36 in the absence of a change in the physiologically-dependent optical signal, as illustrated in FIG. 9C.

Figure 10:
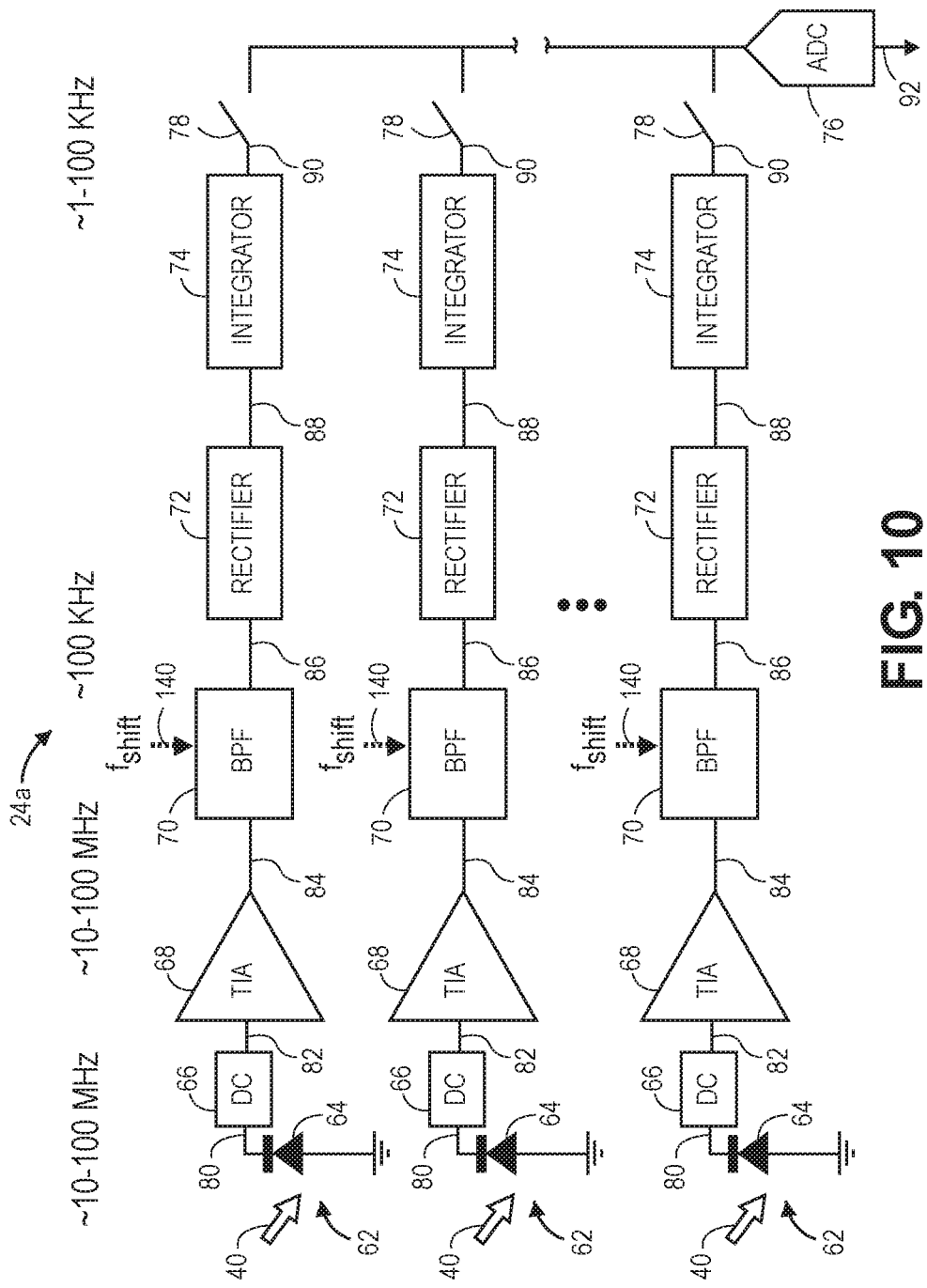
FIG. 10 is a block diagram of electronic componentry of one embodiment of an optical detector chip used in the optical measurement system of FIG. 1.

Referring now to FIG. 10, the electrical componentry of one embodiment of a multi-channel optical detector chip 24*a* will be described. The multi-channel optical detector chip 24*a* comprises a plurality of analog channels 62 corresponding to the number of pixels 60 (shown in FIG. 7). For example, for a 100×100 array of pixels, the number of analog channels 62 will be equal to 10,000 (or 5,000 if balanced detection is used). It should be noted that although FIG. 10 only illustrates the analog channels 62 corresponding to one dimension of the pixels 60 (e.g., one column), the series of analog channels 62 illustrated in FIG. 10 can be reproduced many times equal to the number of the other dimension of the analog channels 62 (e.g., the number of rows).

Each analog channel 62 of the multi-channel optical detector chip 24*a* comprises an optical detector 64 (shown as a photodiode, although other types of optical detectors are contemplated by the invention), which can be disposed on one side of the multi-channel optical detector chip 24*a*. In combination, the optical detectors 64 are arranged on one side of the multi-channel optical detector chip 24*a* in a two-dimensional array and correspond to the pixels 60 illustrated in FIG. 7.

Each optical detector 64 detects a subset of optical modes of the interference light pattern 40, and thus the physiologically-encoded signal light 36, and outputs a high-bandwidth analog signal 80 (see FIG. 12A) corresponding to the subset of optical mode of the interference light pattern 40. Each high-bandwidth analog signal 80 comprises averaging of the intensities of the corresponding subset of optical modes of the interference light pattern 40. Thus, in combination, the optical detectors 64 respectively detect different subsets of optical modes of the interference light pattern 40 respectively corresponding to the plurality of analog channels 62 of the multi-channel optical detector chip 24*a*.

Figure 12A:
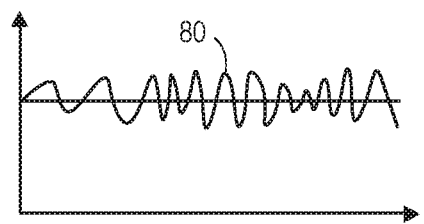
FIG. 12A is a diagram illustrating an exemplary high-bandwidth analog signal generated in the multi-channel optical detector chips of FIGS. 10 and 11.

It should be appreciated that, although it is preferred that each subset of optical modes of the interference light pattern 40 detected by an optical detector 64 comprise multiple spatially adjacent optical modes, each subset of optical modes of the interference light pattern 40 detected by an optical detector 64 may comprise a single (i.e., only one) optical mode. In any event, each optical detector 64 should be sized to detect at least one optical mode of the interference light pattern 40. As shown in FIG. 12A, each subset of optical modes of the interference light pattern 40 detected by the respective optical detector 64 has a large DC component and a very small, high frequency, AC component. Due to the sweeping of the optical source 20, the high-bandwidth analog signal 80 will generally have a high-bandwidth corresponding to the high-bandwidth of the physiologically-encoded signal light 36, e.g., in the range of 10 MHz-100 MHz, or even higher.

Figure 12D:
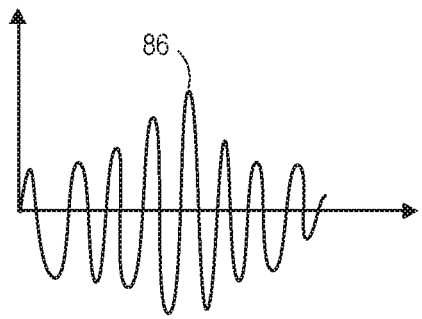
FIG. 12D is a diagram illustrating an exemplary pathlength-encoded analog signal generated in the multi-channel optical detector chips of FIGS. 10 and 11 after frequency filtering of the amplified AC analog signal.
Figure 12B:
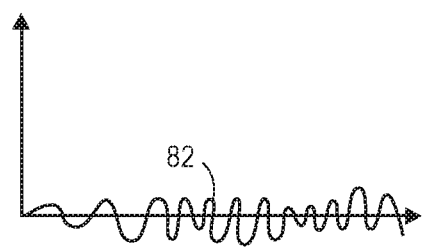
FIG. 12B is a diagram illustrating an exemplary alternating current (AC) analog signal generated in the multi-channel optical detector chips of FIGS. 10 and 11 after the removal of the direct current (DC) component of the high-bandwidth analog signal.

Each analog channel 62 of the multi-channel optical detector chip 24*a* further comprises a direct current (DC) removal element 66 coupled to the respective optical detector 64 for removing the DC component from the high-bandwidth analog signal 80, and outputting a purely AC analog signal 82 (i.e., an analog signal containing only AC frequency components) (see FIG. 12B). In the illustrated embodiment, each DC removal element 66 comprises conventional full-balanced detection circuitry, or partially-balanced detection circuitry, as described in U.S. Provisional Patent Application Ser. No. 62/834,505, entitled "Partially Balanced Interferometric Parallel Detection," which is expressly incorporated herein by reference, such that any electrical noise injected into the physiologically-encoded signal light 36 by the optical source 20 can be removed. In this case, each optical detector 64 represents a paired optical detector 64.

Figure 12E:
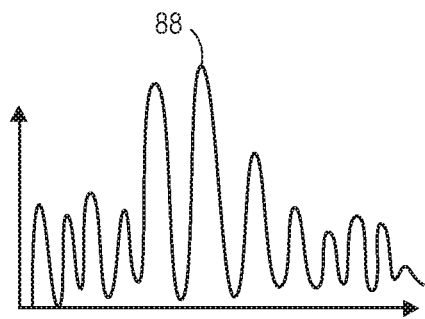
FIG. 12E is a diagram illustrating an exemplary rectified analog signal generated in the multi-channel optical detector chips of FIGS. 10 and 11 after rectification of the pathlength-encoded analog signal.
Figure 12C:
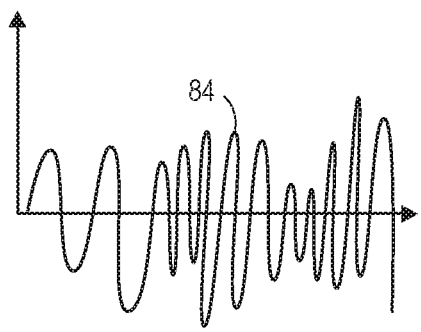
FIG. 12C is a diagram illustrating an exemplary amplified AC analog signal generated in the multi-channel optical detector chips of FIGS. 10 and 11 after amplification of the AC analog signal.

Each analog channel 62 of the multi-channel optical detector chip 24*a* further comprises an amplifier 68 coupled to the output of the respective DC removal element 66 for amplifying the AC analog signal 82, and outputting an amplified AC analog signal 84 (see FIG. 12C). In the illustrated embodiment, each amplifier 68 takes the form of a transimpedance amplifier (TIA), although other types of amplifiers are contemplated by the invention. Although the DC removal element 66 and amplifier 68 are illustrated and described as being separate components, it should be appreciated that a DC removal element and amplifier can be embodied in a single circuit that both amplifies and removes the DC component from the high-bandwidth analog signal 80 output by the respective optical detector (or paired optical detector) 64.

Significantly, the multi-channel optical detector chip 24*a* comprises analog compression circuitry configured for respectively extracting characteristics, and in this case, envelopes of each of the high-bandwidth analog signals 80 at the current optical pathlength of interest from the amplified AC analog signals 84, and outputting a plurality of low-bandwidth digital signals 92 respectively comprising digitally sampled versions of the extracted envelopes (i.e., each low-bandwidth digital signal 92 will be a digitally sampled version of the respective extracted envelope of the high-bandwidth analog signal 80 at the current optical pathlength of interest). The analog compression circuitry of the multi-channel optical detector chip 24*a* preferably has a relatively low bandwidth, e.g., below 100 MHz, and a dynamic range less than 30 dB.

To this end, each analog channel 62 of the multi-channel optical detector chip 24*a* further comprises a frequency filter assembly coupled to the output of the respective amplifier 68 for frequency filtering the amplified AC analog signal 84, and outputting a pathlength-encoded analog signal 86 (see FIG. 12D) corresponding to one of the optical pathlengths (i.e., an analog signal encoded with the current optical pathlength of interest (i.e., depth in the brain 12)), e.g., one of the optical pathlengths L1-L4. The bandwidth of the pathlength-encoded analog signal 86 output by the frequency filter assembly will be much lower than the bandwidth of the high-bandwidth analog signal 80 output by the respective optical detector 64, e.g., around 100 KHz.

In the embodiment illustrated in FIG. 10, the frequency filter assembly comprises a band-pass filter (BPF) 70 coupled to the output of the respective amplifier 68 for band-pass filtering the respective amplified AC analog signal 84, and outputting the respective pathlength-encoded analog signal 86 comprising a narrow band of oscillation frequency components having a center oscillation frequency component corresponding to the current optical pathlength of interest (e.g., one of the optical pathlengths L1-L4). For example, as illustrated in FIG. 13A, the BPF 70 may have a band-pass transfer function that passes only the narrow band of oscillation frequency components of the TOF-intensity profile 54 corresponding to the optical pathlength L2.

Figure 11:
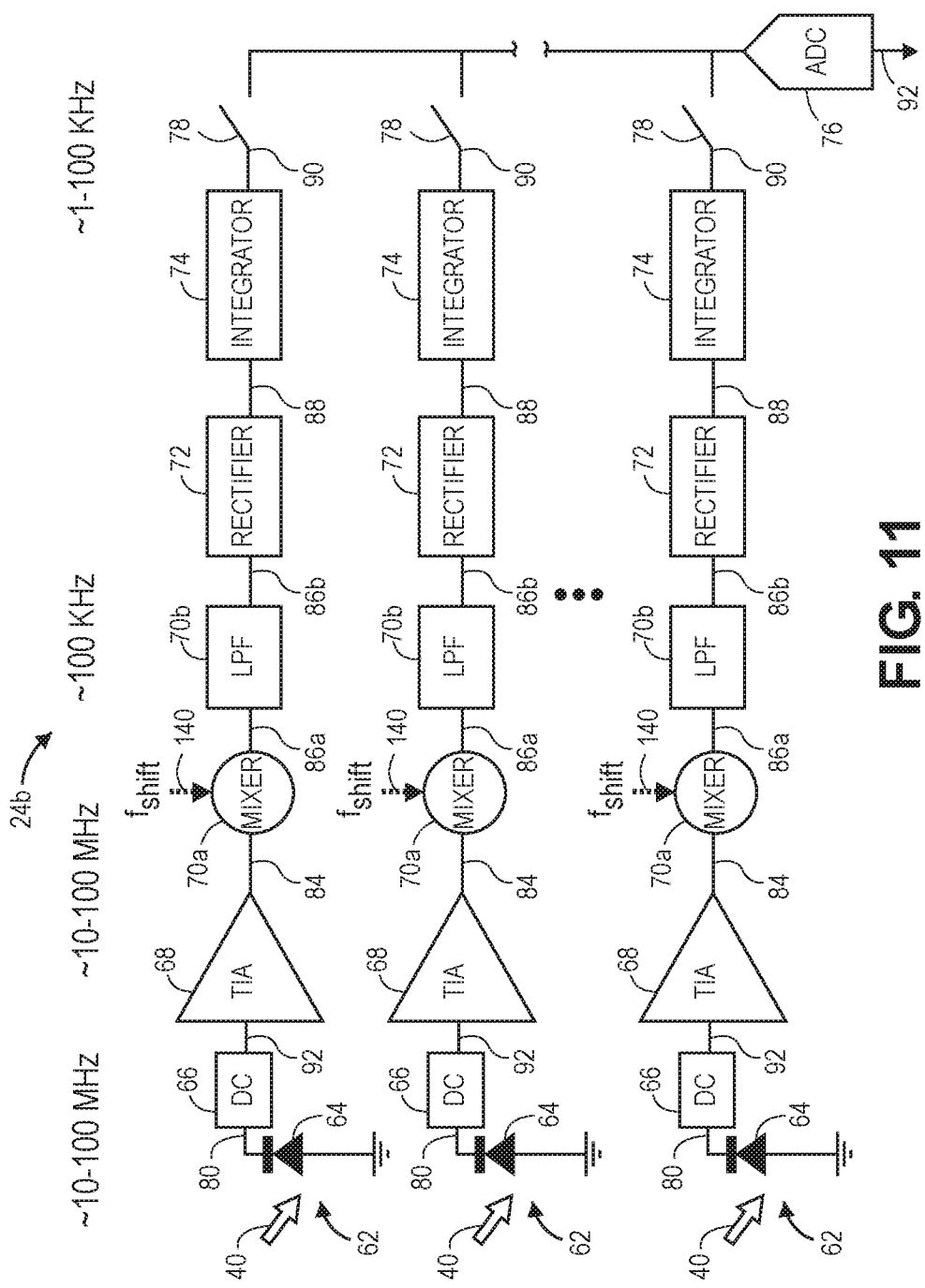
FIG. 11 is a block diagram of electronic componentry of another embodiment of an optical detector chip used in the optical measurement system of FIG. 1.

Alternatively, as shown in FIG. 11, instead of a BPF 70, one embodiment of a multi-channel optical detector chip 24*b* employs a frequency filter assembly that comprises a frequency mixer 70*a* and low-pass filter (LPF) 70*b*.

In particular, the frequency mixer 70a is coupled to the output of the respective amplifier 68 for frequency mixing the oscillation frequency components of the respective amplified AC analog signal 84 in response to a frequency control signal 140 with a frequency $f_{shift}$, and outputting a frequency down-shifted analog signal 86a comprising a plurality of oscillation frequency components (which include all of the oscillation frequency components respectively corresponding to the plurality of optical paths (e.g., all of the optical pathlengths L1-L4)) that are downshifted by the frequency $f_{shift}$ to lower oscillation frequency components. For example, as illustrated in FIG. 13B, the frequency mixer 70a downshifts all of the oscillation frequency components of the TOF-intensity profile 54 by the frequency $f_{shift}$ to a TOF-intensity profile 54' having lower (downshifted) oscillation frequency components (which include all of the down-shifted oscillation frequency components respectively corresponding to the plurality of optical paths (e.g., all of the optical pathlengths L1-L4)). Preferably, the oscillation frequency component corresponding to the current optical pathlength of interest is downshifted close to zero frequency.

The LPF 70b is coupled to the output of the frequency mixer 70a for low-pass filtering the respective frequency downshifted analog signal 86a, and outputting the respective pathlength-encoded analog signal 86b comprising a narrow band of down-shifted oscillation frequency components having a center oscillation frequency component corresponding to the current optical pathlength of interest (e.g., one of the optical pathlengths L1-L4). For example, as illustrated in FIG. 13B, the LPF 70b may have a low-pass transfer function that passes only the narrow band of downshifted oscillation frequency components of the TOF-intensity profile 54 corresponding to the optical pathlength L2. For example, the cutoff frequency of the LPF 70b may approach 0.

Each analog channel 62 of the multi-channel optical detector chip 24a further comprises a rectifier 72 coupled to the output of the respective BPF 70 (FIG. 10) or coupled to the output of the respective LPF 70b (FIG. 11) for converting the AC current of the respective pathlength-encoded analog signal 86 or 86b into rectified current, and outputting a rectified analog signal 88 (see FIG. 12E).

Figure 12F:
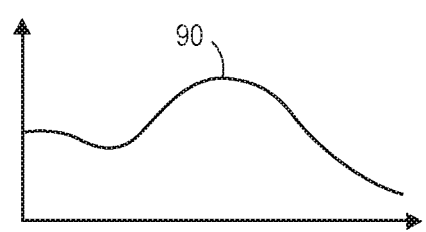
FIG. 12F is a diagram illustrating an exemplary low-bandwidth analog signal generated in the multi-channel optical detector chips of FIGS. 10 and 11 after smoothing of the rectified analog signal.

Each analog channel 62 of the multi-channel optical detector chip 24a further comprises a smoothing circuit 74 coupled to the output of the respective rectifier 72 for smoothing the rectified analog signal 88, and outputting a low-bandwidth (i.e., slower time-varying) analog signal 90 comprising the envelope (as the extracted characteristic) of the respective high-bandwidth analog signal 80 at the current optical pathlength of interest (see FIG. 12F). In the illustrated embodiment, each smoothing circuit 60 takes the form of an integrator, although in other embodiments, the smoothing circuit 60 may be a low-pass filter or envelope detector. Thus, the rectifier 72 and smoothing circuit 74, in combination, essentially extract the energy from the respective pathlength-encoded analog signal 86 or 86b, such that the low-bandwidth analog signal 90 comprises the extracted envelope of the respective high-bandwidth analog signal 80 at the current optical pathlength of interest.

Significantly, the bandwidth of the low-bandwidth analog signal 90 output from the smoothing circuit 74 will be much lower than the bandwidth of the high-bandwidth analog signal 80 output by the respective optical detector 64. Although the bandwidth of the low-bandwidth analog signal 90 is relatively small, the low-bandwidth analog signal 90 is fast enough to detect variations in the physiologically-dependent optical signal of interest, but slow enough to digitally process, along with all of the other low-bandwidth analog signals 90 output by the other smoothing circuits 74, in real-time, which will depend on the technique that the processor 30 utilizes to detect neural activity.

Figure 8A:
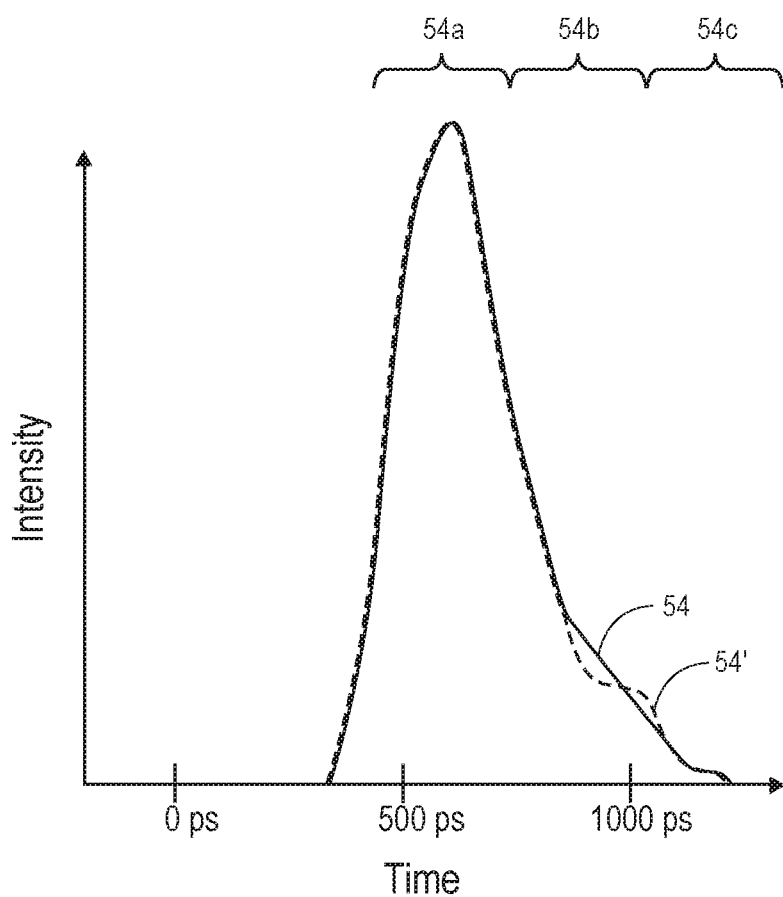
FIG. 8A is a timing diagram illustrating an exemplary TOF-intensity profile generated by the non-invasive optical detection system of FIG. 1.
Figure 8B:
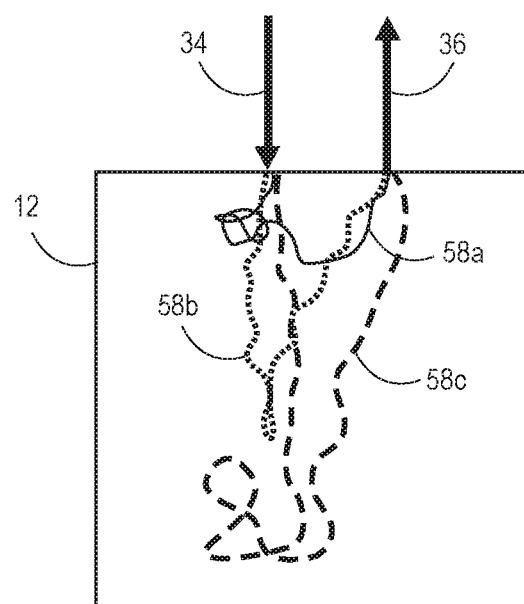
FIG. 8B is a plan view illustrating exemplary pathlengths of photons corresponding to different TOFs of the exemplary TOF-intensity profile of FIG. 8A.

For example, if the processor 30 conventionally performs TOF analysis by comparing previous and current TOF-intensity profiles 54 of the physiologically-encoded signal light 36, as shown in FIGS. 8A and 8B, the bandwidth of the low-bandwidth analog signal 90 output by the smoothing circuit 74 can be very low, e.g., in the range of 1 to 5 KHz. If, instead, the processor 30 performs DCS by computing an autocorrelation of the time-lapsed complex field of the physiologically-encoded signal light 36, as shown in FIGS. 9A-9C, the bandwidth of the low-bandwidth analog signal 90 output by the smoothing circuit 74 should be higher, e.g., 100 KHz.

It should be appreciated that the magnitudes of the low-bandwidth analog signals 90 will be scaled up versions of the envelopes of the high-bandwidth analog signals 80 at the current optical pathlength of interest, and thus, the envelopes of the high-bandwidth analog signals 80 at the current optical pathlength of interest may not be known in the absolute sense. However, because the processor 30 will ultimately determine the presence of neural activity in the brain 16 of the user 12 in response to relative changes in the physiologically-encoded signal light 36, only the relevant magnitudes of the envelopes of the high-bandwidth analog signals 80 extracted during different measurement periods are relevant.

For each series of analog channels 62 (corresponding to one dimension of the pixel array), the multi-channel optical detector chip 24a, 24b further comprises an analog-to-digital converter (ADC) 76 coupled to the outputs of the respective smoothing circuits 62 of the analog channels 62 via respective switches 78 for serially digitizing the low-bandwidth analog signals 90, and serially outputting low-bandwidth digital signals 92 respectively comprising sampled values of the extracted envelopes of the high-bandwidth analog signals 80 over time at the current optical pathlength of interest.

Thus, the controller 28 may sequentially close the switches 78 over the measurement period t (essentially controlling the frame rate of the multi-channel optical detector chip 24a, 24b), such that the processor 30 can serially read each of the analog channels 62 of the multi-channel optical detector chip 24a, 24b, and process the low-bandwidth digital signals 92. Depending on the manner in which the low-bandwidth digital signals 92 will be processed by the processor 30 (e.g., TOF analysis or DCS analysis), a single cycle of the switch 78 closures may be equal to or less than the duration of a single measurement period t, such that at least one low-bandwidth digital signal 92 for each channel will be acquired and stored in memory for each measurement period t.

Thus, each switching cycle between the analog channels 62 of the optical detector chip 24a, 24b may match a sweep cycle of the optical source 20, although in alternative embodiments, several switching cycles between the analog channels 62 of the optical detector chip 24a, 24b may be included within a single sweep cycle of the optical source 20. Although the low-bandwidth digital signals 92 will be serially output from the ADC 76, the data bit flow of each low-bandwidth digital signal 92 output from the ADC 76 is preferably in parallel.

Notably, the non-invasive optical detection system 10 can be dynamically tuned by shifting the transfer function of the frequency filter assemblies (e.g., the transfer function of the BPF 70 (FIG. 13A) or LPF 70b (FIG. 13B)) and the frequency band (i.e., the oscillation frequency components) of the high-bandwidth analog signals 80 output by the respective optical detectors 64 relative to each other, thereby allowing the current optical pathlength of interest (e.g., any of the optical pathlengths L1-L4), and thus, the depth in the brain 12, to be dynamically selected. The frequency band of the high-bandwidth analog signals 80 may be shifted optically or electrically in the absolute sense or the transfer function of the frequency filter assemblies can be shifted electrically in the absolute sense.

In one embodiment, the optical length of the reference arm of the interferometer 22 may be mechanically adjusted relative to the optical length of the sample arm of the interferometer 22 (e.g., via an adjustable mirror arrangement) in response to control signals from the controller 28 to optically shift the bandwidth (i.e., all of the oscillation frequency components) of the high-bandwidth analog signals 80 output by the respective optical detectors 64 up or down in the absolute sense. Because the transfer function of the transfer function of the frequency filter assemblies (e.g., the transfer function of the BPF 70 (FIG. 13A) or LPF 70b (FIG. 13B)) remains the same regardless of the change of the optical length of the reference arm of the interferometer 22, the pathlength-encoded analog signal 86 output by the BPF 70 or the pathlength-encoded analog signal 86b output by the LPF 70b will be encoded with a different current optical pathlength of interest (and thus a different depth within the brain 12) in accordance with the shift in the bandwidth of the high-bandwidth analog signals 80 output by the respective optical detectors 64. In effect, the sensitivity of the non-invasive optical detection system 10 to a particular oscillation frequency component in the high-bandwidth analog signals can be adjusted to extract only a narrow band of oscillation frequency components centered at the oscillation frequency component of the high-bandwidth analog signals 80 corresponding to the current optical pathlength of interest.

In another embodiment, a frequency control signal 140, having an adjustable frequency $f_{shift}$, synchronized to the output of the swept optical source 20, is used to electrically adjust the transfer function of the BPF 70 of each analog channel 62 in the absolute sense, or alternatively, the frequency control signal 140 is used to electrically adjust the frequency band of the high-bandwidth analog signal 80 via the mixer 70a of each analog channel 62, thereby providing different optical pathlength measurements.

Figure 14:
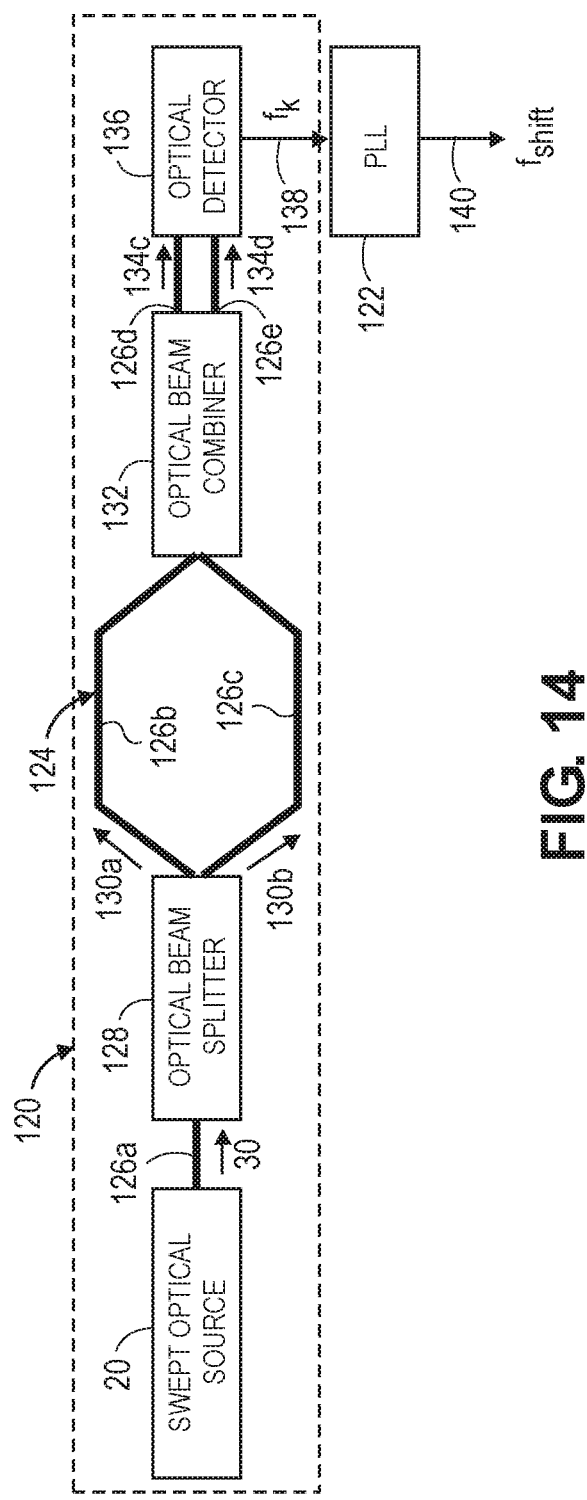
FIG. 14 is a block diagram of a k-clock modulation and phase locked loop (PLL) that can be employed by the multi-channel optical detector chips of FIGS. 10 and 11 to generate a control signal for generating the pathlength-encoded AC signal.

In particular, with reference to FIG. 14, the adjustable frequency $f_{shift}$ may be generated using a k-clock module 120, which generates a reference frequency (referred to as a "k-clock") that compensates for instabilities and/or non-linearities in the tuning of the optical source 20, and a phased locked loop (PLL) 122, which adjusts the frequency $f_{shift}$ of the frequency control signal 140 as a function of the k-clock signal.

The k-clock module 120 comprises an optical interferometer 124, e.g., a Mach-Zehnder type interferometer, that generates a reference frequency (referred to as a "k-clock") that compensates for instabilities and/or non-linearities in the tuning of the optical source 20. The interferometer 124 is optical fiber-based (i.e., uses optical fibers to direct light between the components), although in alternative embodiments, the interferometer 124 may direct light via free-space propagation between the components using optics, such as mirrors. Essentially, the interferometer 124 is designed to emulate the interferometer 22 of the non-invasive optical detection system 10.

The interferometer 124 comprises an input optical fiber 126a that optically couples the interferometer 124 to the optical source 20 for receiving a small portion of the source light 32 (e.g., 1%) tapped from the optical source 20 via an optical beam splitter (not shown); an optical fiber-based optical beam splitter 128 for splitting the source light 32 into first light 130a and second light 130b, a first arm optical fiber 126b and a second arm optical fiber 126c for respectively propagating the first light 130a and the second light 130b along the first and second arms of the interferometer 124; and an optical beam combiner 132 configured for receiving the first signal light 130a from the first arm optical fiber 126b, receiving the second signal light 130b from the second arm optical fiber 126c, and combining the first signal light 130a and second signal light 130b via superposition to generate first interference light 134a and second interference light 134b that are one hundred eighty degrees out of phase.

The k-clock module 120 further comprises a balanced optical detector 136 optically coupled to the optical beam combiner 132 via a first optical fiber 126d and a second optical fiber 126e for detecting the first interference light 132a and second interference light 132b, and outputting a k-clock signal 138 having a frequency $f_k$. The optical pathlength difference ($\Delta L$) between the first arm and second arm of the interferometer 124, and the sweep rate $$\left(\frac{\Delta\omega}{\Delta t}\right)$$

of the optical source 20, sets the frequency $f_k$ of the k-clock signal.

It is noted that, even though most practical and low-cost optical sources are not ideal in that they cannot be controlled to produce a linear optical sweep, using the reference pathlength in this manner produces a correct instantaneous beat frequency, thereby ensuring accurate depth gating.

The PLL 122 is programmable in response to control signals from the controller 28, and is configured for generating a frequency control signal 140 with an adjustable frequency $f_{shift}$ having the general form $f_{shift}=cf_k$, where the value of c is an adjustable ratio for adjusting the frequency $f_{shift}$ of the frequency control signal 140. The frequency of the control signal 140 can then be used to tune the BPF 70 (FIG. 10) or the mixer 70a (FIG. 11) to select the optical pathlength to be detected.

In still another embodiment, the sweeping rate $$\left(\frac{\Delta\omega}{\Delta t}\right)$$

of the optical source 20 may be modified in response to control signals from the controller 28 to optically adjust the frequency band of the high-bandwidth analog signal 80 output from the optical detector 64 of each analog channel 62, thereby providing different optical pathlength measurements. In this case, the BPF 70 (FIG. 10) or mixer 70a/LPF 70b (FIG. 11) can be designed to have a fixed transfer function.

Figure 15:
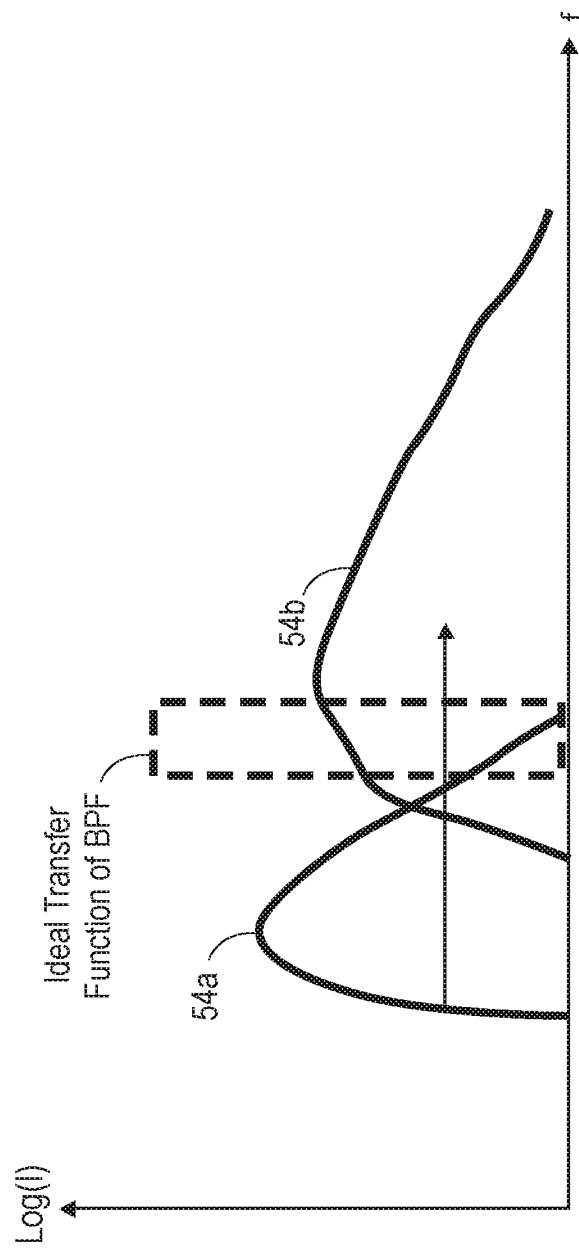
FIG. 15 is a timing diagram illustrating the stretching of an exemplary TOF-intensity profile by changing the sweep rate of the optical source of the non-invasive optical detection system of FIG. 1, wherein the optical pathlength is selected by a band-pass transfer function.

In particular, by changing the sweeping rate $$\left(\frac{\Delta\omega}{\Delta t}\right)$$

of the optical source 20, the frequency band of each high-bandwidth analog signal 80 will scale, and thus, the fixed frequency filter arrangement, although filtering the same frequency components, will effectively detect different optical pathlengths. For example, as illustrated in FIG. 15, increasing the sweeping rate $$\left(\frac{\Delta \omega}{\Delta t}\right)$$

of the optical source 20 will cause the TOF-intensity profile 54a of the high-bandwidth analog signal 80 (i.e., the physiologically-dependent signal light 36 detected by the optical detector 64 of each analog channel 62) to scale up or stretch to a different TOF-intensity profile 54b, and thus, the BPF 70 (which has a fixed transfer function) will be sensitive to a different oscillation frequency component in the high-bandwidth analog signal 80, and thus, a different optical pathlength.

Figure 16:
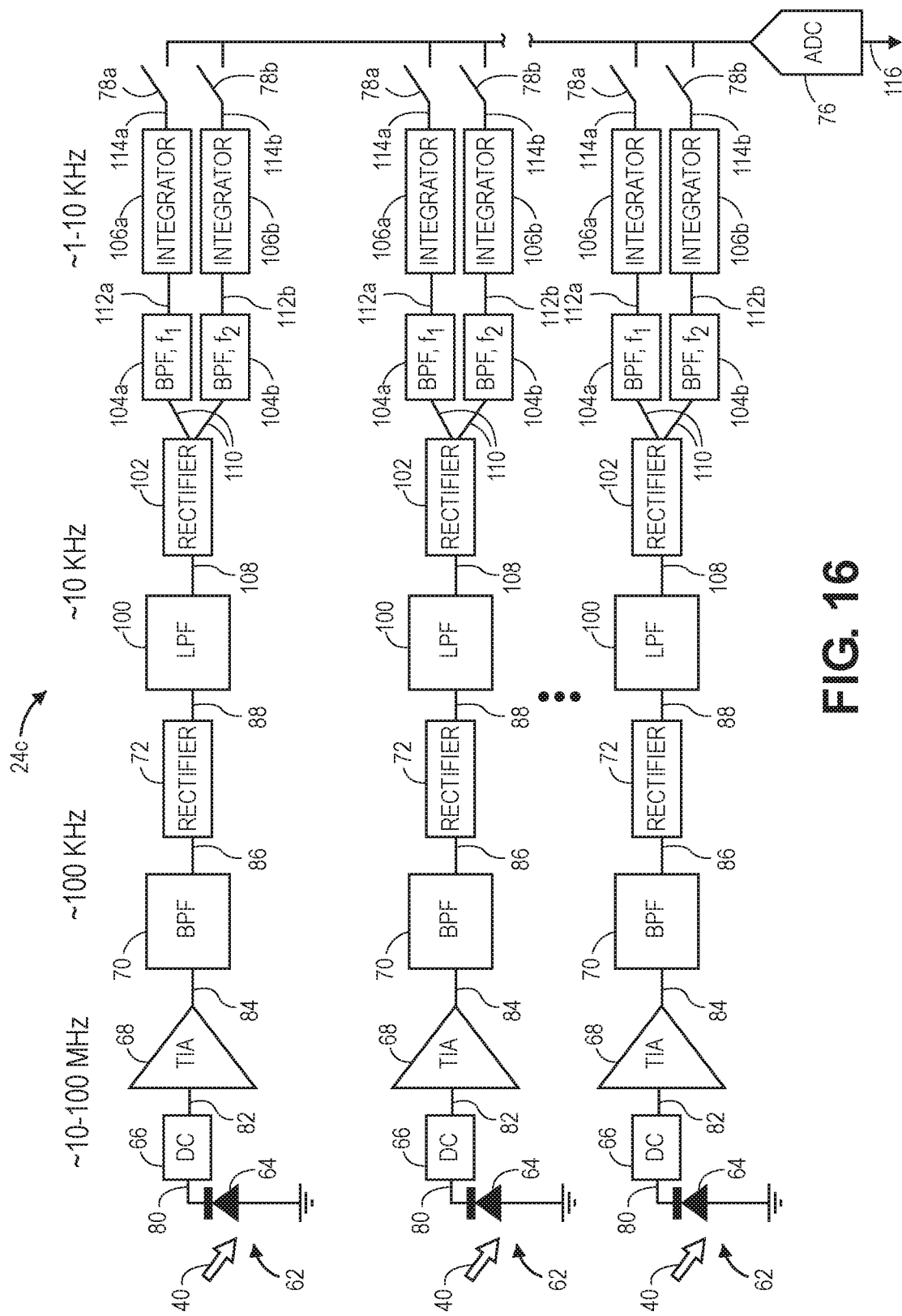
FIG. 16 is a block diagram of electronic componentry of still another embodiment of an optical detector chip used in the optical measurement system of FIG. 1.

Referring now to FIG. 16, one particular embodiment of an optical detection chip 24c is configured for, at least in part, performing DCS by using an autocorrelation technique to determine the decorrelation speed of the time-lapsed complex field of the physiologically-encoded signal light 36. Because the typical decorrelation signal in live tissue exhibits an exponential function, the dynamics of the tissue can be characterized by a decorrelation time constant τ within a fitting function of $\Delta e^{-t/\tau}$. In brain tissue, this decorrelation time constant τ can be used to identify neural activity. Therefore, it is advantageous to be able to extract the decorrelation time constant τ from the physiologically-encoded signal light 36.

The optical detection chip 24c uses the "Weiner-Khinchin" theorem to simplify the autocorrelation computation by extracting multiple points (in this case, two points) on the decorrelation speed of the physiologically-encoded signal light 36, which points can then be digitized and transferred as a very low-bandwidth signal to the processor 30, which may then use the multiple points to determine the decorrelation time constant τ of the decorrelation speed via a fitting process.

The Weiner-Khinchin theorem shows that the autocorrelation of a time series is the inverse Fourier transform of the squared amplitude of the Fourier transform of the time series. If it is assumed that the intensity of light for a given optical pathlength L (or time-of-flight (TOF)) computed as $$\frac{L}{c}n_r,$$

where c is the speed of light and $n_r$ is the refractive index of tissue) is I(L,t), then the autocorrelation of the intensity of the light is $$J(L,t)|_{0<t<\frac{t_0}{2}} = \int_0^{t_0/2} I(L,t)*I(L,t+x)dx.$$

If it is further assumed that, for a given pathlength $L=L_0$, the autocorrelation of the intensity of the light is an exponential function given by $J(L, t)|_{L=L_0} \approx J_0 e^{-t/\tau} = \int_0^{t_0/2} I(L, t)*I(L, t+x) dx$, the Fourier transform of such function will be a Lorentzian function:

$$F[J(L_0, t)] = J_0 \frac{2}{\tau[\omega^2 + (1/\tau)^2]}.$$

Since the autocorrelation of the intensity of the light must also be the squared amplitude of the Fourier transform of the time series in accordance with the Weiner-Khinchin theorem, i.e., $|F[I(L_0, t)]|^2$, to extract the decorrelation time constant τ for a time series at $L=L_0$, the value of the function: $F[J(L_0, t)]$ need only be determined for a few frequency points (e.g., $\omega=\omega_1$; $\omega=\omega_2$; etc.), and then fit to the function:

$$J_0 \frac{2}{\tau[\omega^2 + (1/\tau)^2]}$$

for these values to accurately determine the decorrelation time constant τ.

The multi-channel optical detector chip 24c is similar to the multi-channel optical detector chip 24a or multi-channel optical detector chip 24b, in that each analog channel 62 of the multi-channel optical detector chip 24c comprises an optical detector 64 that detects a different subset of optical modes of the interference light pattern 40, and thus the physiologically-encoded signal light 36, and outputs a high-bandwidth analog signal 80 respectively corresponding to the corresponding subset of optical modes of the interference light pattern 40; a DC removal element 66 coupled to the respective optical detector 64 for removing the DC component from the high-bandwidth analog signal 80, and outputting a purely AC analog signal 82 containing only AC frequency components; an amplifier 68 coupled to the output of the respective DC removal element 66 for amplifying the AC analog signal 82, and outputting an amplified AC analog signal 84 containing amplified AC frequency components; a BPF 70 coupled to the output of the respective amplifier 68 for band-pass filtering the amplified AC analog signal 84, and outputting a pathlength-encoded analog signal 86 corresponding to one of the optical pathlengths (i.e., an analog signal encoded with the current optical pathlength of interest (i.e., depth in the brain 12)), e.g., one of the optical pathlengths L1-L4 (or alternatively, a frequency mixer 70a coupled to output of the respective amplifier 68 for frequency mixing the oscillation frequency components of the respective amplified AC analog signal 84 in response to an control signal 140 having the frequency $f_{shift}$, and outputting a frequency down-shifted analog signal 86a comprising a plurality of oscillation frequency components respectively corresponding to the plurality of optical paths (e.g., all of the optical pathlengths L1-L4) that are downshifted by the frequency $f_{shift}$ to lower oscillation frequency components and an LPF 70b coupled to the output of the frequency mixer 70a for low-pass filtering the respective frequency down-shifted analog signal 86a, and outputting the respective pathlength-encoded analog signal 86b comprising the oscillation frequency component corresponding to the current optical pathlength of interest (e.g., one of the optical pathlengths L1-L4); and a rectifier 72 coupled to the output of the respective BPF 70 or LPF 70b for converting the AC current of the respective pathlength-encoded analog signal 86 or 86b into rectified current, and outputting a rectified analog signal 88.

As also described above with respect to the multi-channel optical detector chip 24a, 24b, the non-invasive optical detection system 10 can be dynamically tuned by shifting the transfer function of the frequency filter assemblies (e.g., the transfer function of the BPF 70 (FIG. 13A) or LPF 70b (FIG. 13B)) and the frequency band (i.e., the oscillation frequency components) of the high-bandwidth analog signals 80 output by the respective optical detectors 64 relative to each other, thereby allowing the current optical pathlength of interest (e.g., any of the optical pathlengths L1-L4), and thus, the depth in the brain 12, to be dynamically selected.

Figure 18:
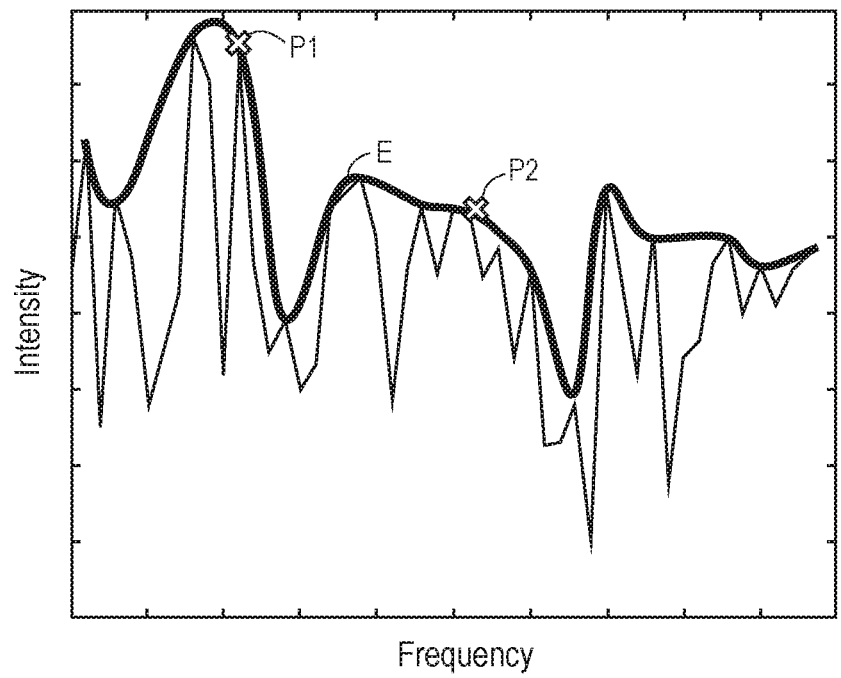
FIG. 18 is a diagram of an envelope of a Fourier transform of a squared amplitude of a pathlength-encoded analog signal computed by the electronic componentry of the optical detector chip of FIG. 16, particularly illustrating extracted points on the envelope.

In contrast to the multi-channel optical detector chips 24a and 24b, each analog channel 62 of the multi-channel optical detector chip 24c performs additional processing on the respective pathlength-encoded analog signal 86 or 86b to facilitate DCS analysis of each subset of optical modes of the interference light pattern 40 by the processor 30. In particular, each analog channel 62 of the multi-channel optical detector chip 24c is configured for computing the squared amplitude of the Fourier transform of the respective high-bandwidth analog signal 80, and extracting a plurality of points on an envelope of the squared amplitude of the Fourier transform of the respective pathlength-encoded analog signal 86. For example, as illustrated in FIG. 18, two points P1, P2 of an envelope E of the squared amplitude of the Fourier transform of the respective pathlength-encoded analog signal 86 can be extracted, as described in further detail below. The processor 30 may then determine the decorrelation time constant $\tau$ of the tissue in the brain 16 of the user 12 based on these points P1, P2, so that the processor 30 need not compute a time-intensive autocorrelation of the pathlength-encoded analog signal 86.

To this end, each analog channel 62 of the multi-channel optical detector chip 24c further comprises an LPF 100 coupled to the output of the respective rectifier 72 for extracting the low-frequency energy from the respective pathlength-encoded analog signal 86, and outputting a low-frequency AC analog signal 108, and a rectifier 102 coupled to the output of the respective LPF 100 for rectifying the low-frequency AC analog signal 108, and outputting a rectified signal 110 that represents the squared amplitude of the Fourier transform of the respective pathlength-encoded analog signal 86 (i.e., of the high-bandwidth analog signal 80 at the current optical pathlength of interest), and thus the autocorrelation of high-bandwidth analog signal 40. The bandwidth of the low-frequency AC analog signal 108 may be, e.g., around 10 KHz.

Each analog channel 62 of the multi-channel optical detector chip 24c further comprises a set of BPFs 104 (and in the illustrated embodiment, first and second BPFs 104a, 104b) coupled to the output of the rectifier 102 for band-pass filtering the rectified analog signal 110, and respectively outputting an analog signal 124a having a first frequency band, and an analog signal 124b having a second frequency band. The first BPF 104a has a first center frequency ($f_1$), such that the analog signal 112a corresponds to a first intensity value of the first frequency band of the squared amplitude of the Fourier transform (i.e., the first point P1 on the envelope E of the squared amplitude of the Fourier transform) of the respective pathlength-encoded analog signal 86, and the second BPF 104b has a second different center frequency ($f_2$), such that the analog signal 112b corresponds to a second intensity value of the second frequency band of the squared amplitude of the Fourier transform (i.e., the first point P2 on the envelope E of the squared amplitude of the Fourier transform) of the respective pathlength-encoded analog signal 86. Of course, additional BPFs can be connected in parallel with the output of the rectifier 102 to obtain additional points on the envelope E of the squared amplitude of the Fourier transform of the respective pathlength-encoded analog signal 86.

Each analog channel 62 of the multi-channel optical detector chip 24c further comprises first and second smoothing circuits 106a, 106b respectively coupled to the outputs of the first and second BPFs 104a, 104b for smoothing the analog signals 112a, 112b, and outputting low-bandwidth (i.e., slower time-varying) analog signals 114a, 114b respectively comprising the energy of the first and second frequency bands of the squared amplitude of the Fourier transform of the respective pathlength-encoded analog signal 86, and thus, the points P1, P2 on the envelope E of the squared amplitude of the Fourier transform of the respective pathlength-encoded analog signal 86. The bandwidth of the low-bandwidth analog signals 114a, 114b output by the smoothing circuits 106a, 106b can be very low, e.g., in the range of 1 to 10 KHz. In the illustrated embodiment, each smoothing circuit 106a, 106b takes the form of an integrator, although in other embodiments, each of the smoothing circuit 106a, 106b may be a low-pass filter or envelope detector.

In a similar manner described above with respect to the multi-channel optical detector chip 24a, for each series of analog channels 62 (corresponding to one dimension of the pixel array), the multi-channel optical detector chip 24c comprises an ADC 76 coupled to the outputs of the respective smoothing circuits 106a, 106b of the analog channels 62 via respective switches 78a, 78b for serially digitizing the low-bandwidth analog signals 114a, 114b, and serially outputting low-bandwidth digital signals 116 respectively comprising sampled values of the extracted points P1, P2 on the envelopes E of the absolute squares of the Fourier transforms of the respective pathlength-encoded analog signals 86 (i.e., of the high-bandwidth analog signals 80 at the current optical pathlength of interest).

The processor 30 may then fit the two points P1, P2 obtained from the low-bandwidth digital signals 116 for each analog channel 62 to the function $$J_0 \frac{2}{\tau[\omega^2 + (1/\tau)^2]}$$

to extract the decorrelation time constant $\tau$, which can then be analyzed over several periods (e.g., several sweeps of the optical source 20) to determine the presence and depth of a change in the physiologically-dependent optical signal, and thus the presence and depth of neural activity, in the brain 12 corresponding to the selected optical pathlength.

Figure 17:
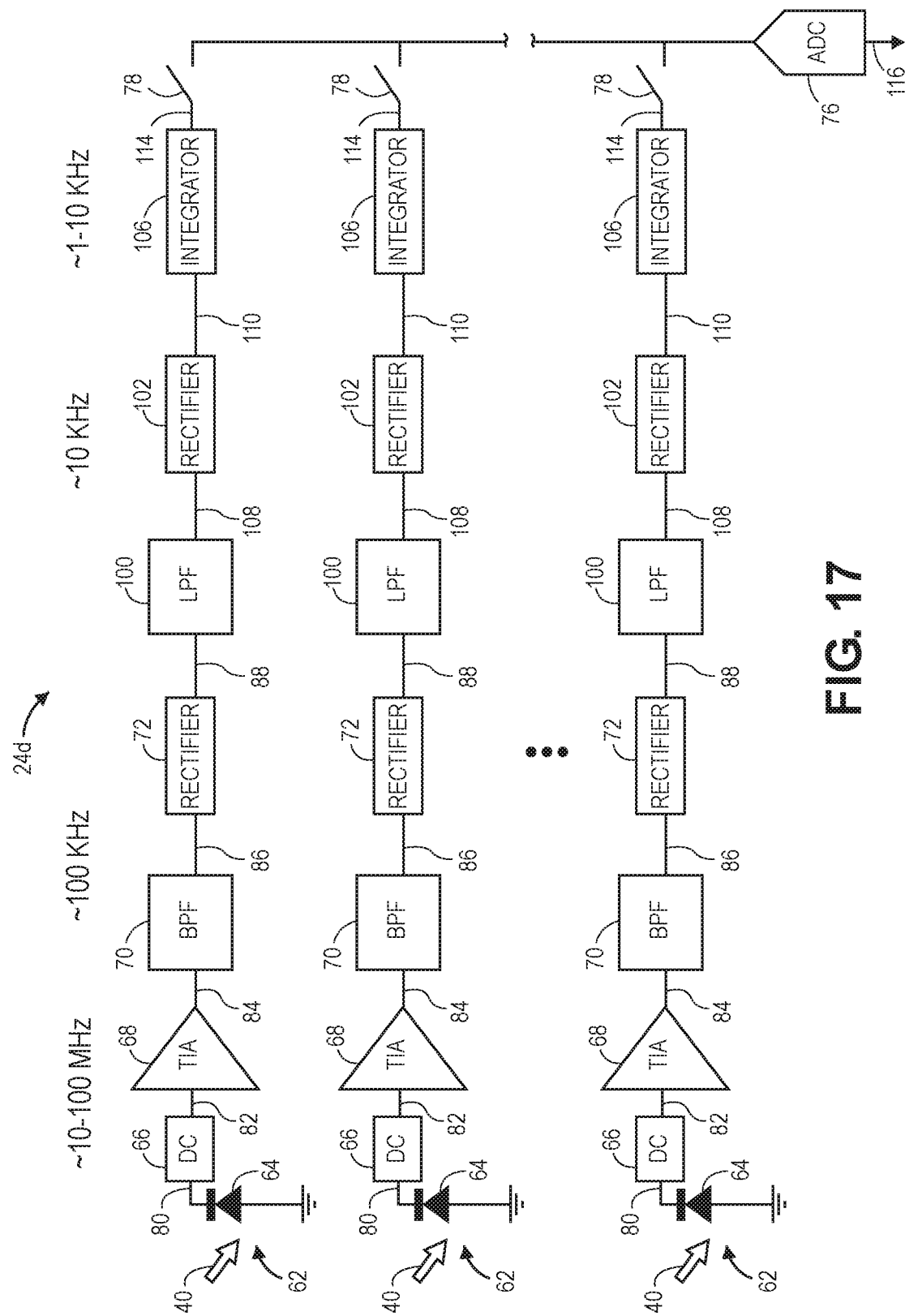
FIG. 17 is a block diagram of electronic componentry of yet another embodiment of an optical detector chip used in the optical measurement system of FIG. 1.
Figure 19:
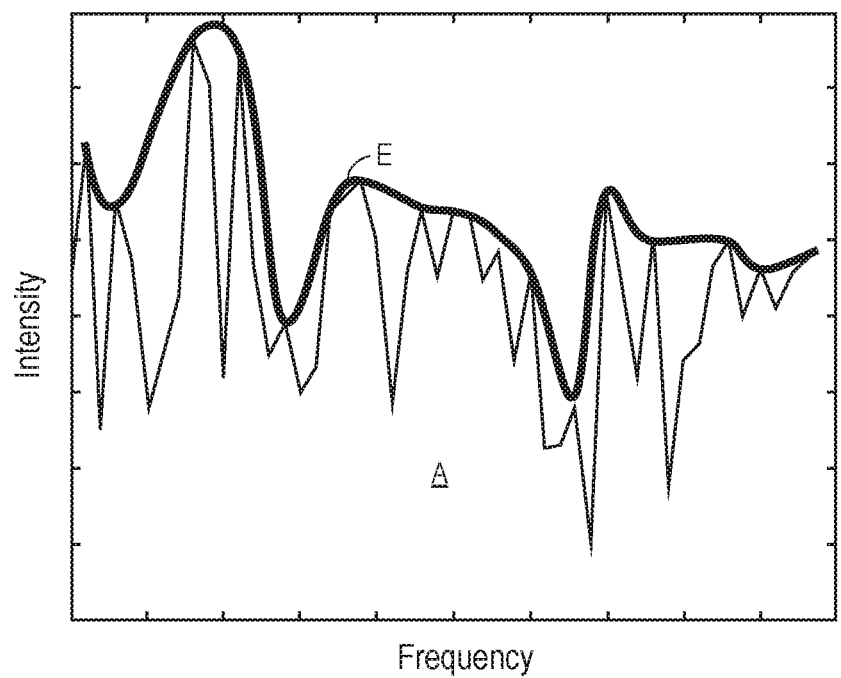
FIG. 19 is a diagram of an envelope of a Fourier transform of a squared amplitude of a pathlength-encoded analog signal computed by the electronic componentry of the optical detector chip of FIG. 16, particularly illustrating an extracted area underneath the envelope.

With reference to FIG. 17, another embodiment of a multi-channel optical detector chip 24d is similar to the multi-channel optical detector chip 24c of FIG. 16 in that each channel 62 of the multi-channel optical detector chip 24d is configured for computing the squared amplitude of the Fourier transform of the respective pathlength-encoded analog signal 86. However, the multi-channel optical detector chip 24d differs from the multi-channel optical detector chip 24c in that each channel 62 of the multi-channel optical detector chip 24 is configured for extracting an area (as the characteristic) underneath the envelope of the squared amplitude of the Fourier transform of the respective pathlength-encoded analog signal 86 (i.e., of the high-bandwidth analog signals 80 at the current optical pathlength of interest). For example, as illustrated in FIG. 19, an area A underneath an envelope E of the squared amplitude of the Fourier transform of the respective pathlength-encoded analog signal 86 can be extracted, as described in further detail below.

To this end, each channel 62 of the multi-channel optical detector chip 24*d* comprises a single integrator 106 (instead of multiple BPFs 104 and multiple integrators 106) coupled to the output of the rectifier 102 for integrating the rectified analog signal 110, and outputting a low-bandwidth analog signal 114 comprising the energy of the squared amplitude of the Fourier transform of the respective pathlength-encoded analog signal 86, and thus, the area A underneath the envelope E of the squared amplitude of the Fourier transform of the respective pathlength-encoded analog signal 86.

In a similar manner described above with respect to the multi-channel optical detector chip 24*a*, for each series of analog channels 62 (corresponding to one dimension of the pixel array), the multi-channel optical detector chip 24*d* comprises an ADC 76 coupled to the outputs of the respective integrators 106 via respective switches 78 for serially digitizing the low-bandwidth analog signals 114, and serially outputting low-bandwidth digital signals 116 respectively comprising sampled values of the extracted areas A underneath the envelopes E of the absolute squares of the Fourier transforms of the respective pathlength-encoded analog signals 86 (i.e., of the high-bandwidth analog signals 80 at the current optical pathlength of interest).

The processor 30 may then derive points on the envelope E from the area underneath the envelope E of the squared amplitude of the Fourier transform of the respective pathlength-encoded analog signal 86 for each analog channel 62, and then fit these points to the function $$J_0 \frac{2}{\tau[\omega^2 + (1/\tau)^2]}$$

to extract the decorrelation time constant τ, which can then be analyzed over several periods (e.g., several sweeps of the optical source 20) to determine the presence and depth of a change in the physiologically-dependent optical signal, and thus the presence and depth of neural activity, in the brain 12 corresponding to the selected optical pathlength.

Figure 20:
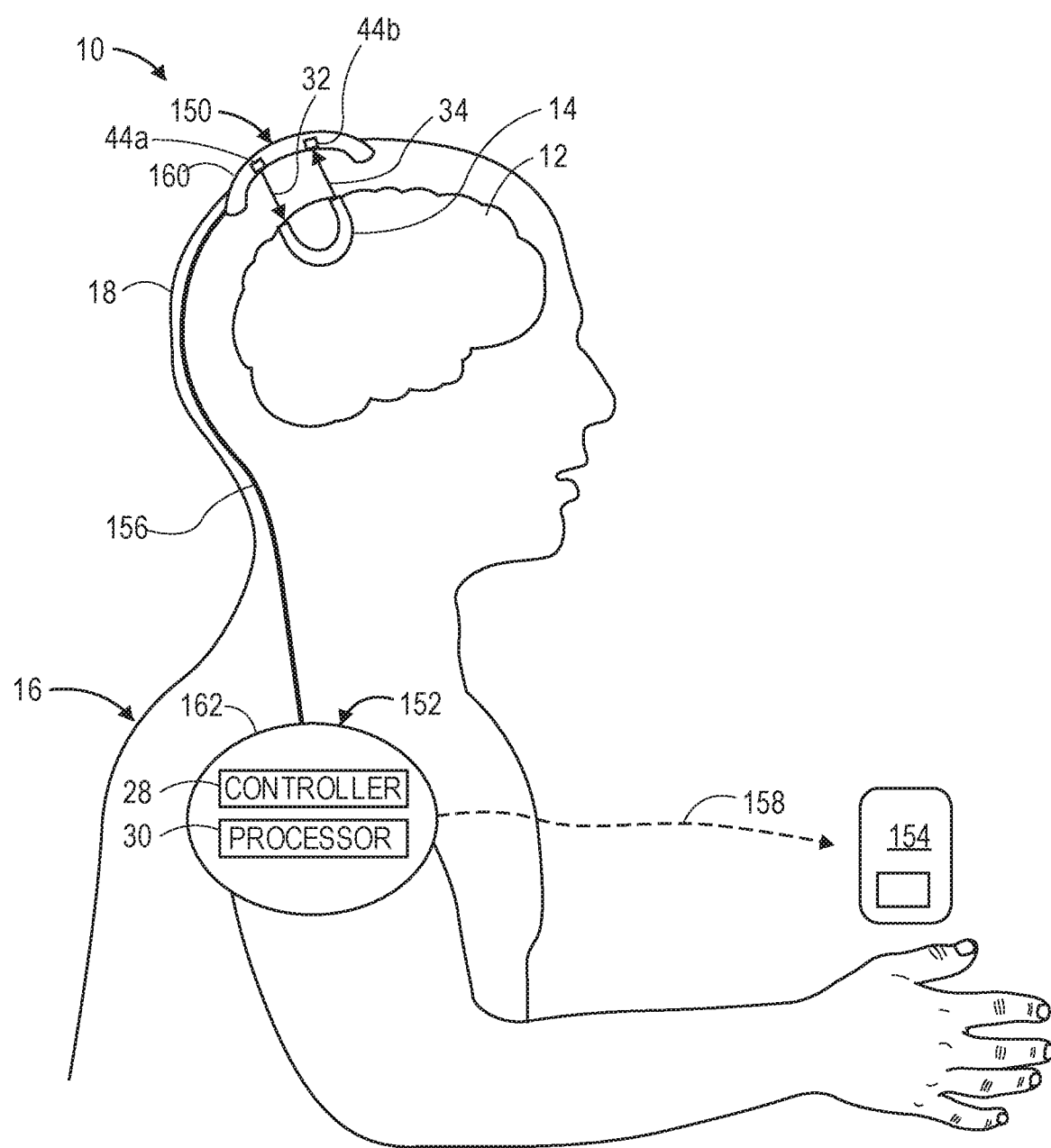
FIG. 20 is a plan view of a physical implementation of the non-invasive optical detection system of FIG. 1.

Referring now to FIG. 20, one physical implementation of the non-invasive optical detection system 10 for use in localizing a fast-optical signal in the brain 12 of a user 16 will be described. The non-invasive optical detection system 10 includes a wearable unit 150 that is configured for being applied to the user 16, and in this case, worn on the head 18 of the user 16; an auxiliary head-worn or non-head-worn unit 152 (e.g., worn on the neck, shoulders, chest, or arm) coupled to the wearable unit 150 via a wired connection 156 (e.g., electrical wires); and an optional remote processor 154 in communication with the user-wearable auxiliary unit 152 coupled via a wired connection 158 (e.g., electrical wires). Alternatively, the non-invasive optical detection system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 150 and the auxiliary unit 152, and/or a wired connection between the auxiliary unit 152 and the remote processor 154.

The wearable unit 150 comprises the optical source 20, interferometer 22, multi-channel optical detector chip 24, the output port 44*a* for emitting the sample light 34 generated by the optical source assembly 20 into the head 18 of the user 16, the input port 44*b* configured for receiving the physiologically-encoded signal light 36 from the head 18 of the user 16 and delivering it to the multi-channel optical detector chip 24 (illustrated in FIGS. 1 and 3), and a support structure 160 containing the optical source 20, interferometer 22, optical detector chip 24 (or optical detector chips 24), and ports 44*a*, 44*b*.

The auxiliary unit 152 comprises the controller 28 and the processor 30, and is analogous to the computing device 26 (illustrated in FIG. 1). The auxiliary unit 152 further comprises a housing 162 containing the controller 28 and processor 30. The controller 28 is configured for controlling the operational functions of the wearable unit 150, whereas the processor 30 is configured for processing the neural-encoded signal light 34 acquired by the wearable unit 150 to localize the fast-optical signal within the brain 12. The auxiliary unit 152 may additionally include a power supply (which if head-worn, may take the form of a rechargeable or non-chargeable battery), a control panel with input/output functions, a display, and memory. Alternatively, power may be provided to the auxiliary unit 152 wirelessly (e.g., by induction). The remote processor 154 may store data from previous sessions, and include a display screen.

As better illustrated in FIGS. 21A and 21B, the wearable unit 150 is configured for being placed adjacent to the head 18 of the user 16 and emitting the sample light 34 into the brain 12, where is scatters, resulting in the neural-encoded signal light 36 that exits the brain 12. In particular, the sample light 34 first passes through the scalp 164*a*, skull 164*b*, and cerebral spinal fluid (CSF) 164*c* along a relatively straight path, enters the brain 12, then exits in reverse fashion along a relatively straight path through the CSF 164*c*, skull 164*b*, and scalp 164*a*, thereby defining a banana-shaped optical path bundle 14. The wearable unit 150 may alternatively, by adding additional optical source-detector pairs, create multiple spatially separated detected optical path bundles 14 along which the light may propagate to enable x-y spatial localization of the fast-optical signal. For details discussing wearable units with multiple source-detector pairs are described in U.S. Provisional Patent Application Ser. No. 62/829,124, entitled "Modulation of Mental State of a User Using a Non-Invasive Brain Interface System and Method," which is expressly incorporated herein by reference.

Referring back to FIG. 20, the support structure 160 may be shaped, e.g., have a banana, headband or hat shape, or other shape adjustable to the head 18, such that the ports 44*a*, 44*b* are in close contact with the outer skin of the head 18, and in this case, the scalp of the user 16. In an alternative embodiment, optical fibers (not shown) may be respectively extended from the ports 44*a*, 44*b*, thereby freeing up the requirement that the ports 44*a*, 44*b* be disposed in close proximity to the surface of the head 18. In any event, an index matching fluid may be used to reduce reflection of the light generated by the wearable unit 150 from the outer skin of the scalp. An adhesive or belt (not shown) can be used to secure the support structure 160 to the head 18 of the user 16.

Figure 22A:
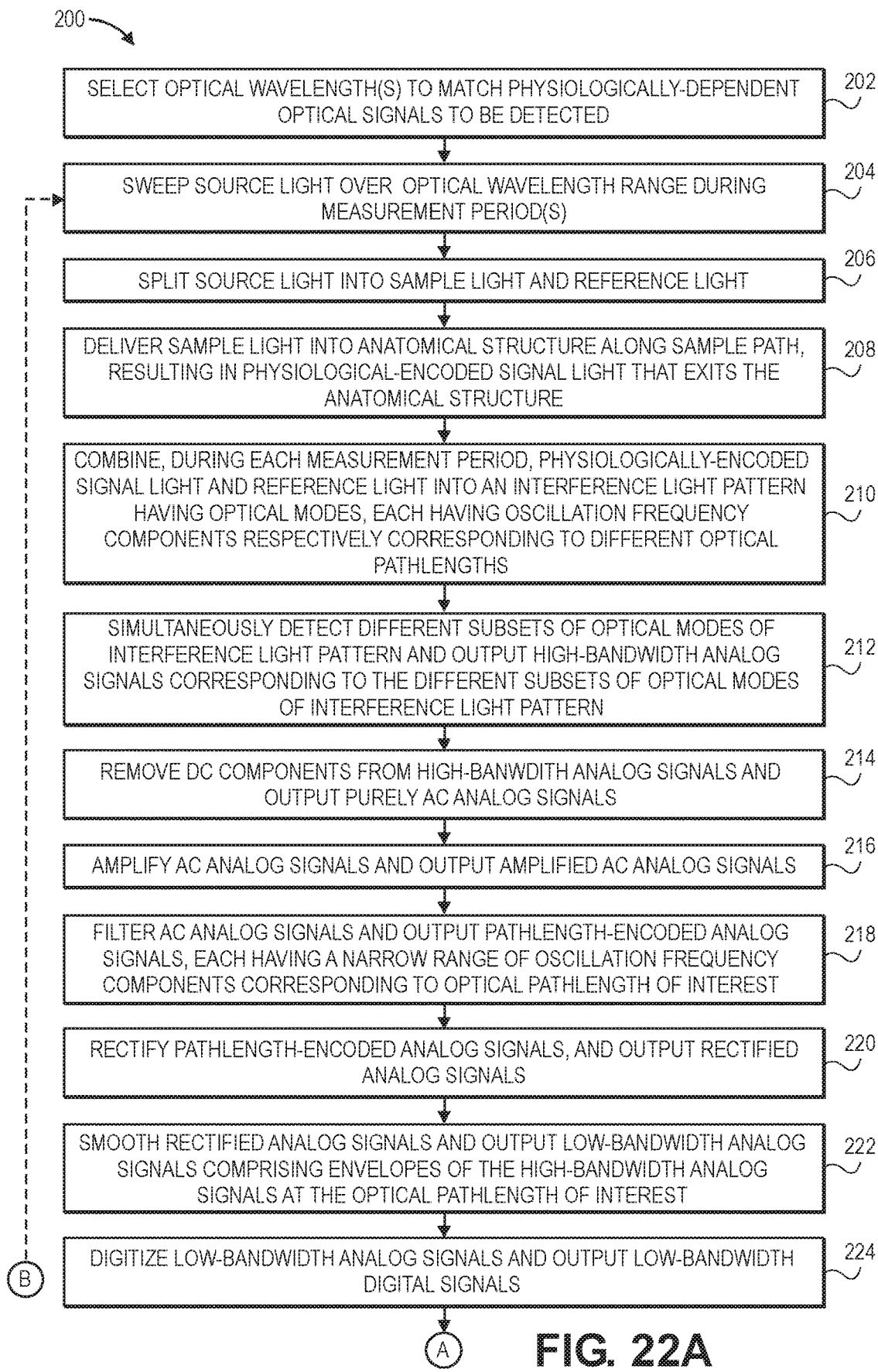
FIG. 22A is a first of two portions of a flow diagram illustrating one method used by the non-invasive optical detection system of FIG. 1 to non-invasively determine the presence and depth of a physiologically-dependent optical signal within an anatomical structure, particularly using the multi-channel optical detector chips of FIGS. 10 and 11.
Figure 22B:
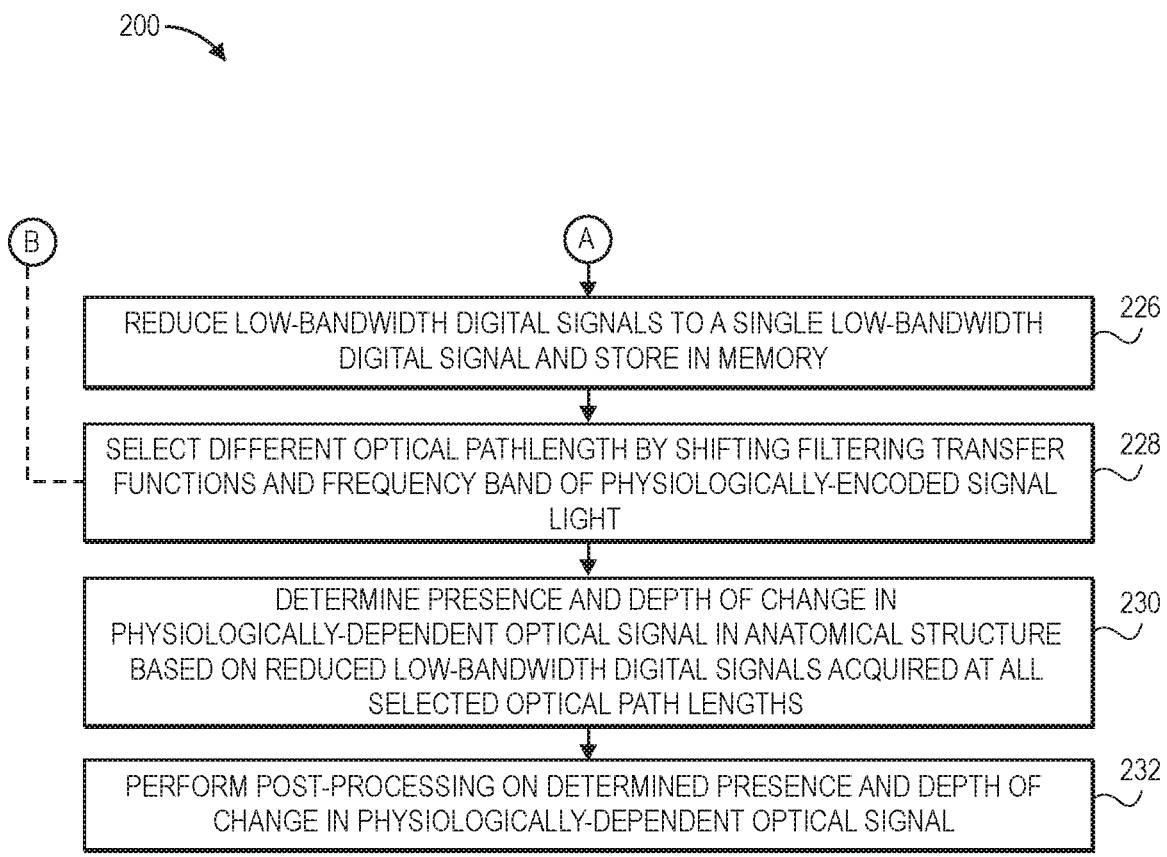
FIG. 22B is the second portion of the flow diagram of FIG. 22A.

Referring to FIG. 22, having described the structure and function of the non-invasive optical detection system 10, one particular method 200 performed by the non-invasive optical detection system 10 to non-invasively determine the depth of a change in a physiologically-dependent optical signal (e.g., a fast-optical signal or a hemodynamic change) in the anatomical structure 12 (in this case, the brain) will now be described.

The method 200 will be described in the context of the multi-channel optical detector chip 24a (FIG. 10) or the multi-channel optical detector chip 24b (FIG. 11). First, the optical wavelength(s) of the source light 32 is selected to match the physiologically-dependent optical signal to be detected in the brain 12 (step 202). In the case where the physiologically-dependent optical signal is a fast-optical signal, the optical wavelength may be greater than 850 nm. In the case where the physiologically-dependent optical signal is blood oxygen concentration, the optical wavelength may be selected to be in the range of 650 nm to 750 nm.

Next, the controller 28 sends a control signal to the drive circuit of the optical source 20 to repeatedly sweep the source light 32 over the optical wavelength range 50 during one or more measurement periods t, with each measurement period t corresponding to a single optical wavelength range sweep 50 (step 204). As discussed above, each measurement period t is preferably equal to or less than the speckle decorrelation time of the brain 12, e.g., equal to or less than 100 microseconds, and preferably, equal to or less than 10 microseconds.

The interferometer 22 (e.g., via the optical beam splitter 44) splits the source light 32 into the sample light 34 and the reference light 38 (step 206). The interferometer 22 then delivers the sample light 34 into the brain 12 along a single detected optical path bundle 14, such that the sample light 34 is scattered by the brain 12, resulting in physiologically-encoded signal light 36 that exits the brain 12 (step 208), and combines, during each of the measurement period(s) t (i.e., each sweep of the optical wavelength sweep 50), the physiologically-encoded signal light 36 and the reference light 38 into an interference light pattern 40 having a plurality of optical modes, with each optical mode having a plurality of oscillation frequency components (collectively, a first frequency band) respectively corresponding to a plurality of different optical pathlengths (e.g., optical pathlengths L1-L4) (i.e., respectively encoded with a plurality of different depths in the brain 12) (step 210).

While the optical wavelength of the source light 32 is repeatedly varied over the selected optical wavelength range 50, the multi-channel optical detector chip 24a, 24b (via the array of optical detectors 64) simultaneously detects different subsets of the plurality of optical modes of the interference light pattern 40 (i.e., sampled across the optical wavelength range) during each of the measurement period(s) t, and outputs a plurality of high-bandwidth analog signals 80 respectively corresponding to the different subsets of optical modes of the interference light pattern 40 (step 212). The multi-channel optical detector chip 24a, 24b (via the analog compression circuitry) then parallel processes the high-bandwidth analog signals 80 and outputs a plurality of low-bandwidth digital signals 92 (each having a frequency band less than the frequency band of the high-bandwidth analog signals 80).

In particular, the multi-channel optical detector chip 24a, 24b (via the DC removal elements 66) removes the DC components from the high-bandwidth analog signals 80, and outputs purely AC analog signals 82 (step 214). The multi-channel optical detector chip 24a, 24b (via the amplifiers 68) then amplifies the AC analog signals 82 and outputs amplified AC analog signals 84 (step 216). As discussed above, the DC removal function and amplification can be performed in a single step.

The multi-channel optical detector chip 24a, 24b then extracts at least one characteristic, and in this case, an envelope of each of the high-bandwidth analog signals 80 (and thus the physiologically-encoded signal light 36) at the current optical pathlength of interest, from the amplified AC analog signals 84, and outputs a plurality of low-bandwidth digital signals 92 respectively comprising the extracted envelopes of the high-bandwidth analog signals 80 at the current optical pathlength of interest.

In particular, the multi-channel optical detector chip 24a, 24b (via the frequency filter assemblies) first filters the amplified AC analog signals 84 and outputs a plurality of pathlength-encoded analog signals 86, each of which is encoded with one of the plurality of optical pathlengths (e.g., one of optical pathlengths L1-L4, as shown in FIGS. 6A and 6B) (step 218).

In the case of the multi-channel optical detector chip 24a, the frequency filter assemblies are BPFs 70 that band-pass frequency filter the amplified AC analog signals 84 and output the respective pathlength-encoded analog signals 86, each comprising the narrow band of oscillation frequency components corresponding to the respective optical pathlength. In the case of a multi-channel optical detector chip 24b, the frequency filter assemblies comprise frequency mixers 70a that frequency mix the oscillation frequency components of the respective amplified AC analog signals 84 with a base frequency, and output frequency down-shifted analog signals 86a comprising a plurality of down-shifted oscillation frequency components respectively corresponding to the plurality of optical pathlengths, and LPFs 70b that low-pass frequency filter the respective frequency down-shifted analog signals 86a and output the respective pathlength-encoded analog signals 86b, each comprising the narrow band of down-shifted oscillation frequency components corresponding to the current optical pathlength of interest.

The multi-channel optical detector chip 24a, 24b (via the rectifiers 72) rectifies the pathlength-encoded analog signals 86 and outputs a plurality of rectified signals 88 (step 220), and (via the smoothing circuits 74) smooths the rectified signals 88 and outputs a plurality of low-bandwidth analog signals 90 comprising the envelopes of the high-bandwidth analog signals 80 at the current optical pathlength of interest (step 222). The multi-channel optical detector chip 24a, 24b (via the ADC(s) 76) then digitizes the low-bandwidth analog signals 90 and serially outputs a plurality of low-bandwidth digital signals 92 comprising sampled values of the extracted envelopes of the high-bandwidth analog signals 80 at the current optical pathlength of interest (step 224). In digitizing the low-bandwidth analog signals 90, each ADC 76 may sequentially close the switches 78 coupled to the smoothing circuits 74 corresponding to each dimension (e.g., column) of analog channels 62, such that the ADC 76 sequentially digitizes the low-bandwidth analog signals 90, and serially outputs the low-bandwidth digital signals 92 corresponding to the column of analog channels 62. Thus, the ADCs 76 will simultaneously digitize the low-bandwidth analog signals 90 corresponding to columns of analog channels 62, while serially digitizing the low-bandwidth analog signals 90 within each column of analog channels 62.

Depending on the manner in which the low-bandwidth digital signals 92 will be processed by the processor 30 (e.g., TOF analysis or DCS analysis), a single closure cycle of the switches 78 may be equal to or less than the duration of a single measurement period t, such that at least one low-bandwidth digital signal 92 for each channel will be acquired and stored in memory for each measurement period t. For each plurality of low-bandwidth digital signals 92 acquired over the sets of optical modes of the interference light pattern 40 (i.e., for each cycle of switch 78 closures), the processor 30 reduces the plurality of low-bandwidth digital signals 92 to a single digital signal (e.g., by computing a mean of the low-bandwidth digital signals 92) and stores the single digital signals in memory (not shown) (step 226).

The controller 28 then selects a different optical pathlength by optically or electrically shifting the transfer functions of the frequency filter assemblies and the frequency band of the high-bandwidth analog signals 80 relative to each other (step 228), and repeats steps 204-226, where the source light 32 of the optical source 20 is swept over the range of optical wavelengths (step 204), the interferometer 22 generates the interference light pattern 40 (step 206-210), the multi-channel optical detector chip 24a, 24b detects the simultaneously detects the subsets of optical modes of the interference light pattern 40 during each of the measurement period(s) t, outputs the plurality of high-bandwidth analog signals 80 respectively corresponding to the different subsets of optical modes of the interference light pattern 40 (step 212), and parallel processes the high-bandwidth analog signals 80 and outputs a plurality of low-bandwidth digital signals 92 (steps 214-224), and the processor 30 reduces plurality of low-bandwidth digital signals 92 to a single low-bandwidth digital signal for storage in memory (step 226).

The optical detector system 10 may optically shift the transfer functions of the frequency filter assemblies and the frequency band of the high-bandwidth analog signals 80 relative to each other, e.g., by mechanically adjusting a mirror arrangement (not shown) that adjusts the length of the reference arm of the interferometer 22 to optically shift the frequency band of the high-bandwidth analog signals 80 or by adjusting the optical sweep rate sweeping rate $$\left(\frac{\Delta \omega}{\Delta t}\right)$$

at which the optical source 20 is swept over the range of optical wavelengths during each of the measurement period(s) t. Or the optical detector system 10 may electrically shift the transfer functions of the frequency filter assemblies and the frequency band of the high-bandwidth analog signals 80 relative to each other, e.g., by generating a k-clock signal 118 (via the k-clock module 120) that is locked to the source light 32 output by the optical source 30, selecting a multiplication factor c, and multiplying the frequency of the k-clock signal 118 with the multiplication factor c to generate a control signal 120 having a frequency that is ratio of the frequency of the k-clock signal 118. The transfer functions of the frequency filter assemblies may then be electrically shifted relative to the frequency band of the high-bandwidth analog signals 80 in response to the control signal 120.

Once the low-bandwidth digital signals 92 have been acquired, reduced, and stored in memory for all of the selected optical pathlengths, the processor 30 then determines the presence and depth (correlated to the selected optical pathlength L1-L4) of any change in the physiologically-dependent optical signal, based on the reduced low-bandwidth digital signals for all of the selected optical pathlengths stored in the memory, e.g., by performing a TOF analysis (FIGS. 8A-8B) or a DCS analysis (FIGS. 9A-9C) (step 230). In the case where multiple detected optical path bundles 14 through the brain 12 are created using complex source-detector arrangements (e.g., single-source multi-detector, multi-source single-detector, or multi-source multi-detector) to simultaneously create multiple detected optical path bundles 14 spatially separated from each other within the brain 12 in a single measurement period t, or by using a movable source-detector arrangement, the processor 30 may also determine the existence and location of a change in the physiologically-dependent optical signal in an x-y plane along the surface of the brain 12, such that a three-dimensional location of the change in the physiologically-dependent optical signal within the brain 12 is determined. The processor 30 then performs post-processing on the localized physiologically-dependent optical signal, e.g., determining the level and location of neural activity within the brain 12 (step 232).

Figure 23A:
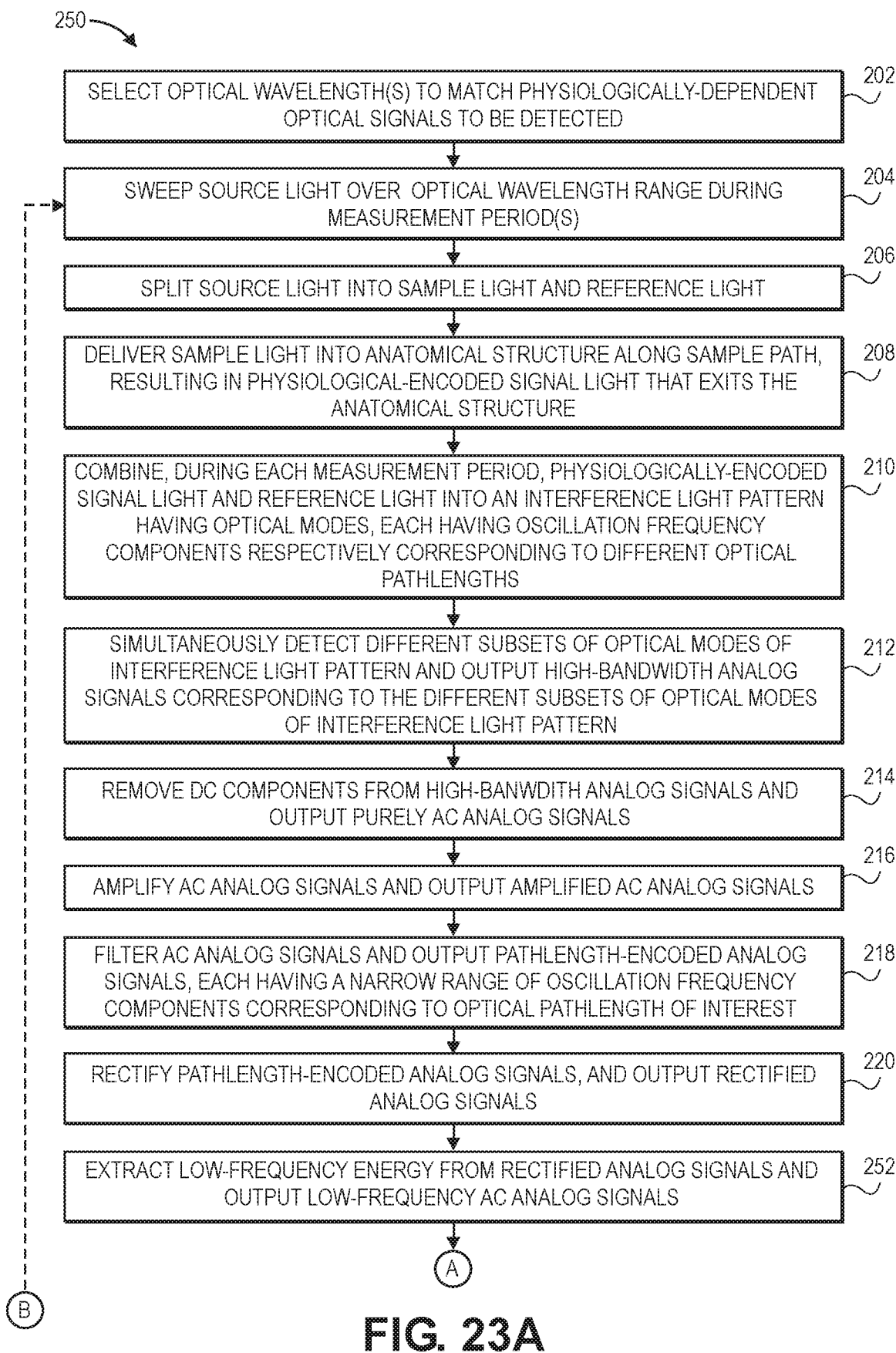
FIG. 23A is a first of two portions of a flow diagram illustrating one method used by the non-invasive optical detection system of FIG. 1 to non-invasively determine the presence and depth of a physiologically-dependent optical signal within an anatomical structure, particularly using the multi-channel optical detector chips of FIGS. 16 and 17.
Figure 23B:
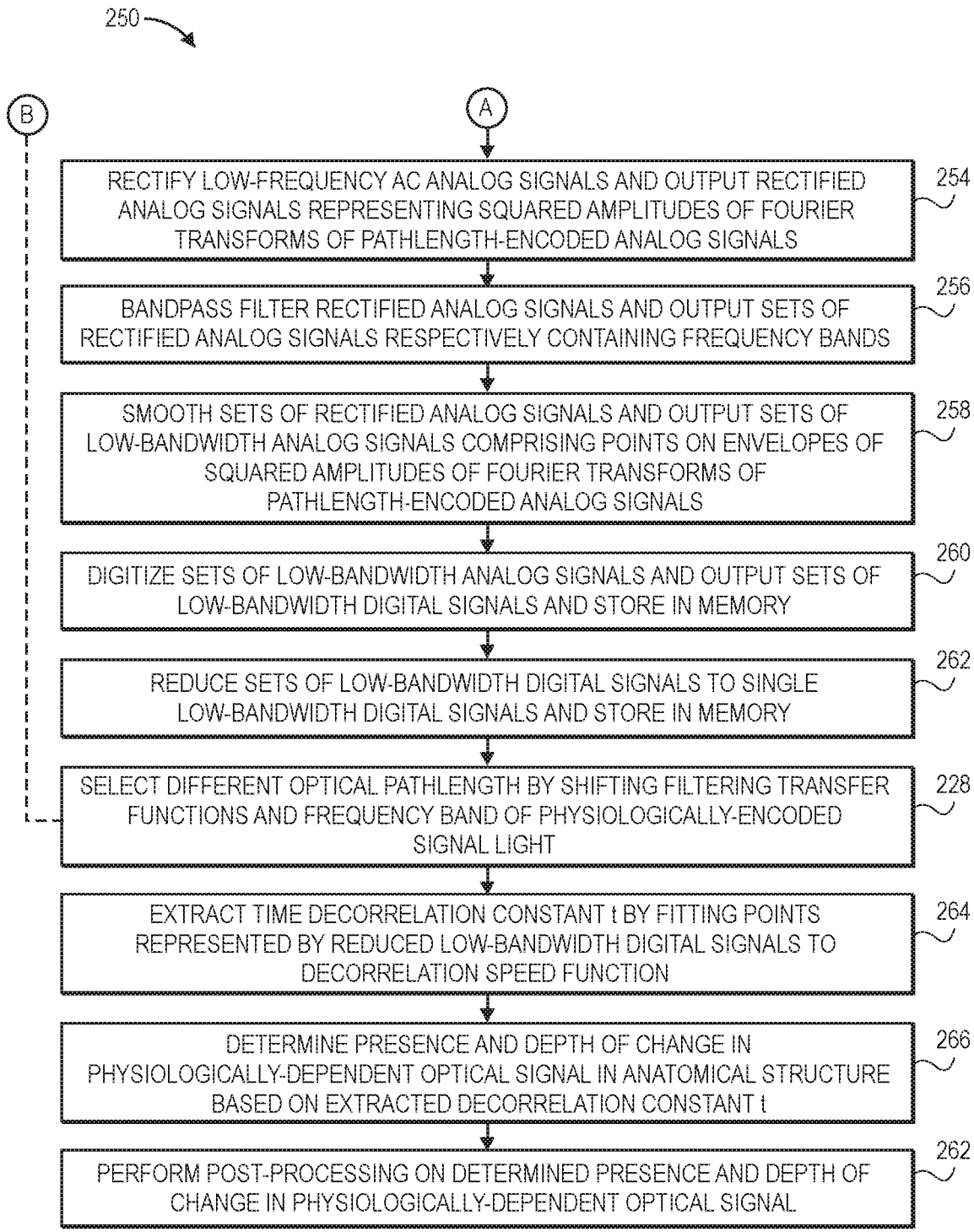
FIG. 23B is the second portion of the flow diagram of FIG. 23A.

Referring to FIG. 23, another method 250 performed by the non-invasive optical detection system 10 to non-invasively determine the depth of a change in a physiologically-dependent optical signal (e.g., a fast-optical signal or a hemodynamic change) in the anatomical structure 12 (in this case, the brain) will now be described in the context of the multi-channel optical detector chip 24c (FIG. 16) or the multi-channel optical detector chip 24d (FIG. 17). The method 250 is similar to the method 200 described above in FIG. 22 in that the optical wavelength(s) of the source light 32 is selected to match the physiologically-dependent optical signal to be detected in the brain 12 (step 202); the controller 28 sends a control signal to the drive circuit of the optical source 20 to repeatedly sweep the source light 32 over the optical wavelength range 50 during the measurement period(s) t, with each measurement period t corresponding to a single optical wavelength range sweep 50 (step 204); the interferometer 22 (e.g., via the optical beam splitter 44) splits the source light 32 into the sample light 34 and the reference light 38 (step 206); delivers the sample light 34 into the brain 12 along a single detected optical path bundle 14, such that the sample light 34 is scattered by the brain 12, resulting in physiologically-encoded signal light 36 that exits the brain 12 (step 208), and combines, during each of the measurement period(s) t (i.e., each sweep of the optical wavelength sweep 50), the physiologically-encoded signal light 36 and the reference light 38 into an interference light pattern 40 having a plurality of optical modes, with each optical mode having a plurality of oscillation frequency components (collectively, a frequency band) respectively corresponding to a plurality of optical pathlengths (e.g., optical pathlengths L1-L4) (i.e., respectively encoded with a plurality of different depths in the brain 12) (i.e., respectively encoded with a plurality of different depths in the brain 12) (step 210).

Furthermore, the multi-channel optical detector chip 24c, 24d operates in the same manner in the method 200 as the multi-channel optical detector chip 24a, 24b operates in the method 200 in that, while the optical wavelength of the source light 32 is repeatedly varied over the selected optical wavelength range 50, the multi-channel optical detector chip 24c, 24d (via the array of optical detectors 64) simultaneously detects the subsets of optical modes of the interference light pattern 40 (i.e., sampled across the optical wavelength range) during each of the measurement period(s) t, and outputs a plurality of high-bandwidth analog signals 80 respectively corresponding to the different subsets of optical modes of the interference light pattern 40 (step 212); (via the DC removal elements 66) removes the DC components from the high-bandwidth analog signals 80, and outputs purely AC analog signals 82 (step 214); (via the amplifiers 68) amplifies the AC analog signals 82 and outputs amplified AC analog signals 84 (step 216); (via the frequency filter assemblies) then filters the amplified AC analog signals 84 and outputs a plurality of pathlength-encoded analog signals 86, each of which comprises a narrow band of oscillation frequency components corresponding the current optical pathlength of interest (e.g., one of optical pathlengths L1-L4, as shown in FIGS. 6A and 6B) (step 218).

The method 250 differs from the method 200 in that the multi-channel optical detector chip 24*c*, 24*d* performs additional analog processing by computing the squared amplitude of the Fourier transforms of the squared amplitudes of the pathlength-encoded analog signals 86, and extracts a plurality of points on an envelope of the squared amplitude of the Fourier transform of each of the respective pathlength-encoded analog signals 86, thereby facilitating DCS analysis of the physiologically-encoded signal light 36 by the processor 30.

In particular, the multi-channel optical detector chip 24*c*, 24*d* (via the rectifiers 72) rectifies the pathlength-encoded analog signals 86 and outputs a plurality of rectified analog signals 88 (step 220), (via the LPFs 100) extracts the low-frequency energy from the rectified analog signals 88, and outputs low-frequency AC analog signals 108 (step 252), and (via the rectifiers 102) rectifies the low-frequency AC analog signals 108, and outputs rectified analog signals 110 that represent the squared amplitudes of the Fourier transforms of the pathlength-encoded analog signals 86 (i.e., the high-bandwidth analog signals 80 at the current optical pathlength of interest) (step 254).

In the case where the points on the envelope of squared amplitude of the Fourier transform of each of the respective pathlength-encoded analog signals 86, the multi-channel optical detector chip 24*c* (via the sets of BPFs 104*a*, 104*b*) band-pass filters the rectified analog signals 110, and respectively outputs sets of analog signals 112*a*, 112*b* containing first and second frequency bands that respectively represent points on the envelopes of the squared amplitudes of the Fourier transforms of the pathlength-encoded analog signals 86 (step 256). The multi-channel optical detector chip 24*c* (via the sets of smoothing circuits 106*a*, 106*b*) smooths the sets of rectified analog signals 112*a*, 112*b*, and outputs sets of low-bandwidth (i.e., slower time-varying) analog signals 114*a*, 114*b* comprising the points on the envelopes of the squared amplitudes of the Fourier transforms of the pathlength-encoded analog signals 86 (step 258).

Alternatively, in the case where the area underneath the envelope of squared amplitude of the Fourier transform of each of the respective pathlength-encoded analog signals 86, the multi-channel optical detector chip 24*c* (via the integrators 106) smooths the rectified analog signals 110, and outputs low-bandwidth analog signal 114 comprising the areas underneath the envelopes of the squared amplitudes of the Fourier transforms of the pathlength-encoded analog signals 86.

The multi-channel optical detector chip 24*c* (via the ADC(s) 76) then digitizes the sets of low-bandwidth analog signals 114*a*, 114*b* (or alternatively the multi-channel optical detector chip 24*d* (via the ADC(s) 76) digitizes the low-bandwidth analog signals 114) and serially outputs a plurality of low-bandwidth digital signals 116 (step 260). In digitizing the sets of low-bandwidth analog signals 114*a*, 114*b* (or analog signals 114), each ADC 76 may sequentially close the sets of switches 78*a*, 78*b* coupled to the sets of smoothing circuits 106*a*, 106*b* corresponding to each dimension (e.g., column) of analog channels 62, such that the ADC 76 sequentially digitizes the sets of low-bandwidth analog signals 114*a*, 114*b* (or analog signals 114), and serially outputs sets of low-bandwidth digital signals 116 corresponding to the column of analog channels 62.

The processor 30 reduces the sets of low-bandwidth digital signals 116 to single digital signals (e.g., by computing a mean of the low-bandwidth digital signals 116) and stores the single low-bandwidth digital signals in memory (not shown) (step 262). That is, the processor 30 computes the mean of the first low-bandwidth digital signals 116 respectively in the sets of low-bandwidth digital signals 116, computes the mean of the of the first low-bandwidth digital signals 116 respectively in the sets of low-bandwidth digital signals 116, and so forth, to generate single low-bandwidth digital signals (in the illustrated embodiment, two).

The controller 28 selects a different optical pathlength by optically or electrically shifting the transfer functions of the frequency filter assemblies and the frequency band of the high-bandwidth analog signals 80 relative to each other (step 228) in the manner described above in method 200, and repeats steps 204-220 and 252-262, where the source light 32 of the optical source 20 is swept over the range of optical wavelengths (step 204), the interferometer 22 generates the interference light pattern 40 (step 206-210), the multi-channel optical detector chip 24*c*, 24*d* simultaneously detects the subsets of optical modes of the interference light pattern 40 during each of the measurement period(s) t, outputs the plurality of high-bandwidth analog signals 80 respectively corresponding to the different subsets of optical modes of the interference light pattern 40 (step 212), and parallel processes the high-bandwidth analog signals 80 and outputs sets of low-bandwidth digital signals 116 (steps 214-220 and 252-260), and the processor 30 reduces the sets of low-bandwidth digital signals 116 to single low-bandwidth digital signals for storage in memory (step 262).

Once the low-bandwidth digital signals 116 have been acquired, reduced, and stored in memory for all of the selected optical pathlengths, the processor 30 then fits the points obtained from the low-bandwidth digital signals 116 in the case of the multi-channel optical detector chip 24*c* (or derived from the areas obtained from the low-bandwidth digital signals 116 in the case of the multi-channel optical detector chip 24*d*) for each analog channel 62 to the decorrelation speed function $$J_0 \frac{2}{\tau[\omega^2 + (1/\tau)^2]}$$

to extract the decorrelation time constant τ, which can then be analyzed over several periods (e.g., several sweeps of the optical source 20) (step 264), and determines the presence and depth (correlated to the selected optical pathlength L1-L4) of any change in the physiologically-dependent optical signal, based on the extracted decorrelation time constant (step 266). The processor 30 may then perform post-processing on the localized physiologically-dependent optical signal, e.g., determining the level and location of neural activity within the brain 12 (step 232).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A non-invasive optical detection system, comprising:
an optical source configured for generating source light having a range of optical wavelengths during each of at least one measurement period;
an interferometer configured for splitting the source light into sample light, which propagates along a sample arm of the interferometer, and reference light, which propagates along a reference arm of the interferometer, delivering the sample light into a sample, such that the sample light is scattered by the sample, resulting in signal light that exits the sample, and combining, during each of the at least one measurement period, the signal light and the reference light into an interference light pattern having a plurality of optical modes;
a plurality of optical detectors configured for respectively detecting different subsets of the plurality of optical modes of the interference light pattern, and respectively outputting a plurality of high-bandwidth analog signals corresponding to the plurality of different subsets of optical modes of the interference light pattern;
analog compression circuitry comprising a plurality of filter assemblies configured for respectively frequency filtering the plurality of high-bandwidth analog signals, and respectively outputting a plurality of pathlength-encoded analog signals encoded with one of a plurality of optical pathlengths of the signal light, the analog compression circuity configured for respectively extracting at least one characteristic of each of the plurality of pathlength-encoded analog signals, and respectively outputting a plurality of low-bandwidth digital signals respectively comprising the extracted characteristics; and
at least one processor configured for analyzing the sample at a depth corresponding to the one optical pathlength based on the extracted characteristics.

2. The non-invasive optical detection system of claim 1, wherein each subset of optical modes of the interference light pattern comprises a single optical mode.

3. The non-invasive optical detection system of claim 1, wherein each subset of optical modes of the interference light pattern comprises multiple spatially adjacent optical modes.

4. The non-invasive optical detection system of claim 1, wherein the optical source is configured for sweeping the source light over the range of optical wavelengths during each of the at least one measurement period.

5. The non-invasive optical detection system of claim 1, wherein the sample is an anatomical structure.

6. The non-invasive optical detection system of claim 5, wherein the signal light is physiologically encoded with a physiologically-dependent optical signal in the anatomical structure, and the at least one processor is configured for identifying a change in the physiologically-dependent optical signal in the anatomical structure based on the plurality of low-bandwidth digital signals.

7. The non-invasive optical detection system of claim 6, wherein the anatomical structure is a brain, the physiologically-dependent optical signal is indicative of neural activity, and the at least processor is configured for identifying neural activity in the brain based on the identified change in the physiologically-dependent optical signal.

8. The non-invasive optical detection system of claim 7, wherein the physiologically-dependent optical signal is one of a fast-optical signal and a hemodynamic signal.

9. The non-invasive optical detection system of claim 1, wherein each of the at least one measurement period is equal to or less than a speckle decorrelation time of the sample.

10. The non-invasive optical detection system of claim 1, wherein the at least one processor is further configured for reducing the plurality of low-bandwidth digital signals to a single low-bandwidth digital signal, and the at least one processor is configured for analyzing the sample based on the at least one extracted characteristic in the single low-bandwidth digital signal.

11. The non-invasive optical detection system of claim 1, further comprising an optical detector chip in which the plurality of optical detectors and the analog compression circuitry are integrated.

12. The non-invasive optical detection system of claim 1, wherein the analog compression circuitry further comprises:
a plurality of rectifiers configured for respectively rectifying the plurality of pathlength-encoded analog signals, and respectively outputting a plurality of rectified analog signals;
a plurality of smoothing circuits configured for respectively smoothing the plurality of rectified analog signals, and respectively outputting a plurality of low-bandwidth analog signals comprising the extracted characteristics; and
at least one analog-to-digital converter (ADC) configured for digitizing the plurality of low-bandwidth analog signals, and outputting the plurality of low-bandwidth digital signals; and
wherein the at least one processor is configured for analyzing the sample at the depth corresponding to the one optical pathlength based on the plurality of low-bandwidth digital signals.

13. The non-invasive optical detection system of claim 12, wherein the at least one ADC comprises a single ADC, and the non-invasive optical detection system further comprises a plurality of switches coupled between the plurality of smoothing circuits and the single ADC, wherein the plurality of switches is configured for being sequentially closed, such that the ADC serially digitizes the plurality of low-bandwidth analog signals, and serially outputs the plurality of low-bandwidth digital signals.

14. The non-invasive optical detection system of claim 12, wherein the plurality of filter assemblies respectively comprises a plurality of band-pass filters configured for respectively band-pass filtering the plurality of high-bandwidth analog signals, and respectively outputting the plurality of pathlength-encoded analog signals.

15. The non-invasive optical detection system of claim 12, wherein the plurality of frequency filter assemblies respectively comprises:
a plurality of mixers configured for respectively frequency mixing the plurality of high-bandwidth analog signals with a base frequency, and respectively outputting a plurality of frequency down-shifted analog signals; and
a plurality of low-pass filters configured for respectively low-pass filtering the plurality of frequency down-shifted analog signals, and respectively outputting the plurality of pathlength-encoded analog signals.

16. The non-invasive optical detection system of claim 12, wherein the frequency filter assemblies comprise a transfer function, the non-invasive optical detection system further comprises an optical pathlength selection device configured for selecting the one optical pathlength by shifting the transfer function of the plurality of filter assemblies and a frequency band of plurality of high-bandwidth analog signals relative to each other.

17. The non-invasive optical detection system of claim 16, wherein the optical pathlength selection device is configured for optically shifting the transfer function of the respective filter assembly and the frequency band relative to each other.

18. The non-invasive optical detection system of claim 17, wherein the optical pathlength selection device comprises a controller configured for mechanically adjusting a mirror arrangement that adjusts the length of the reference arm of the interferometer relative to the length of the sample arm of the interferometer, thereby optically shifting the frequency band.

19. The non-invasive optical detection system of claim 17, wherein the optical pathlength selection device comprises a controller configured for adjusting an optical sweep rate at which the optical source is swept over a range of optical wavelengths during each of the at least one measurement period, thereby optically shifting the frequency band.

20. The non-invasive optical detection system of claim 16, wherein the optical pathlength selection device is configured for electrically shifting the transfer function of the respective filter assembly and the frequency band relative to each other.

21. The non-invasive optical detection system of claim 20, wherein the optical pathlength selection device comprises a k-clock module configured for generating a k-clock signal having a frequency, and a phased lock loop (PLL) circuit configured for generating a control signal having a frequency that is an adjustable ratio of the frequency of the k-clock signal, wherein the plurality of filter assemblies is configured for electrically shifting the transfer function and the frequency band relative to each other in response to the adjusted frequency of the control signal.

22. The non-invasive optical detection system of claim 1, wherein the at least one extracted characteristic comprises an envelope of at least one frequency of each pathlength-encoded analog signal.

23. The non-invasive optical detection system of claim 1, wherein the analog compression circuitry is configured for computing the squared amplitude of the Fourier transform of each of the plurality of pathlength-encoded analog signals, and extracting the at least one characteristic from the squared amplitude of the Fourier transform of each of the plurality of pathlength-encoded analog signals.

24. The non-invasive optical detection system of claim 23, wherein the analog compression circuity comprises:
a first plurality of rectifiers configured for respectively rectifying the plurality of high pathlength-encoded analog signals, and respectively outputting a first plurality of rectified analog signals;
a plurality of low-pass filters configured for respectively low-pass filtering the first plurality of rectified analog signals, and respectively outputting a plurality of low-bandwidth analog signals; and
a second plurality of rectifiers configured for respectively rectifying the plurality of low-bandwidth analog signals, and respectively outputting a second plurality of rectified analog signals respectively representing the absolute squares of the Fourier transforms of the plurality of pathlength-encoded analog signals;
wherein the analog compression circuitry is configured for respectively extracting the at least one characteristic from each of the second plurality of rectified analog signals.

25. The non-invasive optical detection system of claim 23, wherein the at least one characteristic comprises a plurality of points on an envelope of the squared amplitude of the Fourier transform of each of the plurality of pathlength-encoded analog signals.

26. The non-invasive optical detection system of claim 25, wherein the analog compression circuitry comprises:
a plurality of sets of band-pass filters, each set of band-pass filters respectively having a plurality of different center frequencies, the plurality of sets of band-pass filters configured for respectively band-pass filtering the squared amplitude of the Fourier transforms of the plurality of pathlength-encoded analog signals, and respectively outputting a plurality of sets of band-pass filtered analog signals, each set of band-pass filtered analog signals respectively comprising the plurality of points;
a plurality of sets of smoothing circuits configured for respectively smoothing the plurality of sets of band-pass filtered analog signals, and respectively outputting a plurality of sets of low-bandwidth analog signals, each set of low-bandwidth analog signals respectively comprising the plurality of points; and
at least one analog-to-digital converter (ADC) configured for digitizing the plurality of sets of low-bandwidth analog signals, and outputting the plurality of low-bandwidth digital signals.

27. The non-invasive optical detection system of claim 23, wherein the at least one characteristic comprises an area underneath an envelope of the squared amplitude of the Fourier transform of each of the plurality of the pathlength-encoded analog signals.

28. The non-invasive optical detection system of claim 27, wherein the analog compression circuitry comprises:
a plurality of integrators configured for respectively integrating the squared amplitude of the Fourier transforms of the plurality of pathlength-encoded analog signals, and respectively outputting a plurality of low-bandwidth analog signals respectively comprising the areas; and
at least one analog-to-digital converter (ADC) configured for digitizing the plurality of low-bandwidth analog signals, and outputting the plurality of low-bandwidth digital signals.

* * * * *